(12) United States Patent
Empey et al.

(10) Patent No.: US 11,623,004 B2
(45) Date of Patent: Apr. 11, 2023

(54) COMPOSITIONS AND METHODS FOR VACCINATION AGAINST RESPIRATORY SYNCYTIAL VIRUS INFECTION

(71) Applicants: UNIVERSITY OF PITTSBURGH-OF THE COMMONWEALTH SYSTEM OF HIGHER EDUCATION, Pittsburgh, PA (US); CALDER BIOSCIENCES INC., New York, NY (US); VAXINE PTY LTD, Warradale (AU)

(72) Inventors: Kerry McGarr Empey, Mars, PA (US); Nikolai Petrovsky, Warradale (AU); Christopher Marshall, New York, NY (US)

(73) Assignees: UNIVERSITY OF PITTSBURGH OF THE COMMONWEALTH SYSTEM OF HIGHER EDUCATION, Pittsburgh, PA (US); CALDER BIOSCIENCES INC., Brooklyn, NY (US); VAXINE PTY LTD, Warradale (AU)

(*) Notice: Subject to any disclaimer, the term of this patent is extended or adjusted under 35 U.S.C. 154(b) by 0 days.

(21) Appl. No.: 16/981,439

(22) PCT Filed: Mar. 15, 2019

(86) PCT No.: PCT/US2019/022549
§ 371 (c)(1),
(2) Date: Sep. 16, 2020

(87) PCT Pub. No.: WO2019/178521
PCT Pub. Date: Sep. 19, 2019

(65) Prior Publication Data
US 2021/0023195 A1  Jan. 28, 2021

Related U.S. Application Data

(60) Provisional application No. 62/644,060, filed on Mar. 16, 2018.

(51) Int. Cl.
*A61K 39/12* (2006.01)
*A61P 31/14* (2006.01)
*C07K 16/10* (2006.01)
*A61K 39/00* (2006.01)

(52) U.S. Cl.
CPC .............. *A61K 39/12* (2013.01); *A61P 31/14* (2018.01); *C07K 16/1027* (2013.01); *A61K 2039/55* (2013.01); *A61K 2039/55505* (2013.01); *A61K 2039/55561* (2013.01); *A61K 2039/55583* (2013.01)

(58) Field of Classification Search
None
See application file for complete search history.

(56) References Cited

U.S. PATENT DOCUMENTS

| 7,037,894 B2 | 5/2006 | Marshall et al. |
| 9,393,297 B2 | 6/2016 | Marshall et al. |
| 10,017,543 B2* | 7/2018 | Kwong ................ C07K 14/005 |
| 10,125,172 B2* | 11/2018 | Marshall ............. C07K 14/005 |
| 10,155,023 B2 | 12/2018 | Marshall et al. |
| 2010/0068217 A1 | 3/2010 | Kwong et al. |
| 2010/0239593 A1 | 9/2010 | Spits et al. |
| 2012/0070446 A1 | 3/2012 | Tsuboi et al. |
| 2014/0248314 A1* | 9/2014 | Swanson ................ A61P 31/14 424/211.1 |
| 2015/0030622 A1* | 1/2015 | Marshall ............. C07K 14/005 424/186.1 |
| 2016/0046675 A1 | 2/2016 | Kwong et al. |
| 2017/0239349 A1 | 8/2017 | Agadjanyan et al. |

FOREIGN PATENT DOCUMENTS

| AU | 2017203501 | 8/2017 |
| WO | 2012175518 | 12/2012 |
| WO | 2019/032480 | 2/2019 |

OTHER PUBLICATIONS

McClellan et al. Science vol. 342, p. 592ff (Year: 2013).*
McClellan et al (Science vol. 340, pp. 1113-1117 (Year: 2013).*
Wong et al. (Human Vaccines & Immunotherapeutics, 12:8, 2096-2105 (Year: 2016).*

(Continued)

*Primary Examiner* — Shanon A. Foley
*Assistant Examiner* — Myron G Hill
(74) *Attorney, Agent, or Firm* — Meunier Carlin & Curfman LLC

(57) ABSTRACT

Disclosed herein are compositions for vaccination against respiratory syncytial virus (RSV) comprising a RSV F polypeptide stabilized in a prefusion conformation and an inulin adjuvant. Also disclosed herein are methods of vaccinating a subject against a respiratory syncytial virus (RSV) infection comprising administering to the subject an RSV F polypeptide stabilized in a prefusion conformation and an inulin adjuvant. In some embodiments, the subject is a female, and the method can reduce RSV infection in the subject and/or in the offspring of the subject. In some embodiments, the method decreases vaccine-enhanced respiratory disease (VERD) and/or eosinophilia in the subject or offspring of the subject.

14 Claims, 20 Drawing Sheets
Specification includes a Sequence Listing.

(56) References Cited

OTHER PUBLICATIONS

Palomo et al.. Influence of respiratory syncytial virus F glycoprotein conformation on induction of protective immune responses. J Virol 90:5485-5498. (Year: 2016).*
Sequence Comparison for SEQ ID# 6 (Year: 2022).*
Acosta PL, Caballero MT, Polack FP. Brief History and Characterization of Enhanced Respiratory Syncytial Virus Disease. Clin Vaccine Immunol. 2015;23(3):189-95. doi: 10.1128/CVI.00609-15. PubMedPMID: 26677198; PubMed Central PMCID: PMCPMC4783420.
Altschul, S. F., Madden, T. L., Schäffer, A. A., Zhang, J., Zhang, Z., Miller, W., & Lipman, D. J. (1997). Gapped BLAST and PSI-BLAST: a new generation of protein database search programs. Nucleic acids research, 25(17), 3389-3402.
Altschul, S. F., Gish, W., Miller, W., Myers, E. W., & Lipman, D. J. (1990). Basic Tocal alignment search tool. Journal of molecular biology, 215(3), 403-410.
Anderson LJ, Heilman CA. Protective and disease-enhancing immune responses to respiratory syncytial virus. J Infect Dis. 1995;171(1):1-7. Epub Jan. 1, 1995. PubMed PMID: 7798649.
Asquith KL, Ramshaw HS, Hansbro PM, Beagley KW, Lopez AF, Foster PS. The IL-3/IL-5/GM-CSF Common β Receptor Plays a Pivotal Role in the Regulation of Th2 Immunity and Allergic Airway Inflammation. The Journal of Immunology. 2008;180(2):1199-206. doi: 10.4049/jimmunol.180.2.1199.
B.V. JVP. NCT03606512: A Study to Evaluate the Safety, Reactogenicity, and Immunogenicity of Adenovirus Serotype 26 Based Respiratory Syncytial Virus Pre-fusion (AD26.RSV.Pre-F) Vaccine in RESV-Seronegative Toddlers 12 to 24 Months of Age Clinicaltrials.gov: US National Library of Medicine; 2019 [cited Feb. 4, 2019, 2019].
Bagnasco D, Ferrando M, Varricchi G, Puggioni F, Passalacqua G, Canonica GW. Anti-Interleukin 5 (IL-5) and IL-5Ra Biological Drugs: Efficacy, Safety, and Future Perspectives in Severe Eosinophilic Asthma. Frontiers in Medicine. 2017;4(135). doi: 10.3389/fmed.2017.00135.
Benoit A, Huang Y, Proctor J, Rowden G, Anderson R. Effects of alveolar macrophage depletion on liposomal vaccine protection against respiratory syncytial virus (RSV). Clin Exp Immunol. 2006;145(1):147-54. Epub Jun. 24, 2006. doi 10.1111/j.1365-2249.2006.03114.x. PubMed PMID: 16792685; PubMed Central PMCID: PMCPMC1941998.
Blanco JCG, Pletneva LM, Otoa RO, Patel MC, Vogel SN, Boukhvalova MS. Preclinical assessment of safety of maternal vaccination against respiratory syncytial virus (RSV) in cotton rats. Vaccine. 2017;35(32):3951-8. Epub Jun. 19, 2017. doi: 10.1016/j.vaccine.2017.06.009. PubMed PMID: 28624306.
Castilow EM, Meyerholz DK, Varga Sm. IL-13 Is Required for Eosinophil Entry into the Lung during Respiratory Syncytial Virus Vaccine-Enhanced Disease. The Journal of Immunology. 2008;180(4):2376.
Collins PL, Graham BS. Viral and host factors in human respiratory syncytial virus pathogenesis. J Virol. 2008;82(5):2040-55. Epub Oct. 12, 2007. doi: 10.1128/JVI.01625-07. PubMed PMID: 17928346; PubMed Central PMCID: PMC2258918.
Connors M, Kulkarni AB, Firestone CY, Holmes KL, Morse HC, Sotnikov AV, et al. Pulmonary histopathology induced by respiratory syncytial virus (RSV) challenge of formalin-inactivated RSV-immunized BALB/c mice is abrogated by depletion of CD4+ T cells. Journal of Virology. 1992;66(12):7444-51.
Corti, Davide, et al. "Cross-neutralization of four paramyxoviruses by a human monoclonal antibody." Nature 501.7467 (2013): 439-443.
De Gregorio E, Tritto E, Rappuoli R. Alum adjuvanticity: Unraveling a century old mystery. European Journal of Immunology. 2008;38(8):2068-71. doi: 10.1002/eji.200838648.
Delgado MF, Coviello S, Monsalvo AC, Melendi GA, Hernandez JZ, Batalle JP, et al. Lack of antibody affinity maturation due to poor Toll-like receptor stimulation Teads to enhanced respiratory syncytial virus disease. Nature medicine. 2009;15(1):34-41. Epub Dec. 17, 2008. doi: 10.1038/nm.1894. PubMed PMID: 19079256; PubMed Central PMCID: PMC2987729.
Duan, M., et al. "CD11b immunophenotyping identifies inflammatory profiles in the mouse and human lungs." Mucosal immunology 9.2 (2016): 550-563.
Eichinger KM, Egaña L, Orend JG, Resetar E, Anderson KB, Patel R, et al. Alveolar macrophages support interferon gamma-mediated viral clearance in RSV-infected neonatal mice. Respiratory Research. 2015;16:122. doi: 10.1186/s12931-015-0282-7. PubMed PMID: PMC4594958.
Empey KM OJ, Stokes Peebles R, Egana L, Norris KA, Oury TD, Kolls JK. Stimulation of immature lung macrophages with intranasal interferon gamma in a novel neonatal mouse model of respiratory syncytial virus infection. PLoS One. 2012;7(7). PubMed Central PMCID: PMCPMC3391240.
Empey KM, Hollifield M, Garvy BA. Exogenous Heat-Killed *Escherichia coli* Improves Alveolar Macrophage Activity and Reduces Pneumocystis carinii Lung Burden in Infant Mice. Infection and Immunity. 2007;75(7):3382-93.
Englund JA. Passive protection against respiratory syncytial virus disease in infants: the role of maternal antibody. Pediatr Infect Dis J. 1994;13(5):449-53. Epub May 1, 1994. PubMed PMID: 8072835.
Falsey AR, Singh HK, Walsh EE. Serum antibody decay in adults following natural Yespiratory syncytial virus infection. Journal of Medical Virology. 2006;78(11):1493-7. doi: 10.1002/jmv.20724.
Feldman AS, He Y, Moore ML, Hershenson MB, Hartert TV. Toward primary prevention of asthma. Reviewing the evidence for early-life respiratory viral infections as modifiable risk factors to prevent childhood asthma. Am J Respir Crit Care Med. 2015;191(1):34-44. Epub Nov. 5, 2014. doi: 10.1164/rccm.20.
Flood-Page P, Swenson C, Faiferman I, Matthews J, Williams M, Brannick L, et al. A study to evaluate safety and efficacy of mepolizumab in patients with moderate persistent asthma. Am J Respir Crit Care Med. 2007; 176(11):1062-71. doi: 10.1164/rccm.200701-085OC. PubMed PMID: 17872493.
Fuentes S, Crim RL, Beeler J, Teng MN, Golding H, Khurana S. Development of a simple, rapid, sensitive, high-throughput luciferase reporter based microneutralization test for measurement of virus neutralizing antibodies following Respiratory Syncytial Virus vaccination and infection. Vaccine. 2013;31(37):3987-94. doi: 10.1016/j.vaccine.2013.05.088. PubMed PMID: PMC3779065.
Golde WT, Gollobin P, Rodriguez LL. A rapid, simple, and humane method for submandibular bleeding of mice using a lancet. Lab Animal. 2005;34:39. doi: 10.1038/laban1005-39.
Goodier MR, Lusa C, Sherratt S, Rodriguez-Galan A, Behrens R, Riley EM. Sustained Immune Complex-Mediated Reduction in CD 16 Expression after Vaccination Regulates NK Cell Function. Front Immunol. 2016;7:384. doi: 10.3389/fimmu.2016.00384. PubMed PMID: 27725819; PubMed Central PMCID: PMCPMC5035824.
Goodier, Martin R., et al. "Sustained immune complex-mediated reduction in CD16 expression after vaccination regulates NK cell function." Frontiers in immunology 7 (2016): 384. PMID27725 819.
Graham BS BL, Wright PF, Karzon DT. Role of T lymphocyte subsets in the pathogenesis of primary infection and rechallenge with respiratory syncytial virus in mice. J Clin Invest. 1991;88(3):1026-33. doi: 10.1172/JCI115362. PubMed Central PMCID: PMCPMC295511.
Graham BS, Perkins MD, Wright PF, Karzon DT. Primary respiratory syncytial virus infection in mice. J Med Virol. 1988;26(2):153-62. PubMed PMID: 3183639.
Graham BS. Vaccine development for respiratory syncytial virus. Current Opinion in Virology. 2017;23:107-12. doi: https://doi.org/10.1016/j.coviro.2017.03.012.
Green MG, Petroff N, La Perle KMD, Niewiesk S. Characterization of Cotton Rat (*Sigmodon hispidus*) Eosinophils, Including Their Response to Respiratory Syncytial Virus Infection. Comp Med. 2018;68(1):31-40. Epub Feb. 21, 2018. PubMed PMID: 29460719; PubMed Central PMCID: PMCPMC5824137.
Griffin MP, Khan AA, Esser MT, Jensen K, Takas T, Kankam MK, et al. Safety, Tolerability, and Pharmacokinetics of MEDI8897, the Respiratory Syncytial Virus Prefusion F-Targeting Monoclonal Anti-

(56) References Cited

OTHER PUBLICATIONS body with an Extended Half-Life, in Healthy Adults. Antimicrobial Agents and Chemotherapy. 2017;61(3).
Guilliams M, Bruhns P, Saeys Y, Hammad H, Lambrecht BN. The function of Fcgamma receptors in dendritic cells and macrophages. Nat Rev Immunol. 2014; 14(2):94-108. doi: 10.1038/nri3582. PubMed PMID: 24445665.
Hall CB, Walsh EE, Long CE, Schnabel KC. Immunity to and frequency of Yeinfection with respiratory syncytial virus. J Infect Dis. 1991;163(4):693-8. Epub Apr. 1, 1991. PubMed PMID: 2010624.
Hall CB, Weinberg GA, Iwane MK, Blumkin AK, Edwards KM, Staat MA, et al. The Burden of Respiratory Syncytial Virus Infection in Young Children. New England Journal of Medicine. 2009;360(6):588-98. doi: doi:10.1056/NEJMoa0804877. PubMed PMID: 19196675.
Henikoff, Steven, and Jorja G. Henikoff. "Amino acid substitution matrices from protein blocks." Proceedings of the National Academy of Sciences 89.22 (1992): 10915-10919.
Higgins D, Trujillo C, Keech C. Advances in RSV vaccine research and development—A global agenda. Vaccine. 2016;34(26):2870-5. doi: 10.1016/j.vaccine.2016.03.109. PubMed PMID: 27105562.
Honda-Okubo Y, Barnard D, Ong CH, Peng B-H, Tseng C-TK, Petrovsky N. Severe Acute Respiratory Syndrome-Associated Coronavirus Vaccines Formulated with Delta Inulin Adjuvants Provide Enhanced Protection while Ameliorating Lung Eosinophilic Immunopathology. Journal of Virology. 2015;89(6):2995-3007.
Honda-Okubo Y, Kolpe A, Li L, Petrovsky N. A single immunization with inactivated H1N1 influenza vaccine formulated with delta inulin adjuvant (Advax) overcomes pregnancy-associated immune suppression and enhances passive neonatal protection. Vaccine. 2014;32(36):4651-9. Epub Jun. 25, 2014. doi: 10.1016/j.vaccine. 2014.06.057. PubMed PMID: 24958701; PubMed Central PMCID: PMCPMC4108551.
Honda-Okubo Y, Ong CH, Petrovsky N. Advax delta inulin adjuvant overcomes immune immaturity in neonatal mice thereby allowing single-dose influenza vaccine protection. Vaccine. 2015;33(38):4892-900. Epub Aug. 2, 2015. doi: 10.1016/j.vaccine.2015.07.051. PubMed PMID: 26232344; PubMed Central PMCID: PMCPMC4562881.
Humbles AA, Lloyd CM, McMillan SJ, Friend DS, Xanthou G, McKenna EE, et al. A Critical Role for Eosinophils in Allergic Airways Remodeling. Science. 2004;305(5691):1776.
Hussell T, Baldwin CJ, O'Garra A, Openshaw PJ. CD8+ T cells control Th2-driven pathology during pulmonary respiratory syncytial vims infection. Eur J Immunol. 1997;27(12):3341-9. doi: 10.1002/eji. 1830271233. PubMed PMID: 9464822.
Janssen WJ, Stefanski AL, Bochner BS, Evans CM. Control of lung defence by mucins and macrophages: ancient defence mechanisms with modem functions. Eur Respir J. 2016;48(4):1201-14. Epub Sep. 3, 2016. doi: 10.1183/13993003.00120-2015. PubMed PMID: 27587549; PubMed Central PMCID: PMCPMC5120543.
Janssen, William J., et al. "Control of lung defence by mucins and macrophages: ancient defence mechanisms with modem functions." European Respiratory Journal 48.4 (2016): 1201-1214. PMID:27587549.
Jha A, Jarvis H, Fraser C, Openshaw PJM. Respiratory Syncytial Vims. In: Hui DS, Rossi GA, Johnston SL, editors. SARS, MERS and other Viral Lung Infections. Wellcome Tmst-Funded Monographs and Book Chapters. Sheffield UK2016.
Johnson TR, Rothenberg ME, Graham BS. Pulmonary eosinophilia requires interleukin-5, eotaxin-1, and CD4+ T cells in mice immunized with respiratory syncytial vims G glycoprotein. Journal of Leukocyte Biology. 2008;84(3):748-59. doi: 10.1189/jlb.090762L PubMed PMID: PMC2516895.
Karlin, Samuel, and Stephen F. Altschul. "Applications and statistics for multiple high-scoring segments in molecular sequences." Proceedings of the National Academy of Sciences 90.12 (1993): 5873-5877.
Killikelly AM, Kanekiyo M, Graham BS. Pre-fusion F is absent on the surface of formalin-inactivated respiratory syncytial virus. Sci Rep. 2016;6:34108. doi: 10.1038/srep34108. PubMed PMID: 27682426; PubMed Central PMCID: PMCPMC5040956 in development.

Kim, Ki-Hye, et al. "Virus-like particle vaccine containing the F protein of Yespiratory syncytial virus confers protection without pulmonary disease by modulating specific subsets of dendritic cells and effector T cells." Journal of virology 89.22 (2015): 11692-11705.PMID 26355098.
Kim HW, Canchola JG, Brandt CD, Pyles G, Chanock RM, Jensen K, et al. Respiratory syncytial virus disease in infants despite prior administration of antigenic inactivated vaccine. Am J Epidemiol. 1969;89(4):422-34. PubMed PMID: 4305198.
Knudson CJ, Hartwig SM, Meyerholz DK, Varga SM. RSV Vaccine-Enhanced Disease Is Orchestrated by the Combined Actions of Distinct CD4 T Cell Subsets. PLOS Pathogens. 2015;11(3):e1004757. doi: 10.1371/journal.ppat.1004757.
Kwakkenbos, Mark J., et al. "Generation of stable monoclonal antibody—producing B cell receptor—positive human memory B cells by genetic programming." Nature medicine 16.1 (2010): 123-128.
Kwon YM, Hwang HS, Lee JS, Ko EJ, Yoo SE, Kim MC, et al. Maternal antibodies by passive immunization with formalin inactivated respiratory syncytial virus confer protection without vaccine-enhanced disease. Antiviral Res. 2014;104:1-6. Epub Jan. 28, 2014. doi: 10.1016/j.antiviral.2014.01.008. PubMed PMID: 24462695; PubMed Central PMCID: PMCPMC3960005.
Lee Y-T, Kim K-H, Hwang HS, Lee Y, Kwon Y-M, Ko E-J, et al. Innate and adaptive cellular phenotypes contributing to pulmonary disease in mice after respiratory syncytial virus immunization and infection. Virology. 2015;485:36-46. doi: https://doi.org/10.1016/j.virol.2015.07.001.
Lopez AF, Sanderson CJ, Gamble JR, Campbell HD, Young IG, Vadas MA. Recombinant human interleukin 5 is a selective activator of human eosinophil function. J Exp Med. 1988;167(1):219-24. PubMed PMID: 2826636; PubMed Central PMCID: PMCPMC2188822.
Lopez AF, Williamson DJ, Gamble JR, Begley CG, Harlan JM, Klebanoff SJ, et al. Recombinant human granulocyte-macrophage colony-stimulating factor stimulates in vitro mature human neutrophil and eosinophil function, surface receptor expression, and survival. J Clin Invest. 1986;78(5):1220-8. doi: 10.1172/JCI112705. PubMed PMID: 3021817; PubMed Central PMCID: PMCPMC423807.
Magro, Margarita, et al. "Neutralizing antibodies against the preactive form of Yespiratory syncytial virus fusion protein offer unique possibilities for clinical intervention." Proceedings of the National Academy of Sciences 109.8 (2012): 3089-3094.
Malloy AM, Ruckwardt TJ, Morabito KM, Lau-Kilby AW, Graham BS. Pulmonary Dendritic Cell Subsets Shape the Respiratory Syncytial Virus-Specific CD8+ T Cell Immunodominance Hierarchy in Neonates. J Immunol. 2017;198(1):394-403. Epub Nov. 30, 2016. doi: 10.4049/jimmunol.1600486. PubMed PMID: 27895172; PubMed Central PMCID: PMCPMC5849234.
Mazur NI, Horsley N, Englund JA, Nederend M, Magaret A, Kumar A, et al. Breast milk prefusion F IgG as a correlate of protection against respiratory syncytial virus acute respiratory illness. J Infect Dis. 2018. Epub Aug. 15, 2018. doi: 10.1093/infdis/jiy477. PubMed PMID: 30107412.
McLellan, Jason S., et al. "Structure of respiratory syncytial virus fusion glycoprotein in the postfusion conformation reveals preservation of neutralizing epitopes." Journal of virology 85.15 (2011): 7788-7796.
McLellan, Jason S., et al. "Structure of RSV fusion glycoprotein trimer bound to a prefusion-specific neutralizing antibody." Science 340.6136 (2013): 1113-1117.
McLellan, Jason S., et al. "Structure-based design of a fusion glycoprotein vaccine for respiratory syncytial virus." science 342. 6158 (2013): 592-598.
Meissner HC, Rennels MB, Pickering LK, Hall CB. Risk of severe respiratory syncytial virus disease, identification of high risk infants and recommendations for prophylaxis with palivizumab. Pediatr Infect Dis J. 2004;23(3):284-5. Epub Mar. 12, 2004. doi: 00006454-200403000-00034 [pii], PubMed PMID: 15014320.
Mohanty, Subhasis, et al. "Prolonged proinflammatory cytokine production in monocytes modulated by interleukin 10 after influenza vaccination in older adults." The Journal of infectious diseases 211.7 (2015): 1174-1184. PMID:25367297.

(56) References Cited

OTHER PUBLICATIONS

Murphy BR, Sotnikov AV, Lawrence LA, Banks SM, Prince GA. Enhanced pulmonary histopathology is observed in cotton rats immunized with formalin-inactivated respiratory syncytial virus (RSV) or purified F glycoprotein and challenged with RSV 3-6 months after immunization. Vaccine. 1990;8(5):497-502. Epub Oct. 1, 1990. PubMed PMID: 2251875.

Novavax. NCT02624947: A Study to Determine the Safety and Efficacy of the RSV F Vaccine to Protect Infants Via Maternal Immunization US National Library of Medicine: NIH; 2019 [cited 2019].

Novavax. NCT02247726: Rsv F Vaccine Maternal Immunization Study in Healthy Third-trimester Pregnant Women clinicaltrials. gov: US National library of Medicine; 2017 [cited 2019].

Nyiro JU, Kombe IK, Sande CJ, Kipkoech J, Kiyuka PK, Onyango CO, et al. Defining the vaccination window for respiratory syncytial virus (RSV) using ageseroprevalence data for children in Kilifi, Kenya. PLoS One. 2017;12(5):e0177803. Epub May 23, 2017. doi: 10.1371/journal.pone.0177803. PubMed PMID: 28531224; PubMed Central PMCID: PMCPMC5439681.

Olson MR, Hartwig SM, Varga SM. The No. of Respiratory Syncytial Virus (RSV)-Specific Memory CD8 T Cells in the Lung Is Critical for Their Ability to Inhibit RSV Vaccine-Enhanced Pulmonary Eosinophilia. The Journal of Immunology. 2008;181(11):7958.

Olson MR, Varga SM. CD8 T Cells Inhibit Respiratory Syncytial Virus (RSV) Vaccine-Enhanced Disease. The Journal of Immunology. 2007;179(8):5415.

Peruzzi G, Femnou L, Gil-Krzewska A, Borrego F, Week J, Krzewski K, et al. Membrane-Type 6 Matrix Metalloproteinase Regulates the Activation-Induced Downmodulation of CD 16 in Human Primary NK Cells. The Journal of Immunology. 2013;191(4):1883.

Piedra PA, Jewell AM, Cron SG, Atmar RL, Glezen WP. Correlates of immunity to Yespiratory syncytial vims (RSV) associated-hospitalization: establishment of minimum protective threshold levels of serum neutralizing antibodies. Vaccine. 2003;21(24):3479-82. Epub Jul. 10, 2003. PubMed PMID: 12850364.

Plantinga M, Guilliams M, Vanheerswynghels M, Deswarte K, Branco-Madeira F, Toussaint W, et al. Conventional and monocyte-derived CD11b(+) dendritic cells initiate and maintain T helper 2 cell-mediated immunity to house dust mite allergen. Immunity. 2013;38(2):322-35. Epub Jan. 29, 2013. doi: 10.1016/j.immuni. 2012.10.016. PubMed PMID: 23352232.

Polack FP, Teng MN, Collins PL, Prince GA, Exner M, Regele H, et al. A role for immune complexes in enhanced respiratory syncytial vims disease. J Exp Med. 2002;196(6):859-65. PubMed PMID: 12235218; PubMed Central PMCID: PMCPMC2194058.

PrabhuDas M, Adkins B, Gans H, King C, Levy O, Ramilo O, et al. Challenges in infant immunity: implications for responses to infection and vaccines. Nat Immunol. 2011;12(3):189-94. doi: 10.1038/ni0311-189. PubMed PMID: 21321588.

Prince GA, Curtis SJ, Yim KC, Porter DD. Vaccine-enhanced respiratory syncytial vims disease in cotton rats following immunization with Lot 100 or a newly prepared reference vaccine. Journal of General Virology. 2001;82(12):2881-8. doi: doi: 10.1099/0022-1317-82-12-2881.

Quan F-S, Kim Y, Lee S, Yi H, Kang S-M, Bozja J, et al. Viruslike Particle Vaccine Induces Protection Against Respiratory Syncytial Virus Infection in Mice. The Journal of Infectious Diseases. 2011;204(7):987-95. doi: 10.1093/infdis/jir474.

Raycroft, Maurice T., et al. "Inhibition of antigen trafficking through scavenger receptor A." Journal of Biological Chemistry 287.8 (2012): 5310-5316. PMID: 22215667.

Rittirsch D, Flierl MA, Day DE, Nadeau BA, Zetoune FS, Sarma JV, et al. Cross-Talk between TLR4 and FcγReceptorIII (CD16) Pathways. PLOS Pathogens. 2009;5(6):e1000464. doi: 10.1371/journal.ppat.1000464.

Romee R, Foley B, Lenvik T, Wang Y, Zhang B, Ankarlo D, et al. NK cell CD16 surface expression and function is regulated by a disintegrin and metalloprotease-17 (ADAM17). Blood. 2013;121(18):3599.

Rothenberg ME, Owen WF, Jr., Silberstein DS, Woods J, Soberman RJ, Austen KF, et al. Human eosinophils have prolonged survival, enhanced functional properties, and become hypodense when exposed to human interleukin 3. J Clin Invest. 1988;81(6):1986-92. doi: 10.1172/JCI113547. PubMed PMID: 3133397; PubMed Central PMCID: PMCPMC442652.

Ruckwardt TJ, Malloy AM, Morabito KM, Graham BS. Quantitative and qualitative deficits in neonatal lung-migratory dendritic cells impact the generation of the CD8+ T cell response. PLoS Pathog. 2014;10(2):e1003934. Epub Feb. 20, 2014. doi: 10.1371/journal.ppat.1003934. PubMed PMID: 24550729; PubMed Central PMCID: PMCPMC3923758.

Ruckwardt TJ, Morabito KM, Bar-Haim E, Nair D, Graham BS. Neonatal mice possess two phenotypically and functionally distinct lung-migratory CD103(+) dendritic cell populations following respiratory infection. Mucosal Immunol. 2018; 11(1):186-98. Epub Apr. 6, 2017. doi: 10.1038/mi.2017.28. PubMed PMID: 28378805; PubMed Central PMCID: PMCPMC5628111.

Ruckwardt, Tracy J., et al. "Neonatal mice possess two phenotypically and functionally distinct lung-migratory CD 103+ dendritic cell populations following respiratory infection." Mucosal immunology 11.1 (2018): 186-198. PMID:28378805.

Sastre P, Melero JA, Garcia-Barreno B, Palomo C. Comparison of affinity chromatography and adsorption to vaccinia virus recombinant infected cells for depletion of antibodies directed against respiratory syncytial virus glycoproteins present in a human immunoglobulin preparation. J Med Virol. 2005;76(2):248-55. doi: 10.1002/jmv.20349. PubMed PMID: 15834867.

Sastry M, Zhang B, Chen M, Joyce MG, Kong W-P, Chuang G-Y, et al. Adjuvants and the vaccine response to the DS-Cav1-stabilized fusion glycoprotein of respiratory syncytial virus. PLOS ONE. 2017;12(10):e0186854. doi: 10.1371/journal.pone.0186854.

Sastry M, Zhang B, Chen M, Joyce MG, Kong WP, Chuang GY, et al. Adjuvants and the vaccine response to the DS-Cav1-stabilized fusion glycoprotein of Yespiratory syncytial virus. PLoS One. 2017;12(10):e0186854. Epub Oct. 27, 2017. doi: 10.1371/journal.pone.0186854. PubMed PMID: 29073183; PubMed Central PMCID: PMCPMC5658087.

Schmidt ME, Knudson CJ, Hartwig SM, Pewe LL, Meyerholz DK, Langlois RA, et al. Memory CD8 T cells mediate severe immunopathology following respiratory syncytial virus infection. PLoS Pathog. 2018;14(1):e1006810. doi: 10.1371/journal.ppat.1006810. PubMed PMID: 29293660; PubMed Central PMCID: PMCPMC5766251.

Schneider-Ohrum K, Cayatte C, Bennett AS, Rajani GM, McTamney P, Nacel K, et al. Immunization with Low Doses of Recombinant Postfusion or Prefusion Respiratory Syncytial Virus F Primes for Vaccine-Enhanced Disease in the Cotton Rat Model Independently of the Presence of a Th1-Biasing (GLA-SE) or Th2-Biasing (Alum) Adjuvant. J Virol. 2017;91(8). doi: 10.1128/JVI.02180-16. PubMed PMID: 28148790; PubMed Central PMCDI: PMCPMC5375676.

Shi T, McAllister DA, O'Brien KL, Simoes EAF, Madhi SA, Gessner BD, et al. Global, regional, and national disease burden estimates of acute lower respiratory infections due to respiratory syncytial virus in young children in 2015: a systematic review and modelling study. The Lancet. 2017;390(10098):946-58.

Siegelman MH, Stanescu D, Estess P. The CD44-initiated pathway of T-cell extravasation uses VLA-4 but not LFA-1 for firm adhesion. J Clin Invest. 2000;105(5):683-91. Epub Mar. 11, 2000. doi: 10.1172/JCI8692. PubMed PMID: 10712440; PubMed Central PMCID: PMCPMC292454.

Soukup, Joleen M., and Susanne Becker. "Role of monocytes and eosinophils in human respiratory syncytial virus infection in vitro." Clinical immunology 107.3 (2003): 178-185.

Stevens WW, Falsey AR, Braciale TJ. RSV 2007: recent advances in respiratory syncytial virus research. Viral Immunol. 2008;21(2):133-40. doi: 10.1089/vim.2008.0012. PubMed PMID: 18570587; PubMed Central PMCID: PMCPMC3140300.

Stevens WW, Sun J, Castillo JP, Braciale TJ. Pulmonary Eosinophilia Is Attenuated by Early Responding CD8(+) Memory T Cells in a

(56) References Cited

OTHER PUBLICATIONS

Murine Model of RSV Vaccine-Enhanced Disease. Viral Immunology. 2009;22(4):243-51. doi: 10.1089/vim.2009.0016. PubMed PMID: PMC2885249.

Stier MT, Peebles RS, Jr. Host and Viral Determinants of Respiratory Syncytial Virus-induced Airway Mucus. Ann Am Thorac Soc. 2018;15(Supplement_3):S205-S9. Epub Nov. 16, 2018. doi: 10.1513/AnnalsATS.201806-380AW. PubMed PMID: 30431348; PubMed Central PMCID: PMCPMC6322028.

Swanson, Kurt A., et al. "Structural basis for immunization with postfusion respiratory syncytial virus fusion F glycoprotein (RSV F) to elicit high neutralizing antibody titers." Proceedings of the National Academy of Sciences 108.23 (2011): 9619-9624.

Tanaka H, Komai M, Nagao K, Ishizaki M, Kajiwara D, Takatsu K, et al. Role of Interleukin-5 and Eosinophils in Allergen-Induced Airway Remodeling in Mice. American Journal of Respiratory Cell and Molecular Biology. 2004;31(1):62-8. doi: 10.1165/rcmb.2003-0305OC.

Tjota, Melissa Y., et al. "Signaling through FcRγ-associated receptors on dendritic cells drives IL-33-dependent TH2-type responses." Journal of allergy and clinical immunology 134.3 (2014): 706-713. PMID: 25088053.

Walsh EE, Falsey AR. Age related differences in humoral immune response to Yespiratory syncytial virus infection in adults. J Med Virol. 2004;73(2):295-9. Epub May 4, 2004. doi: 10.1002/jmv. 20090. PubMed PMID: 15122807.

Walsh EE, Falsey AR. Humoral and mucosal immunity in protection from natural Yespiratory syncytial virus infection in adults. J Infect Dis. 2004;190(2):373-8. Epub Jun. 25, 2004. doi: 10.1086/421524. PubMedPMID: 15216475.

Wang Y, Rahman D, Lehner T. A Comparative Study of Stress-mediated Immunological Functions with the Adjuvanticity of Alum. Journal of Biological Chemistry. 2012;287(21):17152-60.

Waris ME, Tsou C, Erdman DD, Day DB, Anderson LJ. Priming with live respiratory syncytial virus (RSV) prevents the enhanced pulmonary inflammatory response seen after RSV challenge in BALB/c mice immunized with formalin-inactivated RSV. J Virol. 1997;71(9):6935-9. Epub Sep. 1, 1997. PubMed PMID 9261421; PubMed Central PMCID: PMCPMC191977.

Wills-Karp M, Luyimbazi J, Xu X, Schofield B, Neben TY, Karp CL, et al. Interleukin-13: central mediator of allergic asthma. Science. 1998;282(5397):2258-61. PubMed PMID: 9856949.

Wong, Terianne M., et al. "Delta inulin-derived adjuvants that elicit Th1 phenotype following vaccination reduces respiratory syncytial virus lung titers without a reduction in lung immunopathology." Human vaccines & immunotherapeutics 12.8 (2016): 2096-2105.

Zomer-Kooijker K, van der Ent CK, Ermers MJ, Uiterwaal CS, Rovers MM, Bont LJ. Increased risk of wheeze and decreased lung function after respiratory syncytial virus infection. PLoS One. 2014;9(1):e87162.

International Search Report and Written Opinion dated Jun. 10, 2019, from International Application No. PCT/US2019/022549, 9 pages.

Wong, TM et al. "Delta inulin-derived adjuvants that elicit Th1 phenotype following vaccination reduces respiratory syncytial virus lung titers without a reduction in lung immunopathology", Human Vaccines & Immunotherapeutics 2016, vol. 12, No. 8, 2096-2105.

* cited by examiner

SEQUENCE LISTING

<160> NUMBER OF SEQ ID NOS: 9

<210> SEQ ID NO 1
<211> LENGTH: 513
<212> TYPE: PRT
<213> ORGANISM: respiratory syncytial virus (RSV), subtype A

<400> SEQUENCE: 1

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Lys Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
```

```
            225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
                260                 265                 270

Leu Met Ser Asn Asn Val Gln Ile Val Arg Gln Gln Ser Tyr Ser Ile
                275                 280                 285

Met Ser Ile Ile Lys Glu Glu Val Leu Ala Tyr Val Val Gln Leu Pro
                290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
                340                 345                 350

Pro Gln Ala Glu Thr Cys Lys Val Gln Ser Asn Arg Val Phe Cys Asp
                355                 360                 365

Thr Met Asn Ser Leu Thr Leu Pro Ser Glu Val Asn Leu Cys Asn Val
                370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
                420                 425                 430

Lys Thr Phe Ser Asn Gly Cys Asp Tyr Val Ser Asn Lys Gly Val Asp
                435                 440                 445

Thr Val Ser Val Gly Asn Thr Leu Tyr Tyr Val Asn Lys Gln Glu Gly
                450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
                500                 505                 510

Leu

<210> SEQ ID NO 2
<211> LENGTH: 513
<212> TYPE: PRT
<213> ORGANISM: respiratory syncytial virus (RSV), subtype B

<400> SEQUENCE: 2

Met Glu Leu Leu Ile His Arg Ser Ser Ala Ile Phe Leu Thr Leu Ala
1               5                   10                  15

Ile Asn Ala Leu Tyr Leu Thr Ser Ser Gln Asn Ile Thr Glu Glu Phe
                20                  25                  30

Tyr Gln Ser Thr Cys Ser Ala Val Ser Arg Gly Tyr Phe Ser Ala Leu
            35                  40                  45

Arg Thr Gly Trp Tyr Thr Ser Val Ile Thr Ile Glu Leu Ser Asn Ile
        50                  55                  60

Thr Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
```

-continued

```
                    85                  90                  95
Met Gln Asn Thr Pro Ala Ala Asn Asn Arg Ala Arg Arg Glu Ala Pro
                100                 105                 110

Gln His Met Asn Tyr Thr Ile Asn Thr Thr Lys Asn Leu Asn Val Ser
            115                 120                 125

Ile Ser Lys Lys Arg Lys Arg Arg Phe Leu Gly Phe Leu Leu Gly Val
        130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
                180                 185                 190

Leu Asp Leu Lys Asn Tyr Ile Asn Asn Gln Leu Leu Pro Ile Val Asn
            195                 200                 205

Gln Gln Ser Cys Arg Ile Phe Asn Ile Glu Thr Val Ile Glu Phe Gln
        210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
            370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
            450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510
```

Leu

<210> SEQ ID NO 3
<211> LENGTH: 552
<212> TYPE: PRT
<213> ORGANISM: Artificial Sequence
<220> FEATURE:
<223> OTHER INFORMATION: Synthetic construct

<400> SEQUENCE: 3

```
Met Glu Leu Leu Ile His Arg Ser Ser Ala Ile Phe Leu Thr Leu Ala
1               5                   10                  15

Ile Asn Ala Leu Tyr Leu Thr Ser Ser Gln Asn Ile Thr Glu Glu Phe
            20                  25                  30

Tyr Gln Ser Thr Cys Ser Ala Val Ser Arg Gly Tyr Phe Ser Ala Leu
        35                  40                  45

Arg Thr Gly Trp Tyr Thr Ser Val Ile Thr Ile Glu Leu Ser Asn Ile
    50                  55                  60

Thr Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln His Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Phe Asn Ile Glu Thr Val Ile Glu Phe Gln
    210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350
```

```
Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
    370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
                420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Leu Glu Gly
        450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
                500                 505                 510

Leu Ser Ala Ile Gly Gly Tyr Ile Pro Glu Ala Pro Arg Asp Gly Gln
            515                 520                 525

Ala Tyr Val Arg Lys Asp Gly Glu Trp Val Leu Leu Ser Thr Phe Leu
        530                 535                 540

Gly Gly Leu Val Pro Arg Gly Ser
545                 550

<210> SEQ ID NO 4
<211> LENGTH: 574
<212> TYPE: PRT
<213> ORGANISM: Artificial Sequence
<220> FEATURE:
<223> OTHER INFORMATION: Synthetic construct

<400> SEQUENCE: 4

Met Glu Leu Leu Ile His Arg Ser Ser Ala Ile Phe Leu Thr Leu Ala
1               5                   10                  15

Ile Asn Ala Leu Tyr Leu Thr Ser Ser Gln Asn Ile Thr Glu Glu Phe
            20                  25                  30

Tyr Gln Ser Thr Cys Ser Ala Val Ser Arg Gly Tyr Phe Ser Ala Leu
        35                  40                  45

Arg Thr Gly Trp Tyr Thr Ser Val Ile Thr Ile Glu Leu Ser Asn Ile
    50                  55                  60

Thr Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln His Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160
```

```
Glu Gly Glu Val Asn Lys Ile Lys Asn Ala Leu Leu Ser Thr Asn Lys
            165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
            195                 200                 205

Gln Gln Ser Cys Arg Ile Phe Asn Ile Glu Thr Val Ile Glu Phe Gln
            210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
            245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
            275                 280                 285

Met Ser Ile Ile Lys Glu Glu Val Leu Ala Tyr Val Val Gln Leu Pro
            290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
            325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
            355                 360                 365

Thr Met Asn Ser Leu Thr Leu Pro Ser Glu Val Ser Leu Cys Asn Thr
            370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Leu Glu Gly
            450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Lys Ser Asp Glu Leu
            500                 505                 510

Leu His Asn Val Asn Thr Gly Lys Ser Thr Thr Asn Ile Met Ile Thr
            515                 520                 525

Thr Ile Ile Ile Val Ile Ile Val Val Leu Leu Ser Leu Ile Ala Ile
            530                 535                 540

Gly Leu Leu Leu Tyr Cys Lys Ala Lys Asn Thr Pro Val Thr Leu Ser
545                 550                 555                 560

Lys Asp Gln Leu Ser Gly Ile Asn Asn Ile Ala Phe Ser Lys
            565                 570
```

```
<210> SEQ ID NO 5
<211> LENGTH: 552
<212> TYPE: PRT
<213> ORGANISM: Artificial Sequence
<220> FEATURE:
<223> OTHER INFORMATION: Synthetic construct

<400> SEQUENCE: 5

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Tyr Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
```

```
            370                 375                 380
Asp Ile Phe Asn Pro Lys Tyr Asp Cys Lys Ile Met Thr Ser Lys Thr
385                 390                 395                 400

Asp Val Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
                420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Val Asn Lys Gln Glu Gly
450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
                500                 505                 510

Leu Ser Ala Ile Gly Gly Tyr Ile Pro Glu Ala Pro Arg Asp Gly Gln
            515                 520                 525

Ala Tyr Val Arg Lys Asp Gly Glu Trp Val Leu Leu Ser Thr Phe Leu
            530                 535                 540

Gly Gly Leu Val Pro Arg Gly Ser
545                 550

<210> SEQ ID NO 6
<211> LENGTH: 552
<212> TYPE: PRT
<213> ORGANISM: Artificial Sequence
<220> FEATURE:
<223> OTHER INFORMATION: Synthetic construct

<400> SEQUENCE: 6

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
        50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
```

```
                180             185             190
Leu Asp Leu Lys Asn Tyr Ile Asp Lys Gln Leu Leu Pro Ile Leu Asn
            195                 200                 205
Lys Gln Ser Cys Ser Ile Ser Asn Ile Glu Thr Val Ile Glu Phe Gln
210                 215                 220
Gln Lys Asn Asn Arg Leu Glu Ile Thr Arg Glu Phe Ser Val Asn
225                 230                 235                 240
Ala Gly Val Thr Thr Pro Val Ser Thr Tyr Met Leu Thr Asn Ser Glu
                245                 250                 255
Leu Leu Ser Leu Ile Asn Asp Met Pro Ile Thr Asn Asp Gln Lys Lys
            260                 265                 270
Leu Met Ser Asn Asn Val Gln Ile Val Arg Gln Gln Ser Tyr Ser Ile
            275                 280                 285
Met Ser Ile Ile Lys Glu Val Leu Ala Tyr Val Val Gln Leu Pro
        290                 295                 300
Leu Tyr Gly Val Ile Asp Thr Pro Cys Trp Lys Leu His Thr Ser Pro
305                 310                 315                 320
Leu Cys Thr Thr Asn Thr Lys Glu Gly Ser Asn Ile Cys Leu Thr Arg
                325                 330                 335
Thr Asp Arg Gly Trp Tyr Cys Asp Asn Ala Gly Ser Val Ser Phe Phe
            340                 345                 350
Pro Gln Ala Glu Thr Cys Lys Val Gln Ser Asn Arg Val Phe Cys Asp
            355                 360                 365
Thr Met Asn Ser Leu Thr Leu Pro Ser Glu Val Asn Leu Cys Asn Val
        370                 375                 380
Asp Ile Phe Asn Pro Lys Tyr Asp Cys Lys Ile Met Thr Ser Lys Thr
385                 390                 395                 400
Asp Val Ser Ser Ser Val Ile Thr Ser Leu Gly Ala Ile Val Ser Cys
                405                 410                 415
Tyr Gly Lys Thr Lys Cys Thr Ala Ser Asn Lys Asn Arg Gly Ile Ile
            420                 425                 430
Lys Thr Phe Ser Asn Gly Cys Asp Tyr Val Ser Asn Lys Gly Val Asp
            435                 440                 445
Thr Val Ser Val Gly Asn Thr Leu Tyr Tyr Val Asn Lys Gln Glu Gly
        450                 455                 460
Lys Ser Leu Tyr Val Lys Gly Glu Pro Ile Ile Asn Phe Tyr Asp Pro
465                 470                 475                 480
Leu Val Phe Pro Ser Asp Glu Phe Asp Ala Ser Ile Ser Gln Val Asn
                485                 490                 495
Glu Lys Ile Asn Gln Ser Leu Ala Phe Ile Arg Lys Ser Asp Glu Leu
            500                 505                 510
Leu Ser Ala Ile Gly Gly Tyr Ile Pro Glu Ala Pro Arg Asp Gly Gln
            515                 520                 525
Ala Tyr Val Arg Lys Asp Gly Glu Trp Val Leu Leu Ser Thr Phe Leu
        530                 535                 540
Gly Gly Leu Val Pro Arg Gly Ser
545                 550

<210> SEQ ID NO 7
<211> LENGTH: 574
<212> TYPE: PRT
<213> ORGANISM: Artificial Sequence
<220> FEATURE:
<223> OTHER INFORMATION: Synthetic construct
```

<400> SEQUENCE: 7

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Cys Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415
```

```
Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Thr Gly Lys Ser Thr Thr Asn Ile Met Ile Thr
        515                 520                 525

Thr Ile Ile Ile Val Ile Ile Val Val Leu Leu Ser Leu Ile Ala Ile
    530                 535                 540

Gly Leu Leu Leu Tyr Cys Lys Ala Lys Asn Thr Pro Val Thr Leu Ser
545                 550                 555                 560

Lys Asp Gln Leu Ser Gly Ile Asn Asn Ile Ala Phe Ser Lys
                565                 570
```

<210> SEQ ID NO 8
<211> LENGTH: 552
<212> TYPE: PRT
<213> ORGANISM: Artificial Sequence
<220> FEATURE:
<223> OTHER INFORMATION: Synthetic construct

<400> SEQUENCE: 8

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Cys Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asp Lys Gln Leu Leu Pro Ile Leu Asn
        195                 200                 205
```

Lys Gln Ser Cys Ser Ile Ser Asn Ile Glu Thr Val Ile Glu Phe Gln
            210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Cys Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu Ser Ala Ile Gly Gly Tyr Ile Pro Glu Ala Pro Arg Asp Gly Gln
        515                 520                 525

Ala Tyr Val Arg Lys Asp Gly Glu Trp Val Leu Leu Ser Thr Phe Leu
    530                 535                 540

Gly Gly Leu Val Pro Arg Gly Ser
545                 550

<210> SEQ ID NO 9
<211> LENGTH: 574
<212> TYPE: PRT
<213> ORGANISM: Artificial Sequence
<220> FEATURE:
<223> OTHER INFORMATION: Synthetic construct

<400> SEQUENCE: 9

Met Glu Leu Leu Ile Leu Lys Ala Asn Ala Ile Thr Thr Ile Leu Thr
1               5                   10                  15

```
Ala Val Thr Phe Cys Phe Ala Ser Gly Gln Asn Ile Thr Glu Glu Phe
         20                  25                  30

Tyr Gln Ser Thr Cys Ser Ala Val Ser Lys Gly Tyr Leu Ser Ala Leu
         35                  40                  45

Arg Thr Gly Trp Tyr Thr Ser Val Ile Thr Ile Glu Leu Ser Asn Ile
 50                      55                  60

Lys Glu Asn Lys Cys Asn Gly Thr Asp Ala Lys Val Lys Leu Ile Lys
 65                  70                  75                  80

Gln Glu Leu Asp Lys Tyr Lys Asn Ala Val Thr Glu Leu Gln Leu Leu
                 85                  90                  95

Met Gln Ser Thr Pro Ala Thr Asn Asn Arg Ala Arg Arg Glu Leu Pro
             100                 105                 110

Arg Phe Met Asn Tyr Thr Leu Asn Asn Ala Lys Lys Thr Asn Val Thr
         115                 120                 125

Leu Ser Lys Lys Arg Lys Arg Arg Phe Leu Gly Phe Leu Leu Gly Val
 130                 135                 140

Gly Ser Ala Ile Ala Ser Gly Val Ala Val Cys Lys Val Leu His Leu
 145                 150                 155                 160

Glu Gly Glu Val Asn Lys Ile Lys Ser Ala Leu Leu Ser Thr Asn Lys
                 165                 170                 175

Ala Val Val Ser Leu Ser Asn Gly Val Ser Val Leu Thr Ser Lys Val
             180                 185                 190

Leu Asp Leu Lys Asn Tyr Ile Asp Lys Gln Leu Leu Pro Ile Val Asn
         195                 200                 205

Lys Gln Ser Cys Ser Ile Ser Asn Ile Glu Thr Val Ile Glu Phe Gln
 210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
             245                 250                 255

Leu Leu Ser Leu Ile Asn Asp Met Pro Ile Thr Asn Asp Gln Lys Lys
         260                 265                 270

Leu Met Ser Asn Asn Val Gln Ile Val Arg Gln Gln Ser Tyr Ser Ile
         275                 280                 285

Met Cys Ile Ile Lys Glu Glu Val Leu Ala Tyr Val Val Gln Leu Pro
 290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
             325                 330                 335

Thr Asp Arg Gly Trp Tyr Cys Asp Asn Ala Gly Ser Val Ser Phe Phe
         340                 345                 350

Pro Gln Ala Glu Thr Cys Lys Val Gln Ser Asn Arg Val Phe Cys Asp
         355                 360                 365

Thr Met Asn Ser Leu Thr Leu Pro Ser Glu Val Asn Leu Cys Asn Val
 370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
             405                 410                 415

Tyr Gly Lys Thr Lys Cys Thr Ala Ser Asn Lys Asn Arg Gly Ile Ile
         420                 425                 430
```

-continued

```
Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Thr Gly Lys Ser Thr Thr Asn Ile Met Ile Thr
    515                 520                 525

Thr Ile Ile Ile Val Ile Ile Val Val Leu Leu Ser Leu Ile Ala Ile
    530                 535                 540

Gly Leu Leu Leu Tyr Cys Lys Ala Lys Asn Thr Pro Val Thr Leu Ser
545                 550                 555                 560

Lys Asp Gln Leu Ser Gly Ile Asn Asn Ile Ala Phe Ser Lys
                565                 570
```

COMPOSITIONS AND METHODS FOR VACCINATION AGAINST RESPIRATORY SYNCYTIAL VIRUS INFECTION

FIELD

The disclosure generally relates to vaccination against an infectious disease, particularly against respiratory syncytial virus (RSV). The disclosure includes various compositions and methods for vaccination, including maternal vaccination to protect both mother and offspring from RSV infection.

BACKGROUND

Respiratory syncytial virus (RSV) is estimated to cause 30 million acute respiratory tract infections each year, resulting in an estimated 3.2 million annual hospitalizations worldwide and approximately 60,000 in-hospital deaths in children less than 5 years old (Shi et al., Lancet, 2017; 390 (10098):946-58; Jha et al, Wellcome Trust-Funded Monographs and Book Chapters, Sheffield UK2016). Children less than 6 months of age account for nearly 50% of all RSV-related hospital admissions and in-hospital deaths (Shi et al., Lancet, 2017; 390(10098):946-58), highlighting the need for a vaccine able to provide RSV protection early in life. Given the strong association between severe RSV infection during infancy and the subsequent development of asthma and impaired lung function, prevention of acute, RSV-related disease may also have long-term beneficial effects (Zomer-Kooijker et al., PLoS One, 2014; 9(1): e87162; Feldman et al., Am. J. Respir. Crit. Care Med., 2015; 191(1):34-44).

The development of an effective RSV vaccine has been hampered by neonatal immune immaturity (PrabhuDas et al., Nat. Immunol., 2011; 12(3):189-94), the short time frame between birth and first RSV exposure, and the risk of vaccine-enhanced disease (VERD) in infants that was first identified in the late 1960s when a formalin-inactivated, alum-adjuvanted RSV (FI-RSV) vaccine resulted in the death of two children (Acosta et al., Clin. Vaccine Immunol., 2015; 23(3):189-95; Kim et al., Am. J. Epidemiol., 1969; 89(4):422-34). Analyses of lung sections from these children along with additional preclinical studies suggested that the FI-RSV-associated VERD was due to a combination of poorly neutralizing antibodies and excess Th2 priming of the infants' immune systems following natural RSV infection (Delgado et al., Nat. Med., 2009; 15(1):34-41; Graham, Curr. Opin. Virol., 2017; 23:107-12; Killikelly et al., Sci. Rep., 2016; 6:34108; Polack et al., J. Exp. Med., 2002; 196(6):859-65). Lack of VERD in older children called into question whether prior infection with live virus may protect children from VERD (Anderson et al., J. Infect. Dis., 1995; 171(1):1-7). This idea was corroborated in pre-clinical studies whereby seropositive cotton rats did not develop VERD when vaccinated with FI-RSV and then challenged with RSV (Blanco et al., Vaccine, 2017; 35(32):3951-8; Waris et al., J. Virol., 1997; 71(9):6935-9). Though not completely understood, animal studies suggest that prior infection with live virus primes the immune system and prevents the disease-enhancing memory immune response associated with FI-RSV (Waris et al., J. Virol., 1997; 71(9):6935-9). Since this time, studies focused on vaccination strategies that would generate potent neutralizing antibodies without causing Th2-biased immunity. The RSV fusion (RSV F) glycoprotein, which mediates viral entry into host cells, is the primary target of neutralizing antibodies in human sera (Sastre et al., J. Med. Virol., 2005; 76(4248-55). RSV F rapidly rearranges from a pre-fusion to a postfusion conformation, with the former inducing more potent neutralizing antibodies (Killikelly et al., Sci. Rep., 2016; 6:34108; McLellan et al., Science, 2013; 342(6158):592). Stabilized forms of pre-fusion RSV F protein such as, DS-Cav1, are more representative of live RSV (Killikelly et al., Sci. Rep., 2016; 6:34108) and can induce high neutralizing antibody titers when combined with an appropriate adjuvant (McLellan et al., Science, 2013; 342(6158):592).

A clinical study designed to evaluate the safety and immunogenicity of an adenovirus-based RSV prefusion vaccine will soon start recruiting toddlers aged 12 to 24 months of age (B. V. JVP. NCT03606512: US National Library of Medicine; 2019). However, in the absence of an adjuvant, studies reported that RSV prefusion immunogens fails to generate protective levels of neutralizing antibody (Sastry et al., PLoS One, 2017; 12(10):e0186854; Schneider-Ohrum et al., J. Virol., 2017; 91(8)). Aluminum salts are the most widely used vaccine adjuvants because their Th2 immune bias makes them highly effective at increasing antibody titers (De Gregorio et al., Eur. J. Immunol., 2008; 38(8):2068-71; Sastry et al., PLOS ONE, 2017; 12(10): e0186854; Wang et al., J. Biol. Chem., 2012; 287(21): 17152-60). However, investigations into the causes of VERD in FI-RSV-vaccinated children have consistently demonstrated the contribution of Th2-mediated pathology (Castilow et al., J. Immunol., 2008; 180(4):2376; Connors et al., J. Virol., 1992; 66(12):7444-51; Johnson et al., J. Leukocyte Biol., 2008; 84(3):748-59; Knudson et al., PLOS Pathog., 2015; 11(3):e1004757). Pre-clinical mouse models further demonstrated that when combined with DS-Cav1, alum promoted a strong Th2 response following RSV infection in naïve mice vaccinated with DS-Cav1 (Sastry et al., PLoS One, 2017; 12(10):e0186854).

Another challenge to overcoming severe RSV disease in infants is the early age at which severe infection occurs. In maternal vaccination, pregnant mothers are vaccinated to bolster their neutralizing antibody response along with the passive transfer of antibody to their children. Maternally-derived antibodies can protect infants from infection as their own immune systems mature and expand, yet infants often develop severe RSV disease in the first months of life, suggesting that maternal-to-infant anti-RSV antibody transfer is often inadequate and likely varies from one individual to another based on their RSV exposure history. Immunizing mothers during pregnancy may permit the passive transfer of high levels of RSV neutralizing antibodies from mothers to their offspring. Despite ongoing clinical trials in pregnant women, questions remain as to the type of immune response and possible risk of enhanced RSV disease in children born to vaccinated mothers if they are to become infected for the first time as maternal antibody is waning.

In a recent study by Schneider-Ohrum, investigators reported that when vaccinated with de-escalating doses of RSV F immunogens, adult BALB/c mice experienced an enhanced form of RSV disease following viral infection similar in severity to that of mice vaccinated with FI-RSV. Earlier studies performed in cotton rats also reported enhanced pulmonary histopathology following vaccination with RSV F protein when challenged with RSV several months after immunization (Murphy et al., Vaccine, 1990; 8(5):497-502). Though Th2-driven immunity should not be transferred to the offspring of vaccinated dams with poorly neutralizing antibody, it remains unclear whether infants born to vaccinated dams will experience an enhanced form of RSV disease if primary infection occurs later when the child's immune response is more robust, but maternal antibody is low or waning.

The compositions and methods disclosed herein address these and other needs.

SUMMARY

The present disclosure relates to vaccination against respiratory syncytial virus (RSV). The disclosed novel combination of components increases both anti-RSV protection and vaccine safety in mothers and offspring born thereto. Maternal vaccination significantly reduces RSV infection, elicits desirable cellular and immunological responses, and reduces vaccine complications such as vaccine-enhanced respiratory disease (VERD) and eosinophilia.

In some aspects, disclosed herein are compositions for vaccination against respiratory syncytial virus (RSV) comprising an RSV F polypeptide stabilized in a prefusion conformation and an inulin adjuvant. In some embodiments, the RSV F polypeptide comprises a pre-fusion-stabilized trimeric polypeptide, for example by inclusion of a trimerization domain. In some embodiments, the RSV F polypeptide comprises a mutation that fills a space within a cavity in a RSV F polypeptide or between RSV F polypeptides. In some embodiments, the RSV F polypeptide comprises a non-natural disulfide bond. In some embodiments, the RSV F polypeptide comprises a dityrosine bond. In some embodiments, the inulin comprises a polyfructofuranosyl-D-glucose inulin. In some embodiments, the inulin comprises an Advax adjuvant, for instance, Advax. In other embodiments, additional adjuvants are used with inulin such as CpG oligonucleotide(s). The disclosed compositions can be formulated in vaccines. Thus, also disclosed are vaccine formulations comprising a RSV F polypeptide stabilized in a prefusion conformation and an inulin adjuvant and a pharmaceutically acceptable carrier.

In some aspects, provided herein are methods of vaccinating a subject against a respiratory syncytial virus (RSV) infection comprising administering to the subject an RSV F polypeptide stabilized in a prefusion conformation and an inulin adjuvant. In some embodiments, the RSV F polypeptide and the inulin adjuvant are each administered within a 24-hour period. In some embodiments, the RSV F polypeptide and the inulin adjuvant are administered together in a vaccine formulation comprising a pharmaceutically acceptable carrier. In some embodiments, the subject is a female. In some embodiments, the female is pregnant with an offspring. In some embodiments, there is an administration to the subject before pregnancy and during pregnancy. In some embodiments, the method reduces the RSV infection in the subject or an offspring of the subject as compared to a control. In some embodiments, the method decreases a vaccine-enhanced respiratory disease (VERD) in the dams as compared to a control. In other or further embodiments, the method decreases VERD in the offspring as compared to a control. In some embodiments, the method decreases eosinophilia in the subject or offspring as compared to a control. In some embodiments, the administration of the adjuvant increases a ratio of Th1:Th2 cell responses in the subject as compared to a control.

Additional aspects and advantages of the disclosure will be set forth, in part, in the detailed description and any claims which follow, and in part will be derived from the detailed description or can be learned by practice of the various aspects of the disclosure. The advantages described below will be realized and attained by means of the elements and combinations particularly pointed out in the appended claims. It is to be understood that both the foregoing general description and the following detailed description are for purposes of example, are explanatory only, and are not restrictive of the disclosure.

BRIEF DESCRIPTION OF THE DRAWINGS

The accompanying drawings, which are incorporated in and constitute a part of this specification, illustrate certain examples of the present disclosure and together with the description, serve to explain, without limitation, the principles of the disclosure. Like numbers represent the same element(s) throughout the figures.

Unless indicated otherwise, the following relates to all figures: $*p<0.05$, $p<0.01$, $*p<0.001$, $****p<0.0001$ as compared to PBS controls and $\#p<0.05$; $\#\#\#p<0.001$ between DSCav1 and DSCav1/Advax. The term "HI" expressed as a superscript at the end of a protein or gene name refers to high expression of that gene/protein compared to average expression levels in a population. The term "LOW" expressed as a superscript at the end of a protein or gene name refers to low expression of that gene/protein compared to average expression levels in a population.

FIG. 1(A-C) are graphs showing protective immunity in the lungs of DS-Cav1+Advax-SM immunized dams following RSV challenge. 7-8 week old female BALB/cJ mice were immunized at the time of co-housing (Day 0; "D0") and again 2 weeks after breeding, in the second week of gestation (D21). Vaccine formulations were as follows: PBS—vehicle control, DS-Cav1 alone, DS-Cav1+Advax-SM. Dams gave birth (D28) and nursed their offspring for 21 days until weaning (D49). Four days after their pups were weaned, dams were subjected to an intranasal (i. n.) challenge with RSV L19 (D53). Pre-challenge serum was collected immediately prior to RSV challenge for 1/PRNT50 levels (see Table 1). Weights were recorded daily and comparisons between immunization groups were made using repeated measures ANOVA with a Bonferroni post-test where * indicates $\rho<0.05$ between DS-Cav1 and DS-Cav1+Advax-SM (FIG. 1A). At 4 dpi, dams were culled and tissues collected for analysis (D57). Left lungs were harvested and processed for viral quantification using H&E plaque assays (FIG. 1B). Viral titers were performed in triplicate and individual symbols within each group represent the mean titer for each animal, lines represent the mean of n≥11 animals per group±SEM. Viral titers were compared between groups using ANOVA with a Tukey post-test; $***\rho<0.001$. Lungs with no detectable virus were considered sterile and percentages of sterile lungs were calculated for each vaccine formulation (FIG. 1B). In FIG. 1C, 1/PRNT50 titers at 4 dpi are shown on the y-axis and are represented by open symbols and compared to viral lung titers (z-axis) represented by closed symbols. Results are representative of 2 independent experiments.

Figure 12:
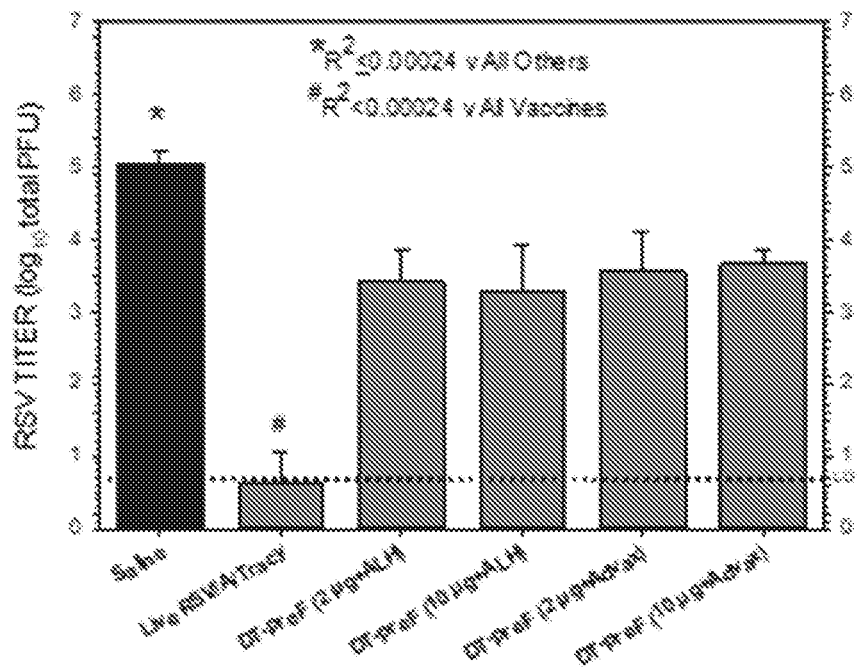

FIG. 12 is a graph showing the RSV nasal wash titers at day 39 after challenging immunized dams with RSV/A/Tracy virus. The dams were immunized with saline, DT-PreF and ALH (Alhydrogel), or DT-preF and Advax. * indicates $R^2 \leq 0.00024$ versus all others. # indicates $R^2 < 0.00024$ vs all vaccines.

Figure 13:
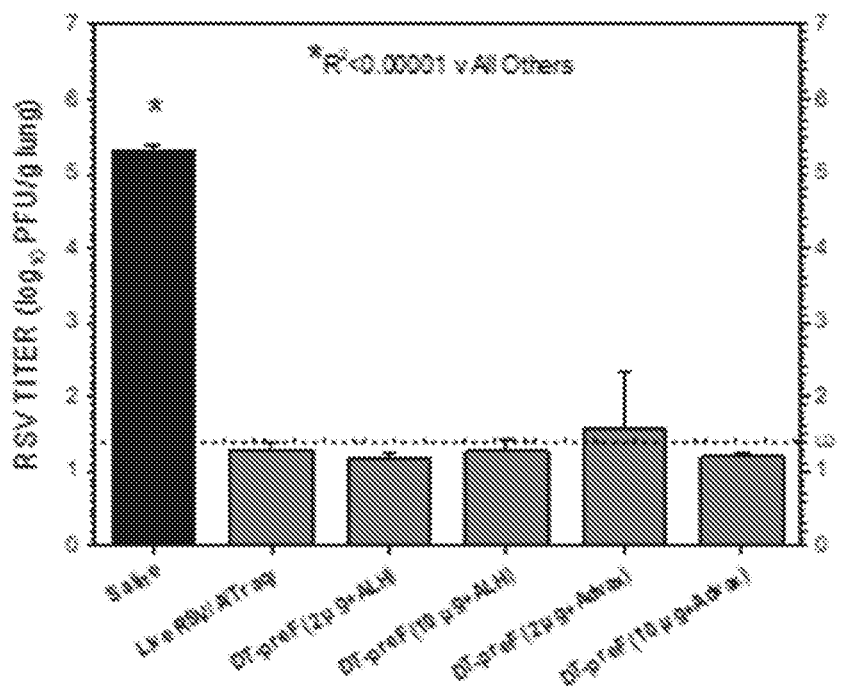

FIG. 13 is a graph showing the RSV lung lavage titers at day 39 after challenging immunized dams with RSV/A/Tracy virus. The dams were immunized with saline, virus alone, DT-PreF and ALAI (Alhydrogel), or DT-preF and Advax. * indicates $R^2 < 0.00001$ vs all others.

Figure 14:
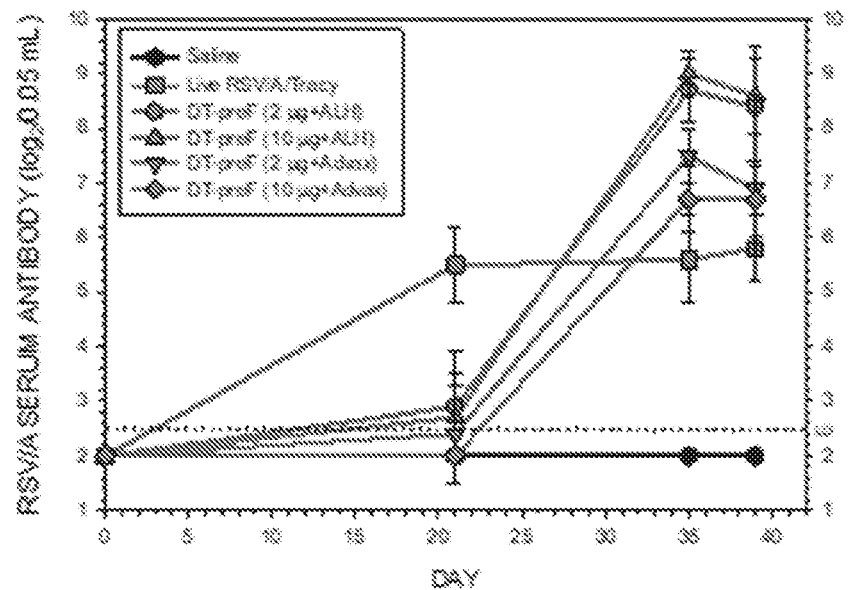

FIG. 14 is a graph showing the RSV/A serum neutralizing titers after challenging immunized dams with RSV/A/Tracy virus. The dams were immunized with saline (dark filled circle), virus alone (square), DT-PreF and ALE (Alhydrogel) (circle (2 µg DT-preF) and dark filled upright triangle (10 µg DT-preF)), or DT-preF and Advax (dark filled downward triangle (2 µg DT-preF) dark filled diamond (10 µg DT-preF)).

Figure 15:
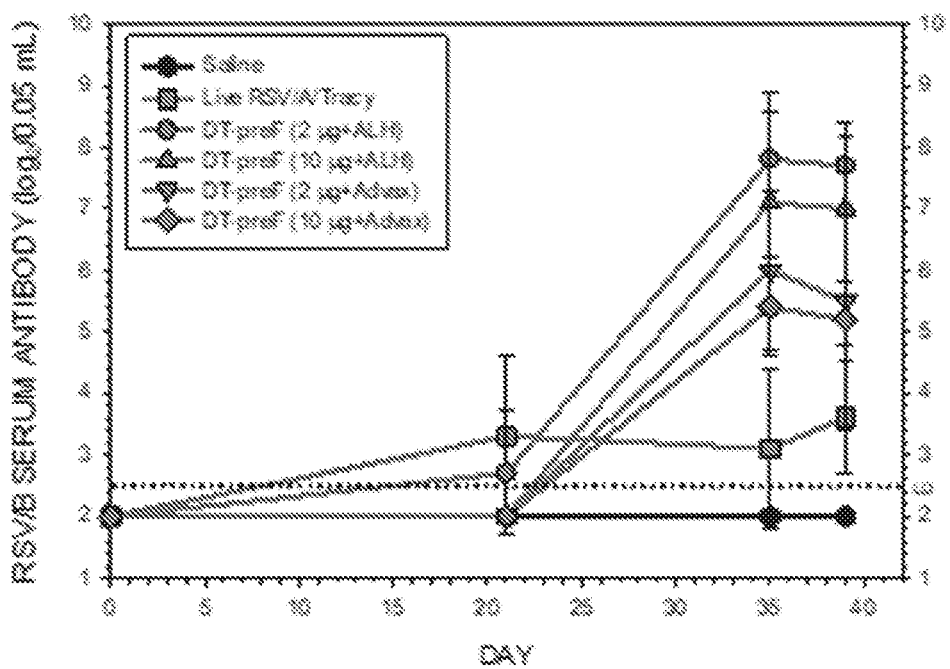

FIG. 15 is a graph showing the RSV/B serum neutralizing titers after challenging immunized dams with RSV/A/Tracy virus. The dams were immunized with saline (dark filled circle), virus alone (square), DT-PreF and ALH (Alhydrogel) (circle (2 µg DT-pref) and dark filled upright triangle (10 µg DT-preF)), or DT-preF and Advax (dark filled downward triangle (2 µg DT-preF) dark filled diamond (10 µg DT-preF)).

Figure 16:
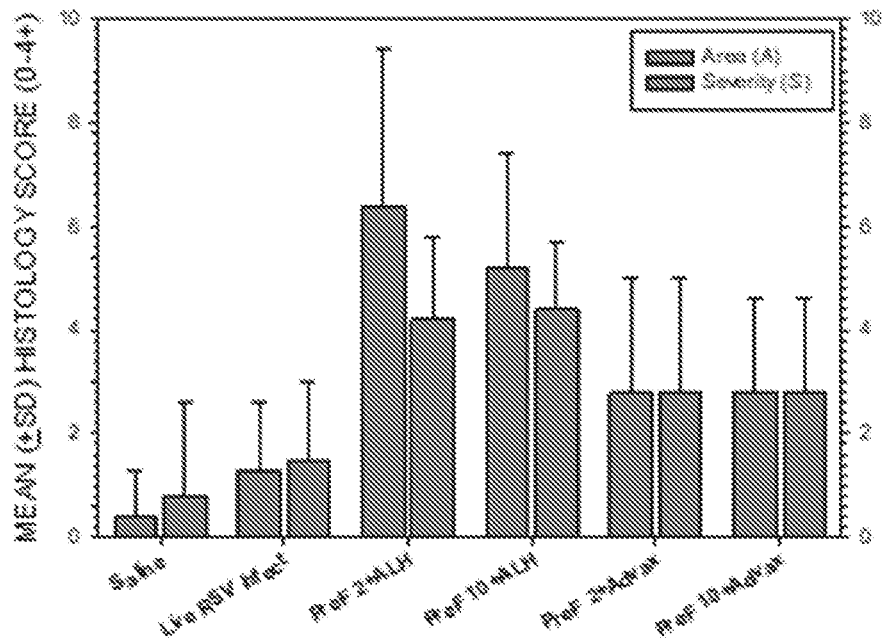

FIG. 16 is a is a graph summarizing the histopathology scores obtained from the experiments described in FIGS. 12-15; each of the bars on the left representing area and each of the bars on the right representing severity.

Figure 17:
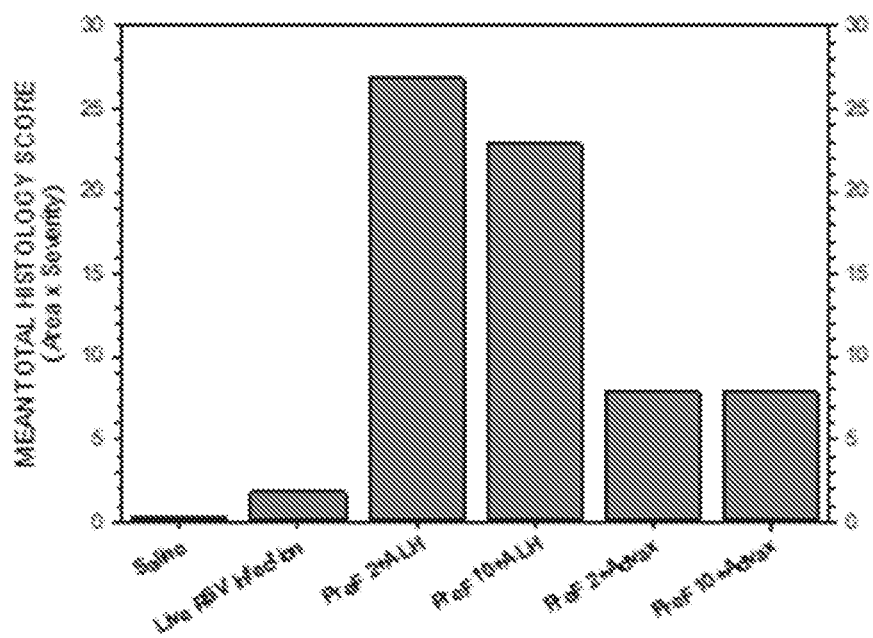

FIG. 17 is a graph summarizing the total group histopathology scores (Area×Severity) obtained from the experiments described in FIGS. 12-15.

DETAILED DESCRIPTION

The following description of the disclosure is provided as an enabling teaching of the disclosure in its best, currently known embodiment(s). To this end, those skilled in the relevant art will recognize and appreciate that many changes can be made to the various embodiments of the invention described herein, while still obtaining the beneficial results of the present disclosure. It will also be apparent that some of the desired benefits of the present disclosure can be obtained by selecting some of the features of the present disclosure without utilizing other features. Accordingly, those who work in the art will recognize that many modifications and adaptations to the present disclosure are possible and can even be desirable in certain circumstances and are a part of the present disclosure. Thus, the following description is provided as illustrative of the principles of the present disclosure and not in limitation thereof.

Terminology

Unless defined otherwise, all technical and scientific terms used herein have the same meaning as commonly understood to one of ordinary skill in the art to which this invention belongs. The following definitions are provided for the full understanding of terms used in this specification.

The term "comprising" and variations thereof as used herein is used synonymously with the terms "including," "containing," and variations thereof and are open, non-limiting terms. Although the terms "comprising," "including," and "containing" have been used herein to describe various embodiments, the terms "consisting essentially of" and "consisting of" can be used in place of "comprising," "including," and "containing" to provide for more specific embodiments and are also disclosed.

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular component is disclosed and discussed and a number of modifications that can be made to the component are discussed, specifically contemplated is each and every combination and permutation of the component and the modifications that are possible unless specifically indicated to the contrary. Thus, if a class of components A, B, and C are disclosed as well as a class of components D, E, and F and an example of a combination component, or, for example, a combination component comprising A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

It is understood that the compositions disclosed herein have certain functions. Disclosed herein are certain structural requirements for performing the disclosed functions, and it is understood that there are a variety of structures which can perform the same function which are related to the disclosed structures, and that these structures will ultimately achieve the same result.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

As used in the specification and claims, the singular form "a," "an," and "the" include plural references unless the context clearly dictates otherwise. For example, the term "an agent" includes a plurality of agents, including mixtures thereof.

As used herein, the terms "may," "optionally," and "may optionally" are used interchangeably and are meant to include cases in which the condition occurs as well as cases in which the condition does not occur. Thus, for example, the statement that a formulation "may include an excipient" is meant to include cases in which the formulation includes an excipient as well as cases in which the formulation does not include an excipient.

The terms "about" and "approximately" are defined as being "close to" as understood by one of ordinary skill in the art. In some non-limiting embodiments, the terms are defined to be within 10% of the associated value provided. In some non-limiting embodiments, the terms are defined to be within 5%. In still other non-limiting embodiments, the terms are defined to be within 1%.

"Administration" to a subject includes any route of introducing or delivering to a subject an agent. Administration can be carried out by any suitable route, including oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation, via an implanted reservoir, parenteral (e.g., subcutaneous, intravenous, intramuscular, intra-articular, intra-synovial, intrasternal, intrathecal, intraperitoneal, intrahepatic, intralesional, and intracranial injections or infusion techniques), and the like. "Concurrent administration", "administration in combination", "simultaneous administration" or "administered simultaneously" as used herein, means that the compounds are administered at about the same point in time, overlapping in time, or one following the other. In the latter case, the two compounds are administered at times sufficiently close that the results observed are indistinguishable from those achieved when the compounds are administered at the same point in time. "Systemic administration" refers to the introducing or delivering to a subject an agent via a route which introduces or delivers the agent to extensive areas of the subject's body (e.g. greater than 50% of the body), for example through entrance into the circulatory or lymph systems. By contrast, "local administration" refers to the introducing or delivery to a subject an agent via a route which introduces or delivers the agent to the area or area immediately adjacent to the point of administration and does not introduce the agent systemically in a therapeutically significant amount. For example, locally administered agents are easily detectable in the local vicinity of the point of administration, but are undetectable or detectable at negligible amounts in distal parts of the subject's body. Administration includes self-administration and the administration by another.

"Effective amount" of an agent refers to a sufficient amount of an agent to provide a desired effect. The amount of agent that is "effective" will vary from subject to subject, depending on many factors such as the age and general condition of the subject, the particular agent or agents, and the like. Thus, it is not always possible to specify a quantified "effective amount." However, an appropriate "effective amount" in any subject case may be determined by one of ordinary skill in the art using routine experimentation. Also, as used herein, and unless specifically stated otherwise, an "effective amount" of an agent can also refer to an amount covering either or both a therapeutically effective amount and a prophylactically effective amount. An "effective amount" of an agent necessary to achieve a therapeutic effect may vary according to factors such as the age, sex, and weight of the subject. Dosage regimens can be adjusted to provide the optimum therapeutic response. For example, several divided doses may be administered daily or the dose may be proportionally reduced as indicated by the exigencies of the therapeutic situation.

"Identical" or percent "identity," in the context of two or more nucleic acids or polypeptide sequences, refer to two or more sequences or subsequences that are the same or have a specified percentage of amino acid residues or nucleotides that are the same (e.g., about 60% identity, preferably 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%,94%, 95%, 96%, 97%, 98%, 99% or higher identity over a specified region when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the complement of a test sequence. The definition also includes sequences that have deletions and/or additions, as well as those that have substitutions. As described below, the preferred algorithms can account for gaps and the like. Preferably, identity exists over a region that is at least about 10 amino acids or 20 nucleotides in length, or more preferably over a region that is 10-50 amino acids or 20-50 nucleotides in length. As used herein, percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

One example of an algorithm that is suitable for determining percent sequence identity and sequence similarity are the BLAST and BLAST 2.0 algorithms, which are described in Altschul et al. (1977) Nuc. Acids Res. 25:3389-3402, and Altschul et al. (1990) J. Mol. Biol. 215:403-410, respectively. Software for performing BLAST analyses is publicly available through the National Center for Biotechnology Information (http://www.ncbi.nlm nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. (1990) J. Mol. Biol. 215:403-410). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues;

always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) or 10, M=5, N=−4 and a comparison of both strands. For amino acid sequences, the BLASTP program uses as defaults a word length of 3, and expectation (E) of 10, and the BLOSUM62 scoring matrix (see Henikoff and Henikoff (1989) Proc. Natl. Acad. Sci. USA 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) Proc. Natl. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01.

"Pharmaceutically acceptable" component can refer to a component that is not biologically or otherwise undesirable, e.g., the component may be incorporated into a pharmaceutical formulation of the invention and administered to a subject as described herein without causing significant undesirable biological effects or interacting in a deleterious manner with any of the other components of the formulation in which it is contained. When used in reference to administration to a human, the term generally implies the component has met the required standards of toxicological and manufacturing testing or that it is included on the Inactive Ingredient Guide prepared by the U.S. Food and Drug Administration.

The term "pharmaceutically effective amount" refers to the amount of a compound such as an RSV F polypeptide and inulin adjuvant that will elicit the biological or medical response of a tissue, system, animal, or human that is being sought by the researcher, veterinarian, medical doctor or other clinician. In some embodiments, a desired response is a prophylactic immune response to RSV. In some instances, a desired biological or medical response is achieved following administration of multiple dosages of the RSV F polypeptide and inulin adjuvant composition to the subject over a period of days, weeks, or years. The term "pharmaceutically effective amount includes that amount of a compound such as a selective bacterial β-glucuronidase inhibitor that, when administered, is sufficient to prevent development of, or alleviate to some extent, one or more of the symptoms of the condition or disorder being treated or prevented. The therapeutically effective amount will vary depending on the compound such as the RSV F polypeptide and inulin adjuvant, the disorder or conditions and its severity, the route of administration, time of administration, rate of excretion, drug combination, judgment of the treating physician, dosage form, and the age, weight, general health, sex and/or diet of the subject to be treated. In the context of the present method, a pharmaceutically effective amount or dose of a RSV F polypeptide and inulin adjuvant includes an amount that is sufficient to prevent or reduce the severity of an RSV infection in a subject as compared to a control.

"Pharmaceutically acceptable carrier" (sometimes referred to as a "carrier") means a carrier or excipient that is useful in preparing a pharmaceutical or therapeutic composition that is generally safe and non-toxic, and includes a carrier that is acceptable for veterinary and/or human pharmaceutical or therapeutic use. The terms "carrier" or "pharmaceutically acceptable carrier" can include, but are not limited to, phosphate buffered saline solution, water, emulsions (such as an oil/water or water/oil emulsion) and/or various types of wetting agents. As used herein, the term "carrier" encompasses, but is not limited to, any excipient, diluent, filler, salt, buffer, stabilizer, solubilizer, lipid, stabilizer, or other material well known in the art for use in pharmaceutical formulations and as described further herein.

"Polypeptide" is used in its broadest sense to refer to a compound of two or more subunit amino acids, amino acid analogs, or peptidomimetics. The subunits may be linked by peptide bonds. In another embodiment, the subunit may be linked by other bonds, e.g. ester, ether, etc. As used herein the term "amino acid" refers to either natural and/or unnatural or synthetic amino acids, including glycine and both the D or L optical isomers, and amino acid analogs and peptidomimetics.

The term "vaccine" as used herein refers to a composition comprising an RSV F polypeptide as described herein, which is useful to increase a protective immune response to RSV in a subject. It is contemplated that the vaccine comprises a pharmaceutically acceptable carrier and/or an adjuvant. It is contemplated that vaccines are prophylactic or therapeutic.

A "prophylactic" treatment is a treatment administered to a subject who does not exhibit signs of a disease or exhibits only early signs for the purpose of decreasing the risk of developing pathology. The vaccines disclosed herein can be given as a prophylactic treatment to reduce the likelihood of developing a pathology or to minimize the severity of the pathology, if developed.

"Specifically binds" when referring to a polypeptide (including antibodies) or receptor, refers to a binding reaction which is determinative of the presence of the protein or polypeptide or receptor in a heterogeneous population of proteins and other biologics. Thus, under designated conditions (e.g. immunoassay conditions in the case of an antibody), a specified ligand or antibody "specifically binds" to its particular "target" (e.g. an antibody specifically binds to an endothelial antigen) when it does not bind in a significant amount to other proteins present in the sample or to other proteins to which the ligand or antibody may come in contact in an organism. Generally, a first molecule that "specifically binds" a second molecule has an affinity constant (Ka) greater than about $10^5$ $M^{-1}$ (e.g., $10^6$ $M^{-1}$, $10^7$ $M^{-1}$, $10^8$ $M^{-1}$, $10^9$ $M^{-1}$, $10^{10}$ $M^{-1}$, $10^{11}$ $M^{-1}$, and $10^{12}$ $M^{-1}$ or more) with that second molecule.

A "therapeutic" treatment is a treatment administered to a subject who exhibits signs or symptoms of pathology for the purpose of diminishing or eliminating those signs or symptoms. The signs or symptoms may be biochemical, cellular, histological, functional, subjective or objective.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed.

Compositions

It is understood that the composition for vaccination of the present disclosure can be used in combination with the various compositions, methods, products, and applications disclosed herein.

In one aspect, disclosed herein are compositions for vaccination against respiratory syncytial virus (RSV) comprising a RSV F polypeptide stabilized in a prefusion conformation and an inulin adjuvant. The disclosed compositions for vaccination against RSV comprise a novel combination of components which increases both protection against RSV and safety of the vaccine in mothers and offspring. Maternal vaccination significantly reduces RSV titers in mothers, newborn infants, and mature offspring (e.g., weanlings) in part by eliciting desirable cellular and immunological responses in vaccinated mothers, stimulating approximately ten-fold greater or more neutralizing capacity compared to standard postfusion antigens, and reducing interference of infant antibody activity by competing maternal antibodies. Maternal vaccination using the disclosed vaccine compositions also significantly reduces complications such as eosinophilia (for example, in mothers), VERD (for example, in offspring), or other lung immunopathologies. As such, the vaccination compositions and methods disclosed herein represent novel vaccine approaches which overcome significant barriers associated with direct infant vaccination.

The herein disclosed compositions are effective for vaccination against RSV. It was a surprising result that the combined RSV F polypeptide stabilized in a prefusion conformation and the inulin adjuvant provided robust immunological responses and significant reduction in RSV infection, and can further reduce or avoid lung pathologies such as vaccine enhanced respiratory disease. It is established herein that the disclosed RSV F polypeptide and the inulin adjuvant function synergistically to reduce RSV infection in vaccinated subjects and offspring born thereto.

The compositions for vaccination against respiratory syncytial virus (RSV) comprise a RSV F polypeptide stabilized in a prefusion conformation and an inulin adjuvant. The RSV F protein, or fusion protein, is an envelope polypeptide of RSV viruses. A homotrimer of RSV F proteins mediates fusion of viral and cellular membranes during RSV infection, and is a target for vaccination against RSV infection. The RSV F polypeptide described herein can be derived from any RSV subtype (e.g., subtypes A or B) or from any isolate which is a clinical, laboratory/engineered, non-virulent, or non-infectious isolate. Wild-type F polypeptide from a RSV subtype A virus can comprise an amino acid sequence of SEQ ID NO:1, and wild-type F polypeptide from a RSV subtype B virus can comprise an amino acid sequence of SEQ ID NO:2. One of skill in the art appreciates that wild-type sequences are merely one of many possible consensus sequences, and any given wild-type or engineered RSV particle can contain a F polypeptide having an amino acid sequence different from SEQ ID NO:1 and SEQ ID NO:2.

The RSV F protein exists in at least two conformers: a prefusion and a postfusion conformation. Upon binding of the virus to a host cell, the F-protein undergoes a conformational change from a prefusion to a postfusion conformation. Prefusion F-protein is the primary determinant of neutralizing activity against RSV in human sera, but soluble prefusion F-protein is highly unstable and readily converts to a postfusion conformation. Accordingly, included herein are RSV F polypeptides which are stabilized in a pre-fusion conformation. The three-dimensional structure of an example RSV F protein in a prefusion conformation is disclosed in U.S. Patent Application Publication US20160046675.

As used herein, the term "RSV F polypeptide stabilized in a prefusion conformation" includes any synthetic or engineered Fusion (F) polypeptide from a respiratory syncytial virus stabilized in one or more prefusion conformations, including any such polypeptide described in U.S. Patent Application Publications US20150030622 and US20160046675, both of which are incorporated herein by reference in their entireties. In some embodiments, the RSV F polypeptide stabilized in a prefusion conformation is in a soluble form.

The term "stabilized" as it refers to a prefusion conformation of a RSV F polypeptide, refers to an increased stability of a prefusion conformation resulting from a modification, as compared to the stability of the prefusion conformation without the modification. Absolute stability is expressly not required; rather the modification introduces an increased degree of stability in a prefusion conformation. Stability, and relative stability, may be measured in various ways, for example by measuring the half-life of the RSV pre-fusion conformation. The increased instability may be to any degree that is useful or significant for the intended application. For example, stability may be increased by about 10%, 25%, 50%, 100%, 200% (i.e. 2-fold), 300% (i.e. 3-fold), 400% (i.e. 4-fold), 500% (i.e. 5-fold), 1000% (i.e. 10-fold), or more.

A stabilized prefusion F polypeptide can be described by its physical and/or functional attributes. In some embodiments, a prefusion stabilized RSV F polypeptide contains a unique antigenic site referred to as "antigenic site Ø." The antigenic site Ø is located at the membrane-distal apex of the F protein when in a prefusion conformation, but elements of antigenic site Ø reposition in a postfusion conformation such that antibodies (e.g., D25 and AM22) cannot specifically bind the site. The antigenic site Ø can comprise amino acids 62-69 and 196-209 of a wild-type RSV F protein sequence (e.g., SEQ NO:1 or SEQ ID NO:2) or can comprise any antigenic site Ø sequence disclosed in US20150030622 and US20160046675.

An RSV F protein stabilized in a prefusion conformation can be specifically bound by an antibody that is specific for the prefusion conformation of the RSV F protein and does not bind a postfusion conformation, such as an antibody that specifically binds to an epitope within antigenic site Ø, for example, a D25, AM22, or 5C4 antibody. Methods to determine whether a F protein contains a prefusion epitope (e.g., a D25 epitope or AM22 epitope) are disclosed in U.S. Patent Application Publications US20100068217, incorporated by reference herein in its entirety, and in US20160046675. Heavy and light chain amino acid sequences of a D25 monoclonal antibody are disclosed in U.S. Patent Application Publication US20100239593, incorporated by reference herein in its entirety, and further disclosed in Kwakkenbos et al., *Nat. Med.*, 16:123-128 (2009). Heavy and light chain amino acid sequences of an AM22 monoclonal antibody are disclosed in U.S. Patent Application Publication US20120070446, incorporated by reference herein in its entirety, and the specificity of AM22 for prefusion F protein is disclosed in U.S. Patent Application Publication US20160046675. Heavy and light chain amino acid sequences of a 5C4 monoclonal antibody are disclosed in U.S. Patent Application Publication US20160046675 and in McLellan et al., *Science,* 340(6136): 1113-7 (2013).

Alternatively, RSV F protein stabilized in a prefusion conformation can be specifically bound by an antibody specific for the prefusion conformation of the RSV F protein but which does not bind antigenic site Ø, for example a MPE8 antibody. Heavy and light chain amino acid sequences of a MPE8 monoclonal antibody are disclosed in U.S. Patent Application Publication US20160046675 and further discussed in Corti et al., *Nature,* 501(7467):439-443 (2013).

Conversely, a postfusion conformation differs in three-dimensional folding of the RSV F polypeptide and is described in U.S. Patent Application Publication US20160046675, and further described at the atomic level in McLellan et al., *J. Virol.,* 85:7788 (2011); Swanson et al., *Proc. Natl. Acad. Sci.,* 108:9619 (2011); and in which structural coordinates are deposited and available at Protein Data Bank Accession No. 3RRR. A postfusion conformation does not include a D25 epitope, a AM22 epitope, or the same antigenic site Ø spatial arrangement as the prefusion conformation, and thus is not specifically bound by D25 or AM22 antibodies. A RSV F protein stabilized in a prefusion conformation can also be identified in some embodiments by the absence of binding by an antibody which specifically binds a postfusion conformation but does not bind a prefusion conformation. For example, an antibody which specifically binds the six-helix bundle present only in a postfusion conformation and not in a prefusion conformation does not specifically bind a RSV F protein stabilized in a prefusion conformation. An example of a postfusion-specific antibody is described in Magro et al., *Proc. Natl'l. Acad. Sci.,* 109:3089-94 (2012).

In some embodiments, the RSV F polypeptide stabilized in a prefusion conformation comprises a modification capable of forming one or more non-natural disulfide bonds, for example, by the addition of or substitution by one or more cysteine residues. RSV F polypeptides containing one or more modifications that create non-natural disulfide bonds in the RSV F polypeptide or between RSV F polypeptides are referred to herein with nomenclature that includes the letters "DS." A non-natural disulfide bond is one that does not occur in a native RSV F protein, and is introduced by protein engineering (e.g, by including one or more substituted cysteine residues that contribute to the formation of the non-natural disulfide bond). Examples of non-natural disulfide bond-forming modifications are described for RSV F polypeptide in U.S. Patent Application Publications US20150030622 and US20160046675. In some embodiments, the RSV F polypeptide comprises S155C and S290C amino acid substitutions which can form a disulfide bond. The S155C/S290C-substituted RSV F polypeptide is referred to herein as "DS," as further described in U.S. Patent Application Publications US20150030622 and US20160046675.

Accordingly, included herein are RSV F polypeptides stabilized in a prefusion conformation comprising one or more disulfide bonds which can stabilize the F polypeptide in a prefusion conformation. In some embodiments, the RSV F polypeptide can be an aqueous-soluble polypeptide comprising S155C/S290C-substitutions. The RSV F polypeptide can comprise the amino acid sequence of SEQ ID NO: 3, or a polypeptide sequence having at or greater than about 80%, at or greater than about 85%, at or greater than about 90%, at or greater than about 95%, or at or greater than about 98% homology with SEQ ID NO: 3. In some embodiments, the RSV F polypeptide can be a full-length polypeptide comprising S1.55C/S290C-substitutions. In some embodiments, the RSV F polypeptide comprises the amino acid sequence of SEQ ID NO: 4, or a polypeptide sequence having at or greater than about 80%, at or greater than about 85%, at or greater than about 90%, at or greater than about 95%, or at or greater than about 98% homology with SEQ ID NO: 4.

In some embodiments, the RSV F polypeptide stabilized in a prefusion conformation comprises a modification capable of forming one or more dityrosine bonds, for example, by the addition of or substitution by one or more tyrosine residues. RSV F polypeptides containing one or more modifications that create dityrosine bonds in the RSV F polypeptide or between RSV F polypeptides are referred to herein with nomenclature that includes the letters "DT." Numerous dityrosine bond-forming modifications are described for RSV F polypeptide in U.S. Patent Application Publication US20150030622, each being incorporated by reference herein. In some embodiments, the RSV F polypeptide comprises one or more of K77Y, N88Y, M97Y, A147Y, S150Y, S155Y, H159Y, N183Y, V185Y, V187Y, V220Y, E222Y, F223Y, K226Y, S255Y, K427Y and V469Y amino acid substitutions which can form a dityrosine bond. The dityrosine bond can be between an existing wild-type tyrosine residue (e.g., Y33, Y198, and Y286) and a tyrosine-substituted or inserted residue, or between two tyrosine-substituted or inserted residues. In some embodiments, the RSV F-polypeptide comprises one or more of K77Y, E222Y, and V469Y amino acid substitutions which can form a dityrosine bond. In some embodiments, the RSV F-polypeptide comprises a dityrosine bond between K77Y and E222Y, between Y33 and V469Y, or combinations thereof.

Accordingly, included herein are RSV F polypeptides comprising one or more dityrosine bonds which can stabilize the F polypeptide in a prefusion conformation. In some embodiments, the RSV F polypeptide can be an aqueous-soluble polypeptide comprising K77Y/E222Y substitutions. In some embodiments, the RSV F polypeptide comprises the amino acid sequence of SEQ ID NO: 5, or a polypeptide sequence having at or greater than about 80%, at or greater than about 85%, at or greater than about 90%, at or greater than about 95%, or at or greater than about 98% homology with SEQ ID NO: 5. In some embodiments, the RSV F polypeptide can be a full-length polypeptide comprising K77Y/E222Y substitutions.

In some or further embodiments, the RSV F polypeptide stabilized in a prefusion conformation comprises one or more amino acid substitutions which partially or completely fill a cavity within the F polypeptide or between F polypeptides. Polypeptides containing one or more such cavity mutations are referred to herein with nomenclature that includes the letters "CAV." The cavity can be between protomers of the RSV F protein, and can be a cavity present in a prefusion conformation which collapses (e.g., has reduced volume) after transition to a postfusion conformation. In some embodiments, the RSV F-polypeptide comprises one or more of S190F and V207L amino acid substitutions which can stabilize the F polypeptide in a prefusion conformation. A S190F/V207L-substituted RSV F polypeptide is referred to herein as "Cav1" and is further described in U.S. Patent Application Publications US20150030622 and US20160046675. In some embodiments, the RSV F polypeptide can be an aqueous-soluble polypeptide comprising S190F/V207L-substitutions. In some embodiments, the RSV F polypeptide comprises the amino acid sequence of SEQ NO: 6, or a polypeptide sequence having at or greater than about 80%, at or greater than about 85%, at or greater than about 90%, at or greater than about 95%, or at or greater than about 98% homology with SEQ ID NO: 6. In some embodiments, the RSV F polypeptide can be a full-length polypeptide comprising S190F/V207L-substitutions. In some embodiments, the RSV F polypeptide comprises the amino acid sequence of SEQ ID NO: 7, or a polypeptide sequence having at or greater than about 80%, at or greater than about 85%, at or greater than about 90%, at or greater than about 95%, or at or greater than about 98% homology with SEQ ID NO: 7.

An RSV F polypeptide can contain one or more combinations of modifications which stabilize the polypeptide in the prefusion conformation. For example, included herein are RSV F polypeptides containing two or more of DS, DT and CAV mutations. In some embodiments, the RSV F polypeptide comprises S190F, V207L, S155C, and S290C amino acid substitutions and is referred to herein as "DS-Cav1," as further described in U.S. Patent Application Publications US20150030622 and US20160046675. In some embodiments, the RSV F polypeptide can be an aqueous-soluble polypeptide comprising S190F/V207L/S155C/S290C amino acid substitutions. In some embodiments, the RSV F polypeptide comprises the amino acid sequence of SEQ ID NO: 8, or a polypeptide sequence having at or greater than about 80%, at or greater than about 85%, at or greater than about 90%, at or greater than about 95%, or at or greater than about 98% homology with SEQ ID NO: 8. In some embodiments, the RSV F polypeptide can be a full-length polypeptide comprising S190F/V207L/S155C/S290C amino acid substitutions. In some embodiments, the RSV F polypeptide comprises the amino acid sequence of SEQ ID NO: 9, or a polypeptide sequence having at or greater than about 80%, at or greater than about 85%, at or greater than about 90%, at or greater than about 95%, or at or greater than about 98% homology with SEQ ID NO: 9. Also included herein are RSV F polypeptides comprising K226Y/V185Y/N428Y/S190F/V207L amino acid substitutions (referred to herein as "DT-preF" and one species of a DT-CAV1 polypeptide).

In some embodiments, the RSV F polypeptide stabilized in a prefusion conformation further comprises a trimerization domain as described in U.S. Patent. Application Publications US20150030622 and US20160046675, which domain allows for trimerization of the RSV F polypeptide. The trimerization domain can be referred to as a Foldon domain. Accordingly, in some embodiments, the RSV F polypeptide is a homotrimer. The trimerization domain can comprise any trimerization domain polypeptide sequence, and can be encoded by any trimerization domain polynucleotide sequence, disclosed in U.S. Patent Application Publications US20150030622 and US20160046675.

Different monomers of an RSV F polypeptide stabilized in a prefusion conformation can, in some embodiments, be trimerized by inclusion of a trimerization domain, resulting in a heterotrimer (e.g., a heterotrimer of one monomer each of DS, DT, and Cav1). In such embodiments, the heterotrimer is stabilized in a prefusion conformation by one or more modifications. In some or further embodiments, a vaccine composition for vaccination against RSV can comprise a mixture of two or more RSV F polypeptides stabilized in a prefusion conformation and an inulin adjuvant (e.g., a mixture of "DSCav1" F polypeptides and "DTCav1" F polypeptides).

The compositions for vaccination further comprise an inulin adjuvant. Inulin is a polysaccharide produced naturally by some plants and is comprised of several isoforms of $\beta$-D-[2$\rightarrow$1] poly(fructofuranosyl)$\alpha$-D-glucose. As used herein, the term "inulin" refers to a $\beta$-D-[2$\rightarrow$1] poly(fructofuranosyl)$\alpha$-D-glucose. The term "adjuvant" refers to a composition that increases an immune response when co-administered with a second composition to a subject as compared to administration of the second composition alone. Co-administration may be simultaneous or delayed.

There are seven isoforms of inulin: alpha-1 (AI-1), alpha-2 (AI-2), gamma (GI), delta (DI), zeta (ZI), epsilon (EI) and omega (OI). Accordingly, in some embodiments, the inulin adjuvant can comprise alpha-1 inulin, alpha-2 inulin, gamma inulin, delta inulin, zeta inulin, epsilon inulin, omega inulin, or any combination thereof. In some embodiments, the inulin adjuvant can comprise delta inulin, epsilon inulin, omega inulin, or any combination thereof, wherein each of delta inulin, epsilon inulin, and omega inulin are as described in U.S. Patent Application Publication US 20170239349. In some embodiments, the inulin adjuvant can comprise delta inulin as described in U.S. Patent Application Publication US 20170239349. An example of a commercial delta inulin adjuvant is Advax, as further described in U.S. Patent Application Publication US 20170239349, WIPO Patent Application Publication WO2012175518, and Australian Patent Application Publication AU2017203501, each of which are incorporated herein in their entireties. Accordingly, in some embodiments, the compositions provided herein comprise a delta inulin particle as described in U.S. Patent Application Publication US 20170239349.

The compositions for vaccination against RSV infection can comprise a RSV F polypeptide stabilized in a prefusion conformation in various amounts. The composition can comprise the RSV F polypeptide in an amount ranging from about 1 ng/mL to about 1 g/mL. In some embodiments, the composition comprises RSV F polypeptide in an amount ranging from about 10 ng/mL to about 100 mg/mL, from about 100 ng/mL to about 10 mg/mL, from about 100 ng/mL to about 1 mg/mL, from about 1 µg/mL to about 1 mg/mL, or from about 10 µg/mL to about 1 mg/mL.

The compositions for vaccination against RSV can comprise an inulin adjuvant in various amounts. The composition can comprise the inulin adjuvant in an amount ranging from about 1 ng/mL, to about 1 g/mL. In some embodiments, the composition comprises an inulin adjuvant in an amount ranging from about 10 ng/mL to about 100 mg/mL, from about 100 ng/mL to about 10 mg/mL, from about 100 ng/mL to about 1 mg/mL, from about 1 µg/mL to about 1 mg/mL, or from about 10 µg/mL to about 1 mg/mL.

The compositions can further comprise additional components. For example, in some embodiments, the composition comprising RSV F polypeptide stabilized in a prefusion conformation and an inulin adjuvant can further comprise one or more CpG oligonucleotides. The CpG oligonucleotide can be a Class A, Class B, Class C, Class P or Class S CpG oligonucleotide. In some embodiments, the CpG oligonucleotide is a Class B CpG oligonucleotide.

Also disclosed herein are vaccine formulations and medicaments comprising a pharmaceutically effective amount of a RSV F polypeptide, an inulin adjuvant, and a pharmaceutically acceptable excipient. Suitable excipients include, but are not limited to, salts, diluents, (e.g., Tris-HCl, acetate, phosphate), preservatives (e.g., Thimerosal, benzyl alcohol, parabens), binders, fillers, solubilizers, disintegrants, sorbents, solvents, pH modifying agents, antioxidants, antinfective agents, suspending agents, wetting agents, viscosity modifiers, tonicity agents, stabilizing agents, and other components and combinations thereof. Suitable pharmaceutically acceptable excipients are preferably selected from materials which are generally recognized as safe (GRAS), and may be administered to an individual without causing undesirable biological side effects or unwanted interactions. Suitable excipients and their formulations are described in Remington's Pharmaceutical Sciences, 16th ed. 1980, Mack Publishing Co. In addition, such compositions can be complexed with polyethylene glycol (PEG), metal ions, or incorporated into polymeric compounds such as polyacetic acid, polyglycolic acid, hydrogels, etc., or incorporated into liposomes, microemulsions, micelles, unilamellar or multilamellar vesicles, erythrocyte ghosts or spheroblasts. Suitable dosage forms for administration, e.g., parenteral administration, include solutions, suspensions, and emulsions. Typically, the components of the vaccine formulation are dissolved or suspended in a suitable solvent such as, for example, water, Ringer's solution, phosphate buffered saline (PBS), or isotonic sodium chloride. The formulation may also be a sterile solution, suspension, or emulsion in a nontoxic, parenterally acceptable diluent or solvent such as 1,3-butanediol. In some cases, formulations can include one or more tonicity agents to adjust the isotonic range of the formulation. Suitable tonicity agents are well known in the art and include glycerin, mannitol, sorbitol, sodium chloride, and other electrolytes. In some cases, the formulations can be buffered with an effective amount of buffer necessary to maintain a pH suitable for parenteral administration. Suitable buffers are well known by those skilled in the art and some examples of useful buffers are acetate, borate, carbonate, citrate, and phosphate buffers. In some embodiments, the formulation can be distributed or packaged in a liquid form, or alternatively, as a solid, obtained, for example by lyophilization of a suitable liquid formulation, which can be reconstituted with an appropriate carrier or diluent prior to administration. The vaccine formulation comprises an RSV F polypeptide and an inulin adjuvant in a pharmaceutically effective amount sufficient to protect against RSV infection. The vaccine formulation can be formulated for medical and/or veterinary use.

The RSV for which the disclosed compositions for vaccination and vaccine formulations are protective against can be from any RSV subtype (e.g., subtypes A or B) capable of causing infection. In some embodiments, the RSV is a human RSV. In some embodiments, the RSV is a subtype A virus. In some embodiments, the RSV is a genotype comprising GA1, GA2, GA3, GA4, GA5, GA6, GA7, SAA1, NA1, NA2, NA3, NA4, ON1, or any combination thereof. In some embodiments, the RSV is a subtype B virus. In some embodiments, the RSV is a genotype comprising GB1, GB2, GB3, GB4, SAB1, SAB2, SAB3, SAB4, URU1, URU2, BA1, BA2, BA3, BA4, BA5, BA6, BA7, BA8, BA9, BA10, BA-C, THB, or any combination thereof. Future determined infectious or clinical RSV subtypes for which the disclosed compositions for vaccination and vaccine formulations are protective against are also contemplated and within the scope of the present disclosure.

Methods

Also disclosed herein are methods of vaccinating a subject against a respiratory syncytial virus (RSV) infection comprising administering to the subject a RSV F polypeptide stabilized in a prefusion conformation and an inulin adjuvant. The methods can elicit desirable cellular and immunological responses and increase protection against RSV in both vaccinated subjects and offspring born thereto. The methods further can increase overall safety of vaccination strategies against RSV for both vaccinated subjects and offspring born thereto.

The RSV F polypeptide can be any RSV F polypeptide stabilized in a prefusion conformation disclosed herein. Similarly, the inulin adjuvant can be any herein disclosed inulin adjuvant.

The RSV infection may be any herein disclosed RSV capable of causing infection (e.g., capable of infecting a subject, thereby resulting in a clinical diagnosis of RSV infection). In some embodiments, the RSV is a human RSV. In some embodiments, the RSV is a subtype A virus (e.g., GA1, GA2, GA3, GA4, GA5, GA6, GA7, SAA1, NA1, NA2, NA3, NA4, ON1, or any combination thereof). In some the RSV is a subtype B virus (e.g., GB1, GB2, GB3, GB4, SAB1, SAB2, SAB3, SAB4, URU1, URU2, BA1, BA2, BA3, BA4, BA5, BA6, BA7, BA8, BA9, BA10, BA-C, THB, or any combination thereof).

The subject can be any mammalian subject, for example a human, dog, cow, horse, mouse, rabbit, etc. In some embodiments, the subject is a primate, particularly a human. The subject can be a male or female of any age, race, creed, ethnicity, socio-economic status, or other general classifiers. In some embodiments, the subject is a female. In some embodiments, the subject is a female pregnant with an offspring (also referred to herein as a "maternal" subject). In some embodiments, the subject is a female that may soon become pregnant with an offspring (e.g., contemplating pregnancy, performing family planning, etc.). In some embodiments, the subject can be at risk of contracting or developing an RSV infection (e.g., via proximity to or contact with other subjects known to be or suspected to be infected with RSV). However, the subject need not be at risk of contracting or developing an RSV infection (e.g., the subject may be a member of a larger general population for which vaccination is generally recommended).

The methods are used to vaccinate a subject against a respiratory syncytial virus (RSV) infection. As used herein, the terms "vaccinate," "vaccinating," "vaccination," and grammatical variations thereof refer to the process of administering an immunogenic composition (e.g., comprising an RSV F polypeptide) to elicit an immune response in the subject to the administered immunogenic composition and infectious agent (e.g., RSV). In so doing, the subject can have increased protection from one or more subsequent exposures to the infectious agent. For example, and without limitation, the one or more subsequent exposures occurring post-vaccination may result in reduced viral titers, reduced amount and/or severity of symptoms, shortened duration of symptoms, and/or reduced need for treatment medications and/or clinician oversight, as compared to a control. In some embodiments, vaccination results in asymptomatic infection. The outcome (e.g., presence or severity of symptoms) of multiple subsequent exposures in the same subject may vary.

The RSV F polypeptide stabilized in a prefusion conformation and the inulin adjuvant can be administered to the subject together or as separate administrations. In some embodiments, the RSV F polypeptide and the inulin adjuvant are administered within a four-week period, within a three-week period, within a two-week period, or within a one-week period of each other. In some embodiments, the RSV F polypeptide and the inulin adjuvant are administered within a six-day period, within a five-day period, within a four day period, within a three day period, or within a two day period. In some embodiments, the RSV F polypeptide and the inulin adjuvant are administered within a 24-hour period, within a 12-hour period, within a 6-hour period, within a 3-hour period, or within a 1-hour period. In some embodiments, the RSV F polypeptide and the inulin adjuvant are administered concurrently, for example, in the same composition. In some embodiments, the RSV F polypeptide and the inulin adjuvant are administered together in a vaccine formulation comprising a pharmaceutically acceptable carrier.

The methods can include more than one administration of the RSV F polypeptide stabilized in a prefusion conformation, the inulin adjuvant, or both, for example as a vaccine boost. The methods can include at least one, at least two, at least three, at least four, at least five, at least six, at least seven, at least eight, at least nine, or at least ten administrations of the RSV F polypeptide. The methods can include at least one, at least two, at least three, at least four, at least five, at least six, at least seven, at least eight, at least nine, or at least ten administrations of the inulin adjuvant. The administration(s) can be performed prior to, concurrent with, or subsequent to administration of other agents (e.g., one or more additional diagnostic or therapeutic agents) to the subject.

The disclosed methods are useful for vaccinating a subject against RSV infection, and are further useful for protecting an offspring of a vaccinated mother against RSV infection. In some embodiments, the subject is a female pregnant with an offspring. Vaccination of the mother provides protective immunity against RSV infection to the mother, and further provides protection of the later-born offspring in early infantile stages (e.g., newborn, infant), early developmental stages (e.g., toddler, pre-school aged child, weanling), later offspring stages (e.g., school-aged child, preadolescent, adolescent), or any combination thereof. In some embodiments, more than one offspring (e.g., two, three, or more) can be protected against RSV infection. In some embodiments, any of the more than one offspring are from separate (e.g., more than one) pregnancies of the same subject.

In some embodiments, the subject may be a female who may become pregnant after being administered with the disclosed vaccine. In some embodiments, the vaccine may be administered within about one year prior to the female's pregnancy. In some embodiments, the vaccine may be administered within about nine months, six months, three months, two months, or one month prior to the female's pregnancy. In some embodiments, the vaccine may be administered within about four weeks, three weeks, two weeks, or one week prior to the female's pregnancy. In some embodiments, the vaccine may be administered within several days prior to the female's pregnancy.

In some embodiments, the vaccine may be first administered after the female has become pregnant with an offspring. In some embodiments, the vaccine may be first administered within about nine months, eight months, seven months, six months, five months, four months, three months, two months, or one month after the female has become pregnant with an offspring. In some embodiments, the vaccine may be first administered within about four weeks, three weeks, two weeks, or one week after the female has become pregnant with an offspring. In some embodiments, the vaccine may be first administered within several days after the female has become pregnant with an offspring.

The methods can include more than one administration of the RSV F polypeptide stabilized in a prefusion conformation, the inulin adjuvant, or both. For example, the methods can include a first administration and a second administration (e.g., one or more vaccine boosts). In some embodiments, there is one or more administrations to the subject before pregnancy and one or more administrations during pregnancy.

In some embodiments, a subsequent administration is provided at least one week after a prior administration. In some embodiments, a subsequent administration is provided at least two weeks, at least three weeks, or at least four weeks after a prior administration. In some embodiments, a subsequent administration is provided at least one month, at least two months, at least three months, at least six months, or at least twelve months after a prior administration.

The amount of the disclosed compositions administered to a subject will vary from subject to subject, depending on the nature of the disclosed compositions and/or vaccine formulations, the species, gender, age, weight and general condition of the subject, the mode of administration, and the like. Effective dosages and schedules for administering the compositions may be determined empirically, and making such determinations is within the skill in the art. The dosage ranges for the administration of the disclosed compositions and vaccine formulations are those large enough to produce the desired effect (e.g., to reduce RSV infection). The dosage should not be so large as to cause adverse side effects, such as unwanted cross-reactions, anaphylactic reactions, and the like. The dosage can be adjusted by the individual physician in the event of any counterindications. Generally, the disclosed compositions and/or vaccine formulations are administered to the subject at a dosage of active component(s) ranging from 0.1 µg/kg body weight to 100 g/kg body weight. In some embodiments, the disclosed compositions and/or vaccine formulations are administered to the subject at a dosage of active component(s) ranging from 1 µg/kg to 10 g/kg, from 10 µg/kg to 1 g/kg, from 10 µg/kg to 500 mg/kg, from 10 µg/kg to 100 mg/kg, from 10 µg/kg to 10 mg/kg, from 10 µg/kg to 1 mg/kg, from 10 µg/kg to 500 µg/kg, or from 10 µg/kg to 100 µg/kg body weight. Dosages above or below the range cited above may be administered to the individual patient if desired.

In some embodiments, the method reduces the RSV infection in the subject as compared to a control. In some embodiments, the method reduces the RSV infection in the subject by at least 25%, at least 50%, or at least 75% as compared to a control. In some embodiments, the method reduces the RSV infection in the subject by at least one-fold, at least two-fold, at least three-fold, at least four-fold, or at least five-fold as compared to a control. In some embodiments, the method reduces the RSV infection in the subject by at least one log, at least two logs, at least three logs, at least four logs, at least five logs, or at least six logs as compared to a control. In some embodiments, the method reduces the RSV infection in the subject to below an undetectable level.

In some embodiments, the RSV infection is reduced in a later-born offspring of a vaccinated female as compared to a control. In some embodiments, the method reduces the RSV infection in a later-born offspring of a vaccinated female by at least 25%, at least 50%, or at least 75% as compared to a control. In some embodiments, the method reduces the RSV infection in a later-born offspring of a vaccinated female by at least one-fold, at least two-fold, at least three-fold, at least four-fold, or at least five-fold as compared to a control. In some embodiments, the method reduces the RSV infection in a later-born offspring of a vaccinated female by at least one log, at least two logs, at least three logs, at least four logs, at least five logs, or at least six logs as compared to a control. In some embodiments, the method reduces the RSV infection in a later-born offspring of a vaccinated female to an undetectable level.

The amount of RSV infection can be determined in a biological sample from a subject or an offspring of the subject. The biological sample may be blood, plasma, serum, nasal swab, mucosal mouth or airway swab, sputum, tissue biopsy, or other suitable biological samples comprising RSV. The amount of RSV can be determined in the biological sample by, for instance, direct measurement of RSV particles (e.g., in a plaque assay) or portions thereof (antigens in e.g., a RSV-specific ELBA). In some embodiments, the amount of RSV infection can be determined by indirect measurements in a biological sample, such as detection of RSV-specific immunoglobulins or measurements of leukocyte counts. Alternatively, the amount of RSV infection can be determined by methods which do not require obtaining a biological sample (e.g., chest X-ray, skin pulse oximetry, general clinician observation, etc.).

The amount of RSV infection can be compared to a control. The control can be a biological sample from, for example, a cell line, a tissue stock, etc., or alternatively can be a subject (e.g., an unvaccinated subject). The control can alternatively be a subject, or a biological sample therefrom, which is vaccinated using a different vaccine or different vaccination method. A control should also be infected/challenged with a similar titer of RSV. In some embodiments, a control for comparing the amount of RSV infection can be a subject, or a biological sample therefrom, administered with a vaccine composition comprising a RSV F polypeptide and a non-inulin adjuvant. Alternatively, a control can be a collection of values used as a standard applied to one or more subjects (e.g., a general number or average that is known and not identified in the method using a sample).

One advantage of the disclosed methods is that the methods can increase the safety of anti-RSV vaccination compared to methods using other presently known vaccines or vaccine candidates. In some embodiments, the method increases safety of the subject, the offspring of the subject, or any combination thereof. In some embodiments, the method decreases eosinophilia in the subject or offspring as compared to a control. In some embodiments, essentially no clinical eosinophilia results in the subject or offspring after performing the methods. In some embodiments, the method decreases vaccine-enhanced respiratory disease (VERD; also known as enhanced respiratory disease (ERD) or vaccine enhanced disease (VED)) in the offspring of the subject as compared to a control. In some embodiments, essentially no clinical VERD results in the offspring of the subject after performing the methods. A control to which measures of safety can be compared can include a vaccinated subject using a different vaccine or different vaccination method, or a biological sample therefrom. In some embodiments, a control for comparing safety can be a subject, or a biological sample therefrom, administered with vaccine composition comprising an RSV F polypeptide and a non-inulin adjuvant. A control for comparing safety can be, but need not be, infected/challenged with RSV. Alternatively, a control for comparing safety can be a collection of values used as a standard applied to one or more subjects (e.g., a general number or average that is known and not identified in the method using a sample).

In some embodiments, the methods result in desirable cellular and immunological responses. In some embodiments, the subject and/or offspring of the subject can have reduced Fc receptor expression on natural killer cells. In some embodiments, the subject and/or offspring of the subject can have reduced. Scavenger Receptor A (SR-A) expression and/or increased major histocompatibility complex class II (MHCII) expression on resting alveolar macrophages. In some embodiments, the subject and/or offspring of the subject can have reduced eosinophil levels. In some embodiments, the subject and/or offspring of the subject can have increased CD8+ T cell levels, increased CD4+ T cell levels, or any combination thereof. In some embodiments, the subject and/or offspring of the subject can have reduced levels of interleukin 4 (IL-4), interleukin 5 (IL-5), interleukin 13 (IL-13), or any combination thereof. In some embodiments, the subject and/or offspring of the subject can have increased interferon gamma levels. In some embodiments, the subject and/or offspring of the subject can have increased anti-RSV F-polypeptide IgG antibody levels. In some embodiments, the subject and/or offspring of the subject can have an increased ratio of Th1:Th2 cell responses (e.g., increased ratio of Th1:Th2 cell levels). In some embodiments, the administration of the adjuvant increases the ratio of Th1:Th2 cell responses in the subject or offspring as compared to a control.

In some embodiments, the desirable cellular and immunological responses are measurable at least in bronchioalveolar lavage fluid (BALF). In some embodiments, the desirable cellular and immunological responses are compared to a control. The control can be a biological sample from, for example, a cell line, a tissue stock, etc., or alternatively can be a subject (e.g., an unvaccinated subject). The control can alternatively be a subject, or a biological sample therefrom, which is vaccinated using a different vaccine or different vaccination method. A control for comparing cellular and immunological responses can be infected/challenged with RSV. Alternatively, a control for comparing cellular and immunological responses can be a collection of values used as a standard applied to one or more subjects (e.g., a general number or average that is known and not identified in the method using a sample).

EXAMPLES

To further illustrate the principles of the present disclosure, the following examples are put forth so as to provide those of ordinary skill in the art with a complete disclosure and description of how the compositions, articles, and methods claimed herein are made and evaluated. They are not intended to limit the scope of the present invention. These examples are not intended to exclude equivalents and variations of the present invention which are apparent to one skilled in the art. Unless indicated otherwise, temperature is ° C. or is at ambient temperature, and pressure is at or near atmospheric. There are numerous variations and combinations of process conditions that can be used to optimize product quality and performance. Only reasonable and routine experimentation will be required to optimize such process conditions.

Example 1

Anti-RSV Maternal Vaccination with DS-Cav1 Paired with Delta Inulin Adjuvant Protects Mothers and Offspring and Improves Immune Responses The disclosed technology relates to vaccinating pregnant mothers against Respiratory Syncytial Virus (RSV) with DS-Cav1 (also referred to herein as "DSCav1") and DS-Cav1 in combination with Advax or Advax-SM. DS-Cav1 is a preconformational RSV F polypeptide used for RSV vaccination, and Advax is a delta inulin adjuvant. Advax-SM refers herein to a combination of Advax and CpG oligonucleotide consisting of SEQ NO:10. The strategy provides protective immunity to both mother and offspring (e.g., infants and weanlings), and reduces adverse side-effects of vaccination such as vaccine-enhanced respiratory disease (VERD).

Protective immunity in the lungs of DS-Cav1+Advax-SM immunized dams following RSV challenge. Advax-SM adjuvant can overcome immune insufficiencies associated with young age (Honda-Okubo et al., *Vaccine*, 2015; 33(38): 4892-900) and pregnancy (Honda-Okubo et al., *Vaccine*, 2014; 32(36):4651-9) and its enhancement of vaccine protection and amelioration of eosinophilic lung pathology in other murine models, such as SARS coronavirus infection (Honda-Okubo et al., *J. Virol.*, 2015; 89(6):2995-3007). To determine the efficacy of immunization with DS-Cav1 formulated with or without Advax-SM, 7-8-week-old female BALB/c mice were intramuscularly vaccinated with DS-Cav1+Advax-SM (DS-Cav1+Advax-SM dams), unadjuvanted DS-Cav1 (DS-Cav1 dams), or PBS vehicle control (PBS dams) on Day 0. Immunized females were then bred and boosted at 14 days gestation with their respective vaccine formulation. After infant mice were weaned, immunized dams were challenged with RSV 32 days after their final immunization. Pre-challenge plaque reducing neutralizing titers (1/PRNT50) indicated that the addition of Advax-SM to DS-Cav1 enhanced the RSV neutralizing antibody response by an average of 4-fold over unadjuvanted vaccine (Table 1).

Figure 1A:
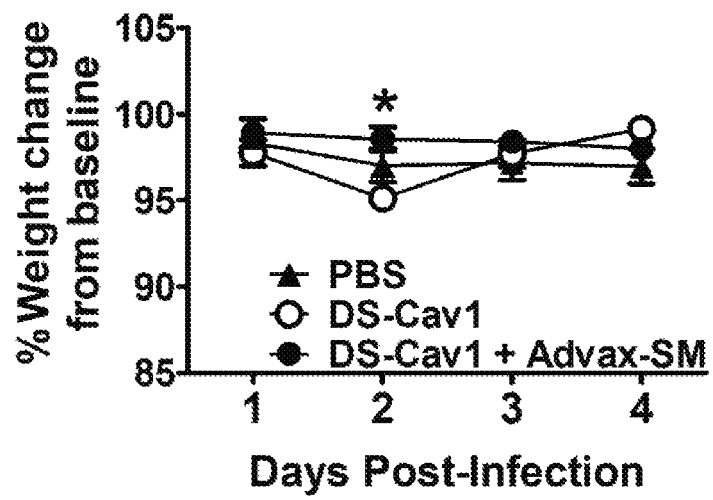
Figure 1B:
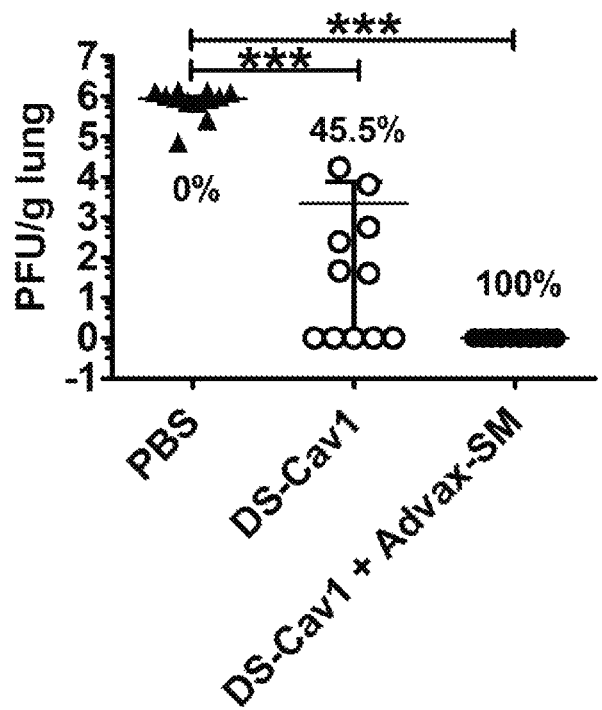
Figure 1C:
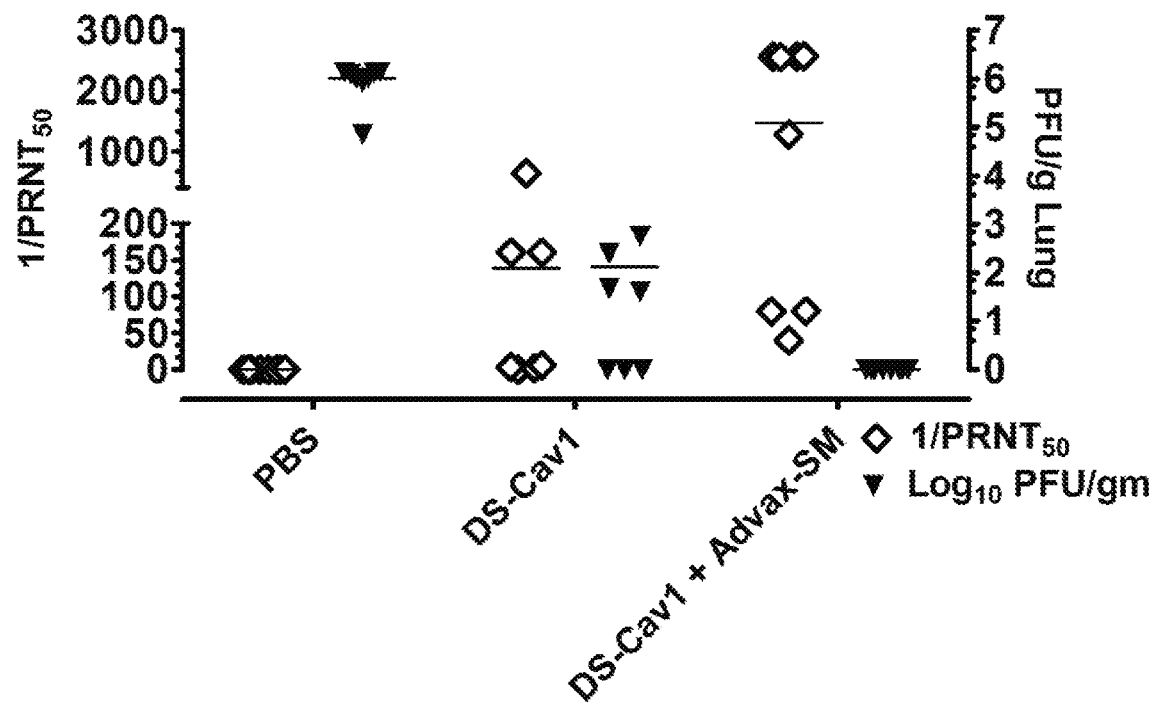

DS-Cav1, but not DS-Cav1+Advax-SM or PBS dams, lost weight transiently at 2 days post-infection (dpi) (FIG. 1A). At 4 days post-infection (dpi), the time of peak RSV replication, DS-Cav1+Advax-SM and DS-Cav1 dams had significantly reduced viral titers compared to PBS dams (FIG. 1B). When challenged 57 days after initial vaccination, only DS-Cav1+Advax-SM completely protected dams with 100% (n=12/12) of animals in this group showing no detectable virus in their lungs. Within each vaccination group, viral titers (right y-axis) were negatively correlated with neutralizing antibody titers (left y-axis); 1/PRNT50 values≥40 were associated with complete protection from RSV (FIG. 1C). PBS dams had no detectable neutralizing antibody and had high viral titers, whereas all DS-Cav1+ Advax-SM dams had 1/PRNT50 values≥40 and sterilizing immunity. Unadjuvanted DS-Cav1 dams with 1/PRNT50 values≥40 similarly had sterile lungs, whereas those with undetectable neutralizing antibody had detectable virus in their lungs (FIGS. 1B and 1C). These results demonstrate that immunization of dams with DS-Cav1+Advax-SM augments neutralizing antibody responses and provides greater anti-viral protection compared to DS-Cav1 alone.

Figure 2:
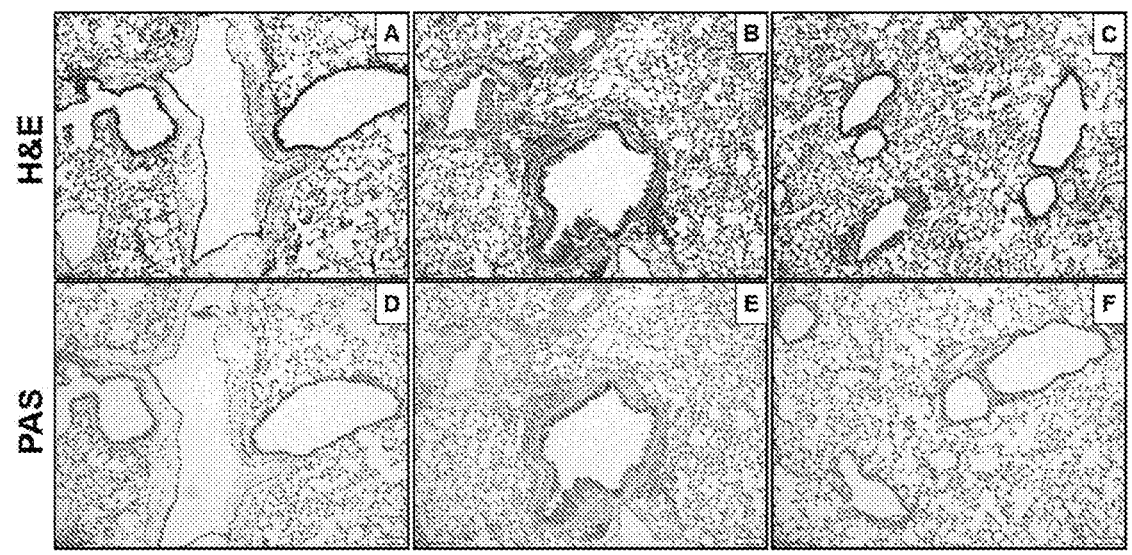
FIG. 2 is a micrograph showing DS-Cav1+Advax-SM immunization of dams reduces lung inflammation and mucus production. 7-8 week old female, BALB/cJ mice were immunized, bred, and challenged with RSV L19. At 4 dpi, right lungs were harvested and stained with H&E (top panels) and PAS (bottom panels) and imaged at 10× magnification; bar indicates 100 μm. From left to right the samples are: PBS, DS-Cav1, and DS-Cav1+Advax-SM. Lung sections stained with PAS were scored 0 to 4 for PAS positivity with 0 having no PAS and 4 being 76-100% PAS+.

DS-Cav1+Advax-SM immunization of dams reduces lung inflammation and mucus production. To evaluate the risk of VERU in DS-Cav1-immunized dams with or without an adjuvant, histologic analysis was performed on the lungs of immunized dams 4 days after RSV challenge to assess inflammation (FIG. 2, top panels) and mucus production (FIG. 2, bottom panels). Hematoxylin & eosin (H&E)-stained lung sections showed enhanced alveolitis as well as peri-bronchial and peri-vascular inflammation in DS-Cav1 compared to PBS- or DS-Cav1+Advax-SM dams (FIG. 2, top panels). Additionally, DS-Cav1 dams had increased mucin production as evidenced by increases in Periodic Acid Shift (PAS) staining of cells lining the airway (FIG. 2, bottom middle panel), whereas, mucin production was limited in lung sections of PBS- (FIG. 2, bottom left panel) and DS-Cav1+Advax-SM-immunized dams (FIG. 2, bottom right panel). Quantification of mucin production (Asquith et al., *J. Immun.*, 2008; 180(2):1199-206; Wills-Karp et al., *Science*, 1998; 282(5397):2258-61) confirmed that DS-Cav1-immunized dams produced more mucus (0=77.03%; 1=9.93%; 2=4.15%; 3=2.86%; 4=6.05%) than DS-Cav1+Advax-SM– (0=96.83%; 1=5.14%) or PBS– (0=99.63%; 1=0.37%) immunized dams following RSV challenge.

Figure 3A:
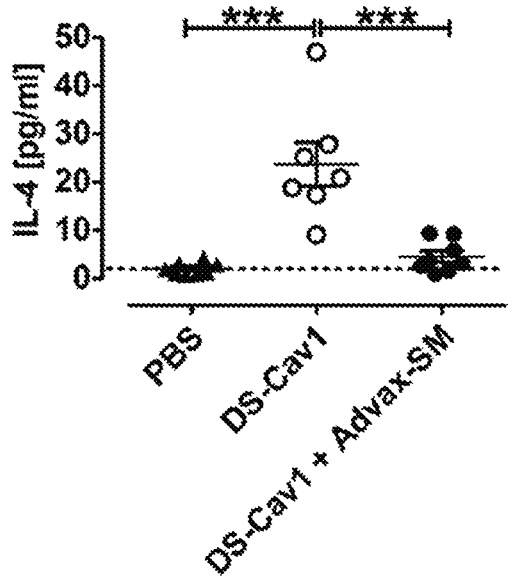
FIG. 3(A-F) are graphs depicting formulation of DS-Cav1 with Advax-SM ameliorates increased Th2-type cytokine production exhibited by DS-Cav1 dams following RSV challenge. At 4 dpi, first wash samples were collected from immunized dams and analyzed for cytokines using Luminex. Dotted lines indicate the assay's limit of detection for individual cytokines. Cytokine concentrations were compared between groups using ANOVA with a Tukey post-test. Symbols represent individual mice in their respective immunization groups and lines represent the mean of n≥7 animals per group±SEM: *$p<0.05$, $p<0.01$, *$p<0.001$.
Figure 3B:
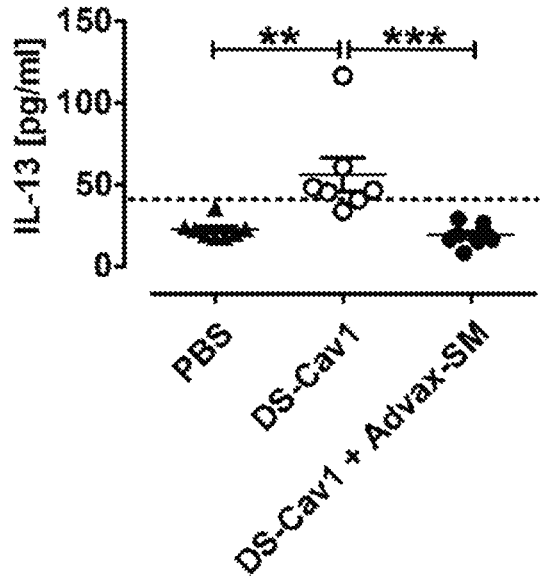
Figure 3C:
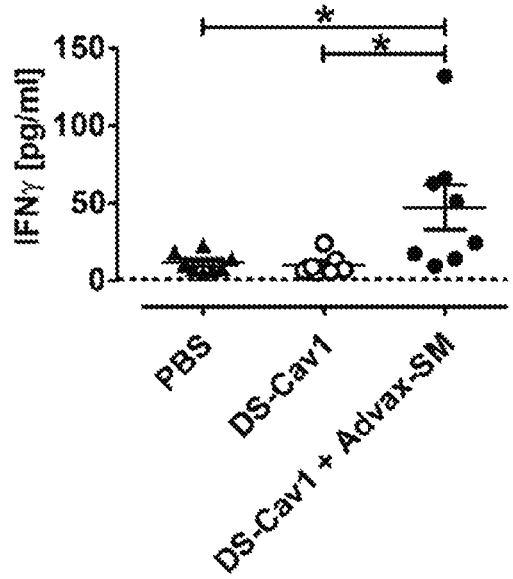
Figure 3D:
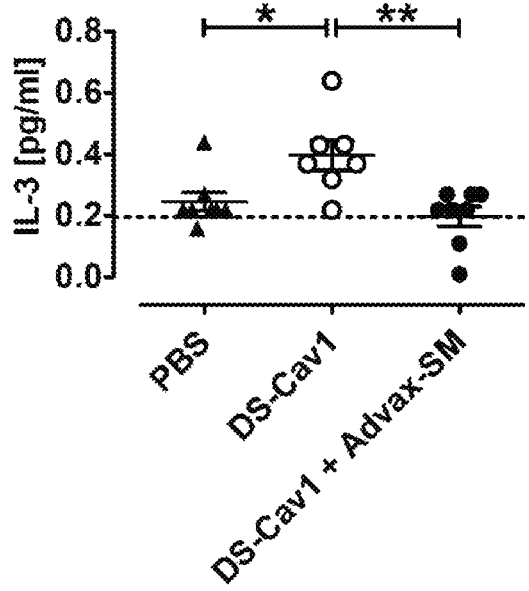
Figure 3E:
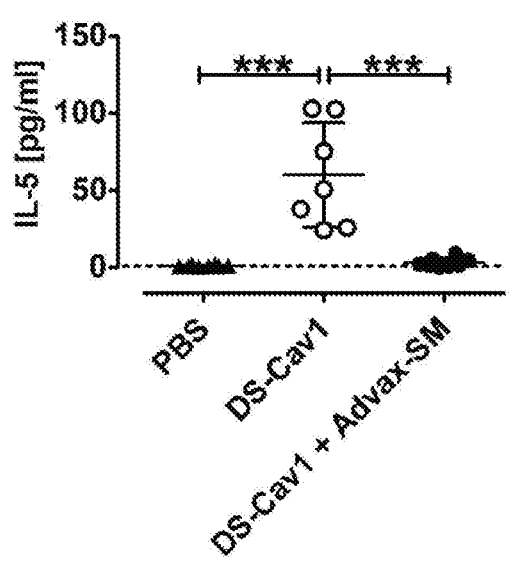
Figure 3F:
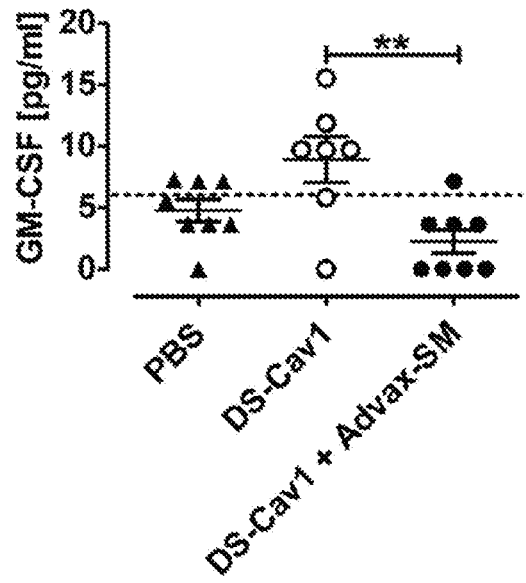

Formulation of DS-Cav1 with Advax-SM ameliorates Th2-type cytokine production exhibited by DS-Cav1 dams following RSV challenge. Consistent with histologic findings demonstrating peri-vascular and bronchial inflammation with enhanced mucus production, DS-Cav1 dams had significantly elevated concentrations of the Th2 cytokines, IL-4 (FIG. 3A) and IL-13 (FIG. 3B), quantified from first-wash bronchoalveolar lavage (BAL) samples. Moreover, concentrations of the Th1 cytokine IFNγ were significantly higher in DS-Cav1+Advax-SM dams while PBS and DS-Cav1 dams had similarly low levels (FIG. 3C). IL-4 and IL-13 concentrations were reduced in DS-Cav1+Advax-SM dams, as compared to DS-Cav1 dams, and had minimal inflammation based on H&E staining, with only a small increase in PAS-staining over PBS dams (FIG. 2, lower panels). Additionally, the Th2 cytokines IL-3 (FIG. 3D), IL-5 (FIG. 3E), and GM-CSF (FIG. 3F), which are critical for the expansion and accumulation of eosinophils (Asquith et al., *J. Immun.*, 2008; 180(2):1199-206), were significantly elevated in DS-Cav1 dams at 4 dpi, as compared to PBS and DS-Cav1+Advax-SM dams. Together, these data demonstrate that RSV infection of dams immunized with unadjuvanted DS-Cav1, but not PBS or DS-Cav1+Advax-SM, elicits the production of Th2-type cytokines in vaccinated dams following viral challenge.

Figure 4A:
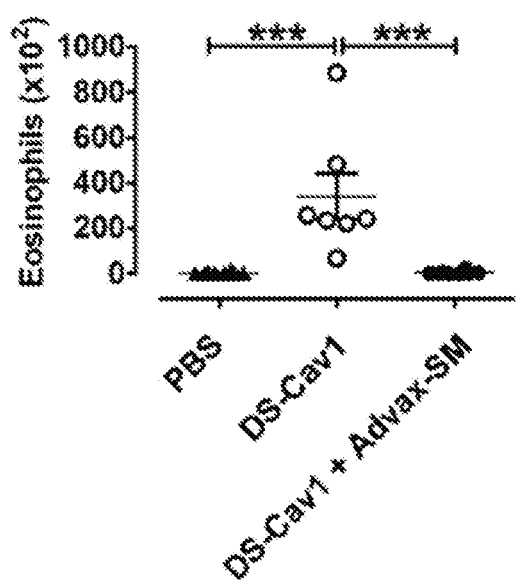
FIG. 4(A-J) are graphs depicting disparate innate immune responses in the airways of immunized dams following RSV challenge. Total cells quantified in the BAL at 4 dpi (FIG. 4A through FIG. 4D) or digested lung tissue (FIG. 4E through FIG. 4J) are shown for eosinophils (FIGS. 4A and 4E) making IL-5 (FIG. 4F) or TNFα (FIG. 4G), monocytes (FIG. 4B), neutrophils (FIG. 4C), Siglec F-macrophages (FIGS. 4D and 4H), and Siglec F-macrophages making IL-5 (FIG. 4I) or TNFα (FIG. 4J). Populations of cells within the BAL and digested lung tissue, surface marker expression, and intracellular cytokines were compared between immunization groups using ANOVA with a Tukey post-test. Symbols represent individual mice in their respective immunization groups and lines represent the mean of n≥7 animals per group±SD; *$p<0.05$, $p<0.01$, *$p<0.001$.
Figure 4B:
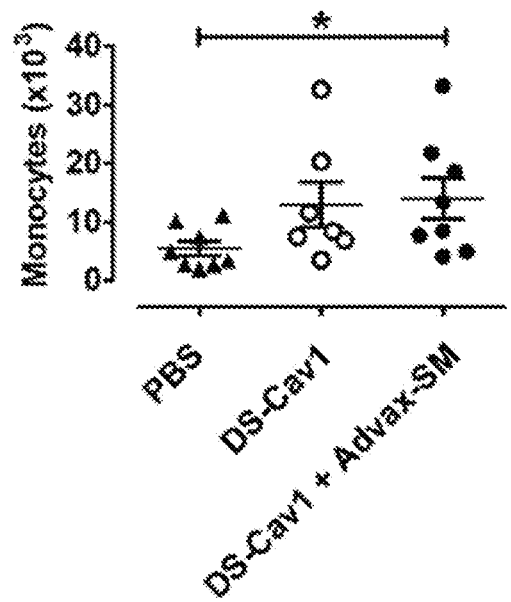
Figure 4C:
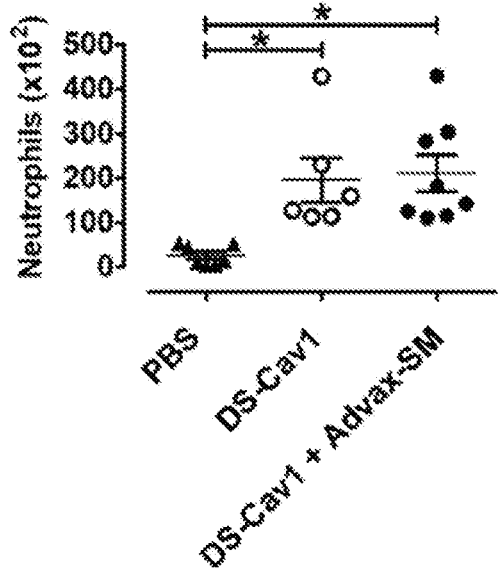
Figure 4D:
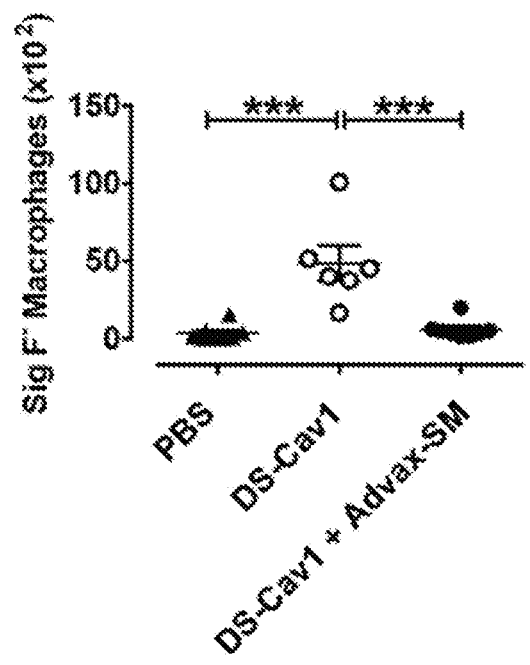
Figure 4E:
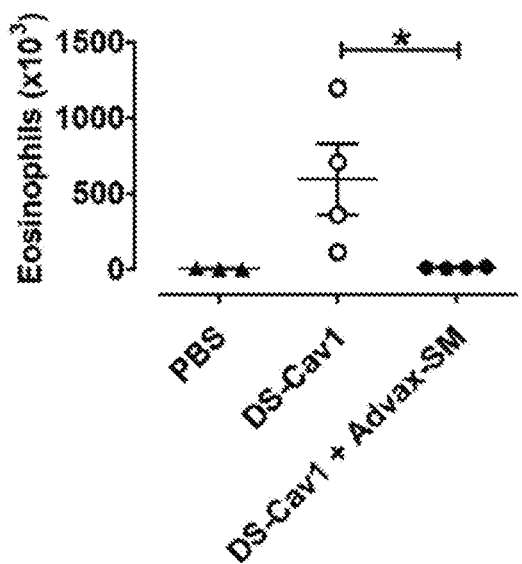
Figure 4F:
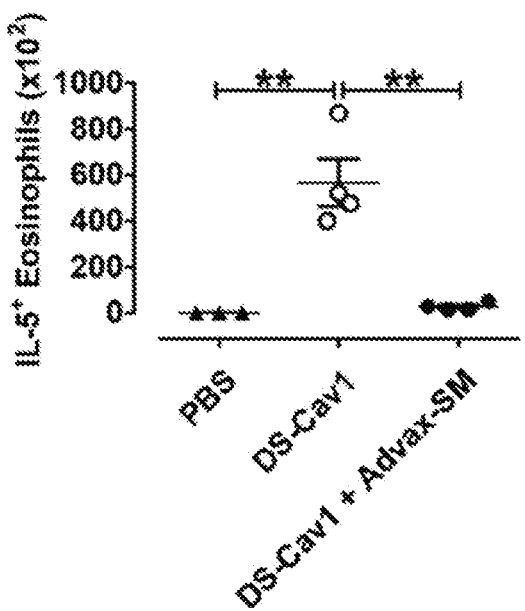
Figure 4G:
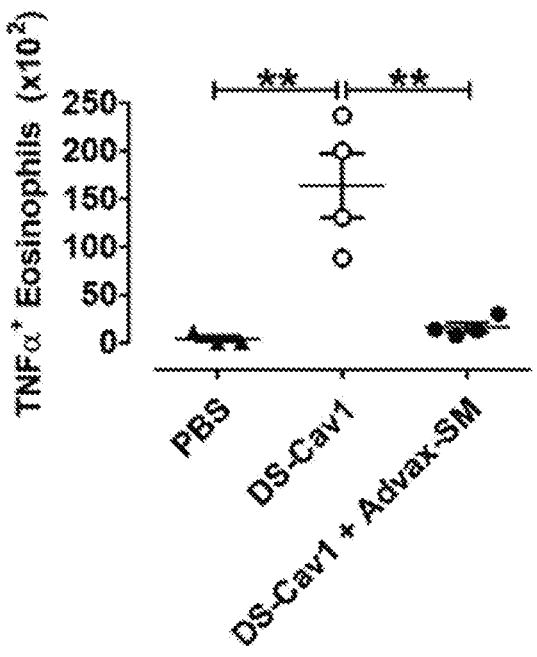

Contrasting innate cellular immune responses in the airways of immunized dams following RSV challenge. Consistent with elevated concentrations of IL-3, IL-5, and GM-CSF, alveolar (FIG. 4A) and interstitial eosinophils (FIG. 4E; Siglec F+ F4/80+ CD206– CD11clo/–CD11b+), were increased in DS-Cav1 dams (FIGS. 3D through 3F) as opposed to PBS or DS-Cav1+Advax-SM dams. Moreover, eosinophils present in the lung tissue of DS-Cav1 dams were producing IL-5 (FIG. 4F) and TNFα (FIG. 4G), which are known to recruit eosinophils and enhance inflammation, respectively.

Figure 4H:
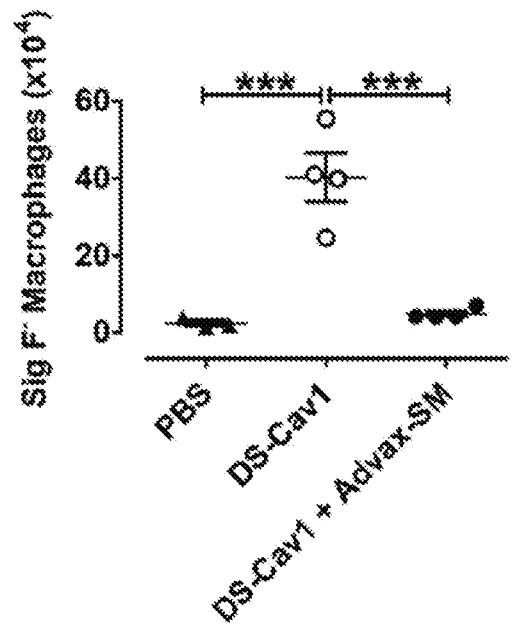
Figure 4I:
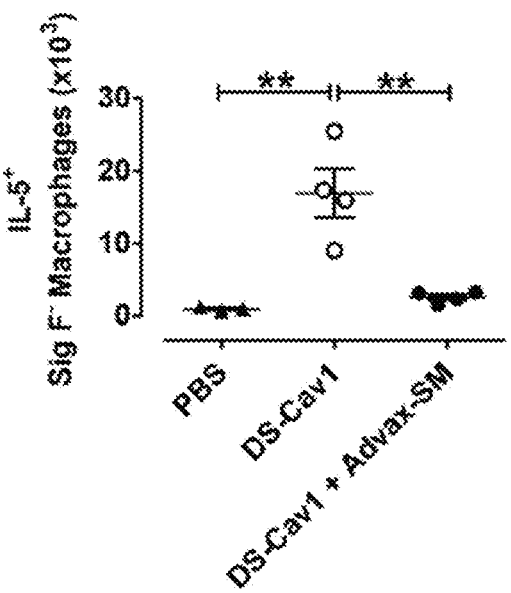
Figure 4J:
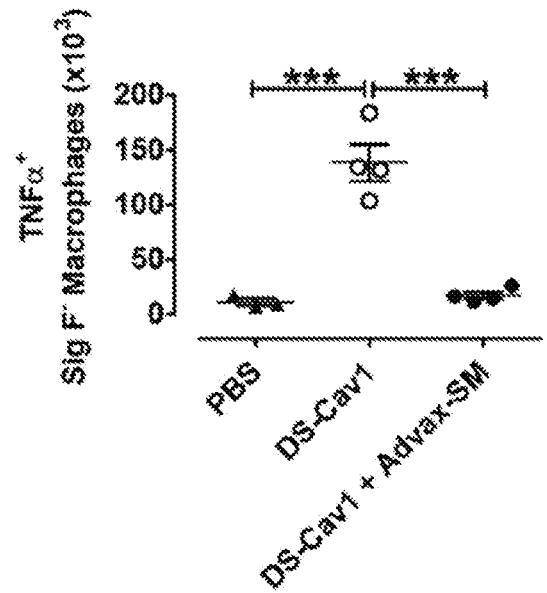

Monocytes (Siglec F– F4/80+ CD206– CD11c+ CD11b+) and neutrophils (Siglec F– CD11bHI Ly6G+ CD11clo), each of which were shown to be elevated in the airways of FI-RSV-immunized human children (Acosta, *Clin. Vacc. Immunol.*, 2015; 23(3):189-95; Prince et al., *J. Gen. Virology*, 2001; 82(12):2881-8; Lee et al., *Virology*, 2015; 485: 36-46), were increased in the BAL of both DS-Cav1 and DS-Cav1+Advax-SM dams as compared to PBS dams (FIGS. 4B and 4C), suggesting that they are not largely responsible for the development of VERD. Alternatively, Siglec F– (Sig F–) macrophages (Siglec F– F4/80+ CD206+ CD11c+ CD11b+), which are associated with an inflammatory lung environment (Janssen et al., *Eur. Respir, J.*, 2016; 48(4):1201-14), were significantly increased in the BAL (FIG. 4D) and lungs (FIG. 4H) of DS-Cav1 dams. Similar to eosinophils, Sig F– macrophages in the lungs of DS-Cav1 dams produced elevated levels of IL-5 (FIG. 4I) and TNFα (FIG. 4J), which were absent in PBS and DS-Cav1+Advax-SM dams.

Figure 5A:
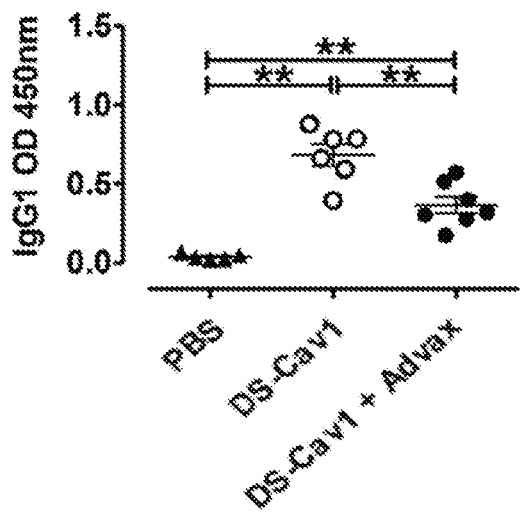
FIG. 5(A-J) are graphs showing that immunization with DS-Cav1+Advax-SM increases Th1 responses to RSV infection. RSV-specific IgG isotype titers were measured from the antisera of immunized dams at 4 dpi, according to the methods. IgG1 (FIG. 5A), IgG2a (FIG. 5B), and the IgG1 to IgG2a ratio (FIG. 5C) was compared between immunization groups using ANOVA with Tukey post-test. At 4 dpi, activated (CD44+CD25+) CD4+ T cells producing IL-4+ (FIG. 5D) and IFNγ+ (FIG. 5E) and replicating Ki-67+ CD4 T cells (FIG. 5F) were measured. Activated CD8+ producing IFNγ+ (FIG. 5G) were isolated from the BAL. MHC I pentamer specific for RSV F85-93 (FIG. 5H) was used to identify RSV F85-93 specific, activated (CD44HI), CD8 T cells as well as RSV-specific and proliferating (Ki-67+) Tbet+ CD8+ T cells (FIG. 5I) were also isolated from the BAL at 4 dpi. A ratio of IFNγ vs. IL-4 producing TCRβ+ cells was created from cells isolated from the BAL at 4 dpi.
(FIG. 5J). Lymphocyte populations were compared using ANOVA with Tukey post-test. Symbols represent individual mice in their respective immunization groups and lines represent the mean of n≥4 animals per group±SEM; *$p<0.05$, $p<0.01$, *$p<0.001$. Data represents 2 independent experiments.
Figure 5B:
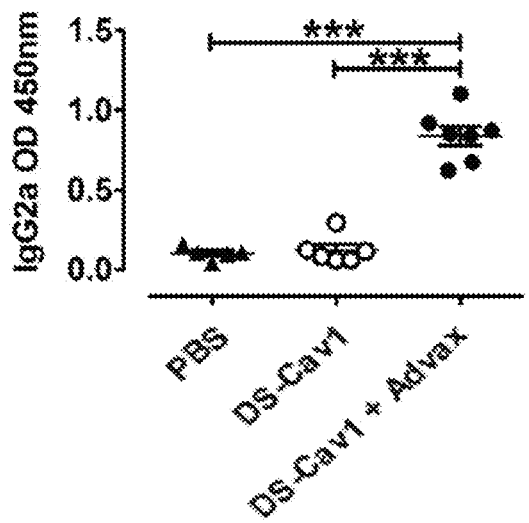
Figure 5C:
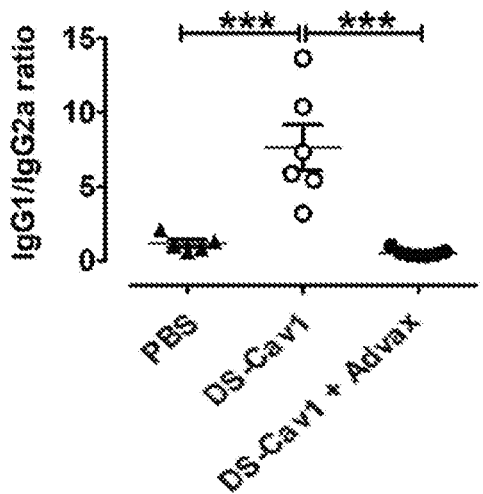

Immunization with DS-Cav1+Advax-SM increases Th1 responses to RSV infection. The obtained cytokine and innate cellular data suggest that Advax-SM adjuvant ameliorated the Th2 bias observed in dams immunized with DS-Cav1 alone. To further investigate the T-helper bias elicited by maternal DS-Cav1 immunization in the presence or absence of Advax-SM, RSV-specific IgG subtypes were quantified. Anti-RSV IgG1 antibody titers associated with Th2 polarization, were increased in DS-Cav1+Advax-SM– and DS-Cav1 dams over PBS dams (FIG. 5A), though DS-Cav1 dams had significantly higher IgG1 levels than DS-Cav1+Advax-SM dams. Conversely, IgG2a antibody titers, which are linked to a Th1 cytokine environment, were significantly elevated only in DS-Cav1+Advax-SM dams (FIG. 5B). The mean IgG1/IgG2a ratio was 7.6 in DS-Cav1 dams and 0.53 in DS-Cav1+Advax-SM dams (FIG. 5C), indicating a greater Th2 bias in DS-Cav1 dams as opposed to DS-Cav1+Advax-SM or PBS dams.

Figure 5D:
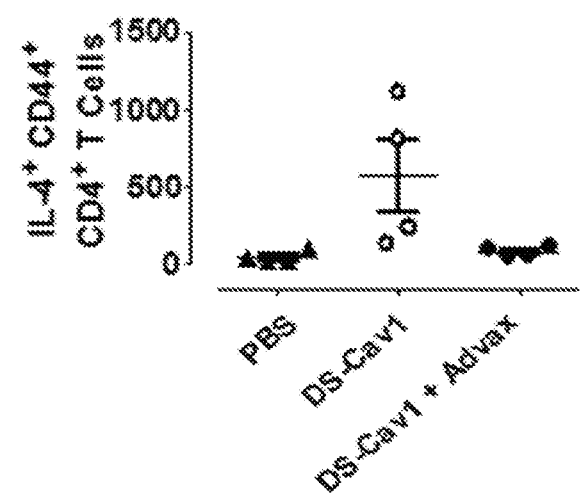
Figure 5E:
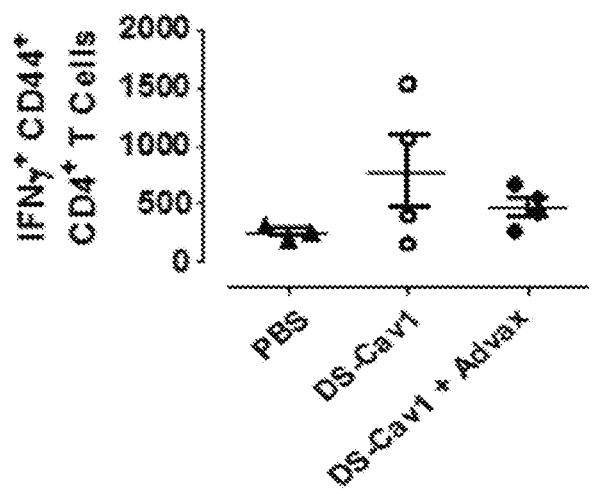
Figure 5F:
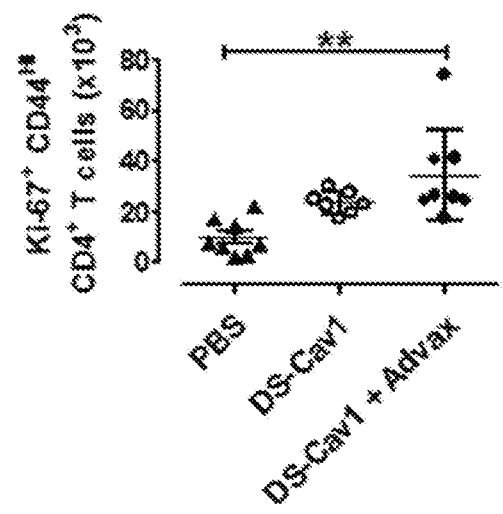
Figure 5G:
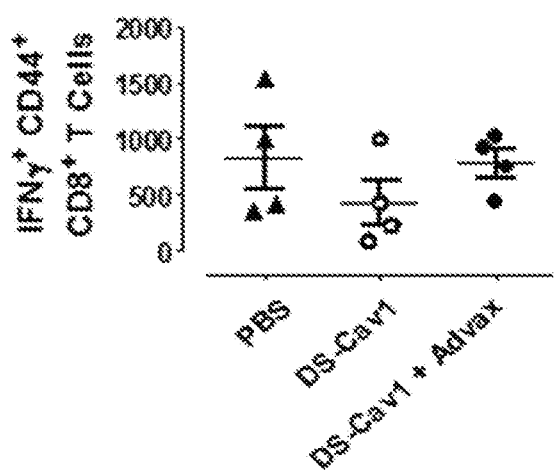
Figure 5H:
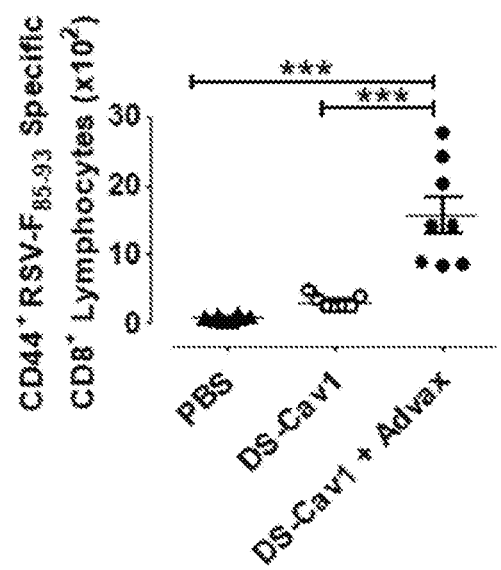
Figure 5I:
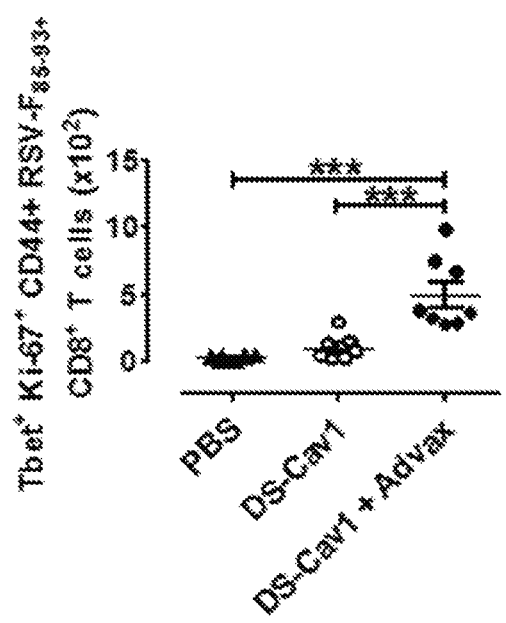
Figure 5J:
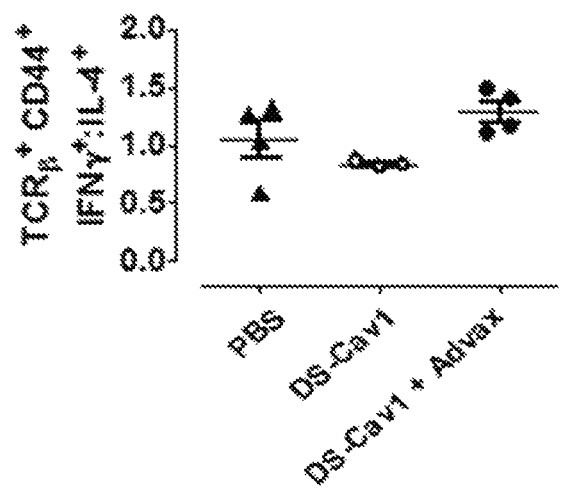

To determine the contribution of T helper responses to the Th2-type cytokine environment, T cells from the BAL were quantified and intracellular cytokines were measured. At 4 dpi, the number of activated (CD44+ CD25+) CD4+ T cells producing IL-4 trended toward higher levels in the BAL of DS-Cav1 dams (FIG. 5D), with similarly elevated numbers of IFNγ-producing, activated CD4+ T cells (FIG. 5E). There was a non-significant trend toward reduced numbers of activated CD8+ T cells producing IFNγ in the BAL of DS-Cav1 dams (FIG. 5F). Using an MHC I pentamer specific for RSV F85-93 and expression of Ki-67, these results showed a striking increase in RSV-specific CD8 T cell response and enhanced CD8 T cell replication that DS-Cav1+Advax-SM dams compared to DS-Cav1 and PBS dams (FIGS. 5H and 5I). To measure Th1 (IFNγ) vs. Th2 (IL-4) cytokine production from the general T cell population, the numbers of TCRβ+ cells producing IFNγ were compared to those producing IL-4. The IFNγ+/IL-4+ ratio was significantly higher in TCRβ+ cells from DS-Cav1+ Advax-SM dams compared to DS-Cav1 dams (FIG. 6J), signifying a collective reduction in IL-4 and a greater IFNγ response from T cells in DS-Cav1+Advax-SM dams.

Overall, these results indicate that DS-Cav1+Advax-SM induced a Th1-biased response with a low IgG 1/IgG2a RSV-specific antibody response, increased RSV F85-93-specific CD8+ T cells, and an elevated IFNγ to T cell ratio compared to dams immunized with DS-Cav1 alone.

Figure 6A:
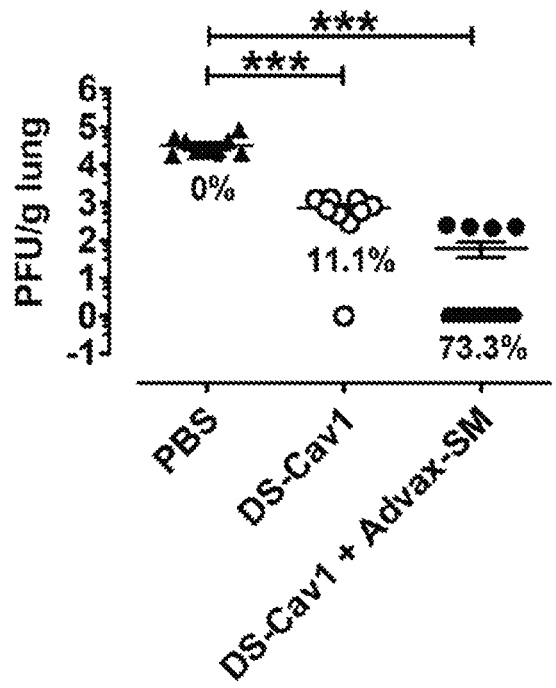
FIG. 6(A-D) are graphs showing that infants and weanlings of DS-Cav1+Advax-SM dams are protected from RSV. Results for infants are shown in FIGS. 6A and 6C; results for weanlings are shown in FIGS. 6B and 6D. Infants (postnatal day 5-6; "PND5-6") and weanlings (PND35) born to immunized dams (PBS infants/weanlings, DS-Cav1 infants/weanlings, DS-Cav1+Advax-SM infants/weanlings) were challenged with RSV and left lungs harvested at 4 dpi and processed for viral quantification using H&E plaque assays (FIGS. 6A and 6B). Lungs with no detectable virus were considered sterile and percentages of sterile lungs were calculated for each offspring group. Serum was collected from offspring at 4 dpi and 1/PRNT50 titers measured. Viral titers and RSV neutralization assays were performed in triplicate and individual symbols within each group represent the mean titers for each animal, lines represent the mean of n≥7 animals per group±SEM. Viral titers and neutralizing antibody levels were compared between groups using ANOVA with a Tukey post-test; ***$p<0.001$.
Figure 6B:
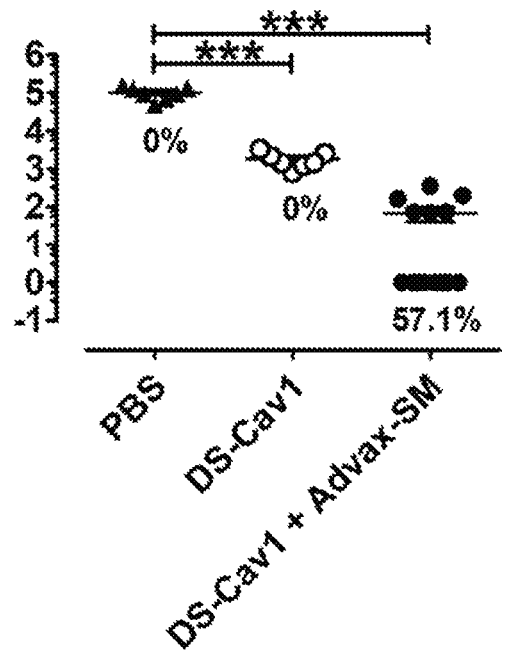
Figure 6C:
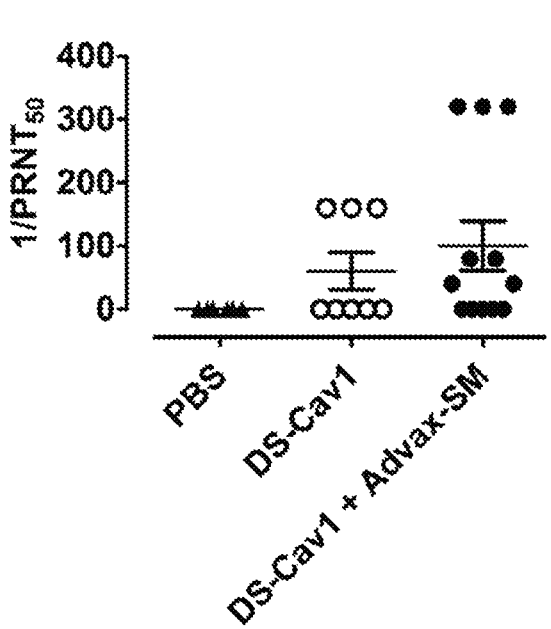

Infants and weanlings of DS-Cav1+Advax-SM dams are protected from RSV. To measure the extent to which maternal immunization protected their offspring from RSV infection over time, nursing infant mice (PND 5-6) and weanlings (2 weeks post-wean) born to immunized mothers were challenged with RSV. At 4 dpi, infants born to DS-Cav1+Advax-SM dams (DS-Cav1+Advax-SM infants) exhibited significantly greater RSV protection (sterilizing immunity in 11/15; 73%) compared to infants born to DS-Cav1 dams (DS-Cav1 infants) (sterilizing immunity in 1/9; 11.1%) (FIG. 6A). Correlating with RSV protection, 58% (n=7/12) of DS-Cav1+Advax-SM infants had 1/PRNT50≥40 compared to only 38% (n=3/8) of DS-Cav1 infants (FIG. 6C).

Figure 6D:
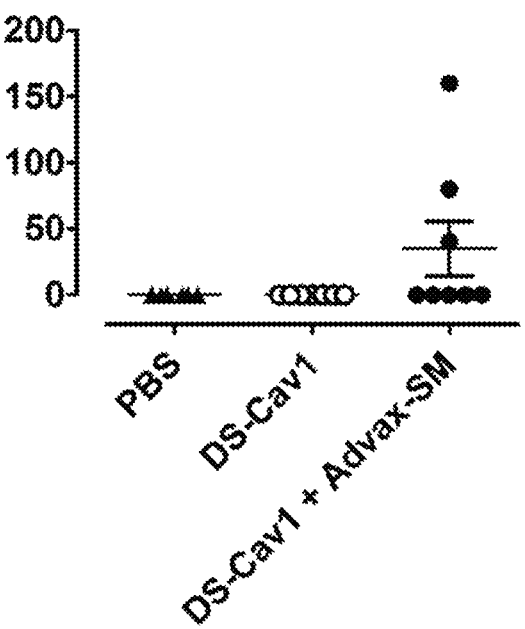

To determine if RSV protection was maintained in offspring after nursing ceased, offspring (PND 35) that were weaned at 21 days of age were challenged with RSV. Weanlings born to dams immunized with DS-Cav1+Advax-SM (DS-Cav1+Advax-SM weanlings) had higher levels of sterilizing immunity (57%, n=8/14) at 4 dpi compared to weanlings of DS-Cav1 dams (DS-Cav1 weanlings) (0%, n=0/7) (FIG. 6B). Similarly, a higher proportion of DS-Cav1+Advax-SM weanlings had 1/PRNT50≥40 (38%, n=3/8) compared to DS-Cav1 weanlings (0%, n=0/7) (FIG. 6D). In offspring born to both DS-Cav1 immunized groups, nursing infants had higher neutralizing antibody titers compared to weanlings born to mothers in the same immunization groups, reflecting the expected decay of neutralizing antibody levels post-wean (FIGS. 6C and 6D). As expected, offspring of PBS dams (PBS infants and PBS weanlings) had high viral lung titers and no measurable neutralizing antibody at 4 dpi. Taken together, these results demonstrate that maternal DS-Cav1+Advax-SM immunization provides RSV protection immediately after birth. This immunity begins to decline by two weeks after the cessation of the passive antibody transfer via breast milk.

Figure 7A:
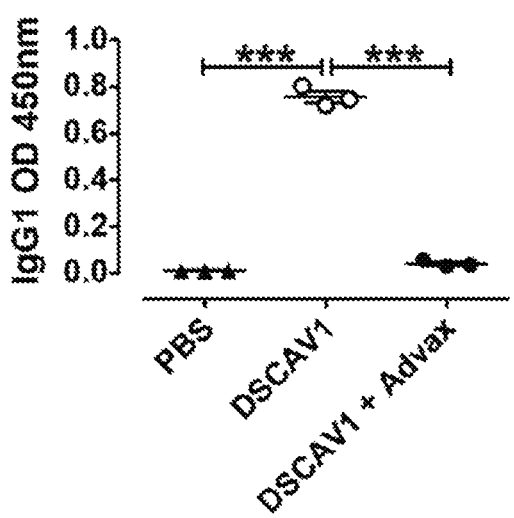
FIG. 7(A-H) is a set of graphs showing Dendritic Cells of weanlings are influenced by maternal vaccination. Pre-challenge serum was collected from weanlings (PND37) born to immunized dams, then the animals were challenged with RSV. IgG1 (FIG. 7A), IgG2a (FIG. 7B), IgG1 to IgG2a ratios (FIG. 7C), and combined totals of IgG1 and IgG2a (FIG. 7D) were measured from weanling pre-challenge serum and compared between passive-immunization groups using ANOVA with Tukey post-test. At 4 dpi, DCs (Sig F-CD11c+ MHCIIHI) (FIG. 7E), the percentages of DCs expressing CD86+ (FIG. 7F), CD11b+ CD103− (FIG. 7G), and CD11b− CD103+ (FIG. 7H) were compared between groups. Individual symbols within each group represent individual mice, lines represent the mean of ≥3 samples per group±SEM. Comparisons between groups were made using ANOVA with a Tukey post-test; *$p<0.05$, ***$p<0.001$. Data represents 2 independent experiments.
Figure 7B:
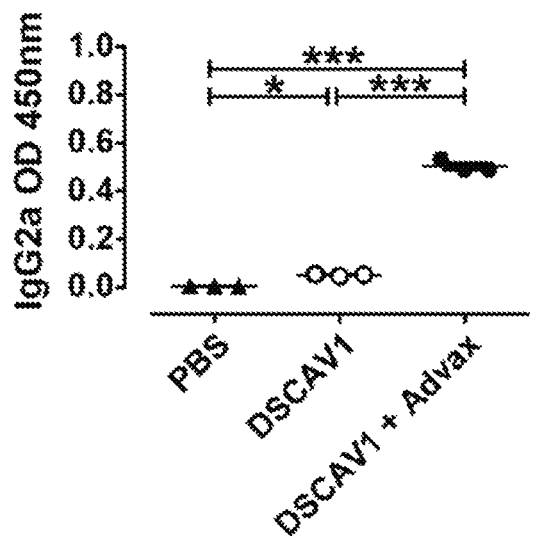
Figure 7C:
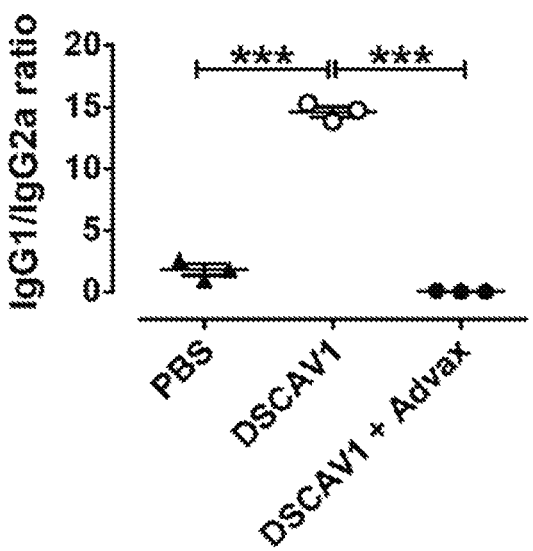
Figure 7D:
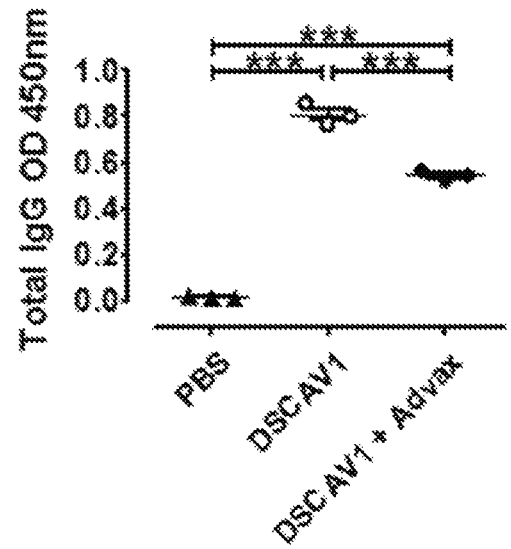
Figure 7E:
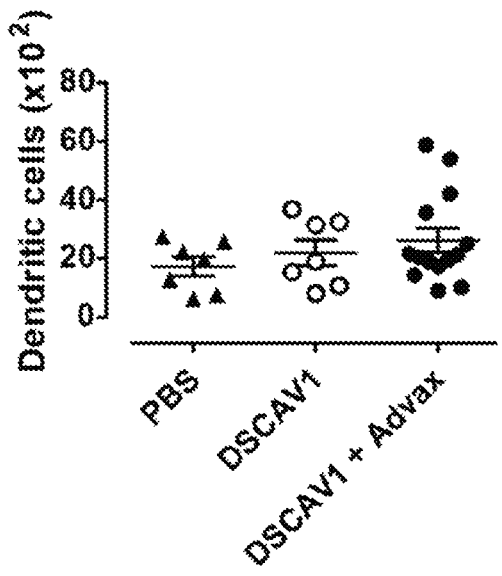
Figure 7F:
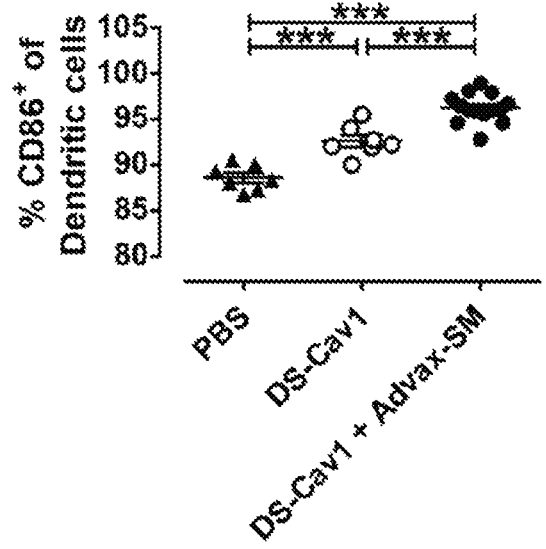
Figure 7G:
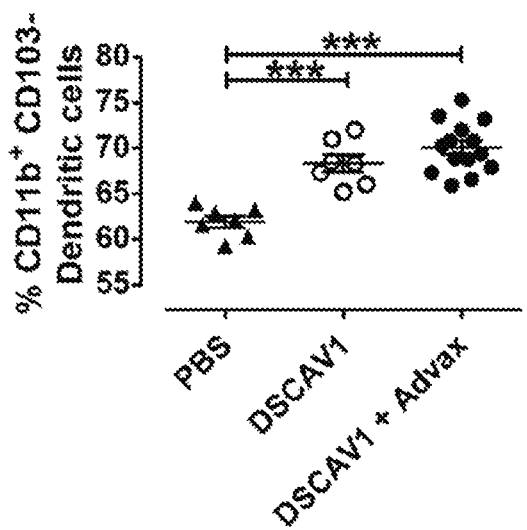
Figure 7H:
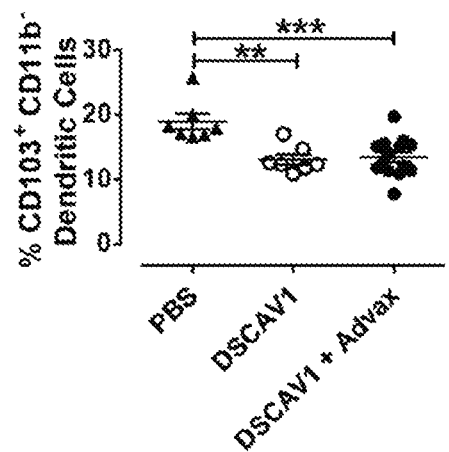

Maternal antibody influences weanling dendritic cell activation. Though infants challenged within a week after birth were well protected in the DS-Cav1+Advax-SM group, maternal antibody levels had begun to decline by two weeks post-wean. Thus, the extent to which dendritic cell (DC) activation was influenced following first-time viral challenge in weanlings with low maternal antibody titers was determined. It was first determined if the antibody subtypes transferred to the offspring mirrored that of their mothers. RSV-specific antibody subtype levels measured in weanling sera prior to viral challenge were largely reflective of subtype levels in dams from their respective immunization groups (FIGS. 7A through 7C), suggesting an equal transfer of maternal antibody subtypes to the offspring with minimal differences in subtype-specific antibody metabolism through the time of weaning. DS-Cav1 weanlings had significantly higher anti-RSV IgG1 titers than DS-Cav1+Advax-SM weanlings (FIG. 7A) but low titers of IgG2a (FIG. 7B), resulting in a mean IgG1/IgG2a ratio>14 (FIG. 7C). Conversely, DS-Cav1+Advax-SM weanlings had extremely low IgG1 titers and high IgG2a levels producing a mean IgG1/IgG2a ratio approaching zero (FIG. 7C). Combined IgG1 and IgG2a titers were greater overall in the DS-Cav1 weanling group, reflective of the higher IgG1 titers (FIG. 7I)). Given that IgG2a antibodies generally have higher binding affinities than IgG1 to activating Fcγ receptors (Guilliams et al., Nat. Rev. 2014; 14(2):94-108.), it was determined whether DCs from DS-Cav1+Advax-SM weanlings would exhibit greater activation following RSV challenge leading to an enhanced T cell response. The total number of DCs in the BAL, of weanlings at 4 dpi did not differ significantly between groups (FIG. 7D). However, expression of the co-stimulatory marker CD86 on DCs was highest in DS-Cav1+Advax-SM weanlings, followed closely by DS-Cav1 weanlings, both of which had a higher frequency of CD86 expression compared to PBS weanlings (FIG. 7F). Interestingly, both DS-Cav1+Advax-SM and DS-Cav1 weanlings had a higher frequency of CD11b+ CD103– DCs compared to PBS weanlings (FIG. 7F), whereas the frequency of CD103-expressing DCs was reduced in weanlings born to immunized dams versus PBS dams (FIG. 7G). These data suggest there was little to no association with IgG subtype and DC activation between weanling groups from dams immunized with DS-Cav1 and DS-Cav1+Advax-SM, but instead more closely reflected the presence of residual maternal antibody and increased viral lung titers (FIG. 6).

Figure 8A:
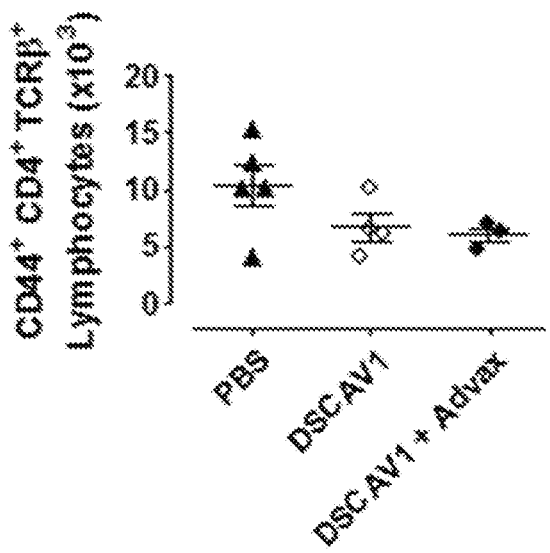
FIG. 8(A-H) is a set of graphs showing T cells from the BAL of weanlings are influenced by maternal vaccination. BAL samples were collected at 8 dpi from weanling groups and analyzed for total events of activated (CD44+) CD4+ T cells (FIG. 8A), and the percentage of these cells expressing IL-4 (FIG. 8B), IL-5 (FIG. 8D), and IFNγ+ (FIG. 8E). The MEI of IL-4+ and the ratio of IFNγ:IL-4 in CD4 T cells were also reported (FIG. 8C and 8F). Activated CD44+ CD8+ T cells (FIG. 8G) and the ICCS of IFNγ in these CD8+ T cells were reported (FIG. 8H). Individual symbols within each group represent individual mice, lines represent the mean of ≥3 samples per group±SEM. Comparisons between groups were made using ANOVA with a Tukey post-test; *$p<0.05$, ***$p<0.001$. Data represents 2 independent experiments.
Figure 8B:
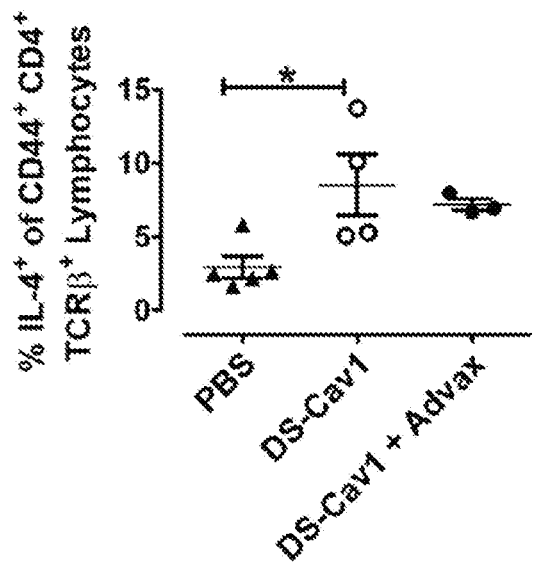
Figure 8C:
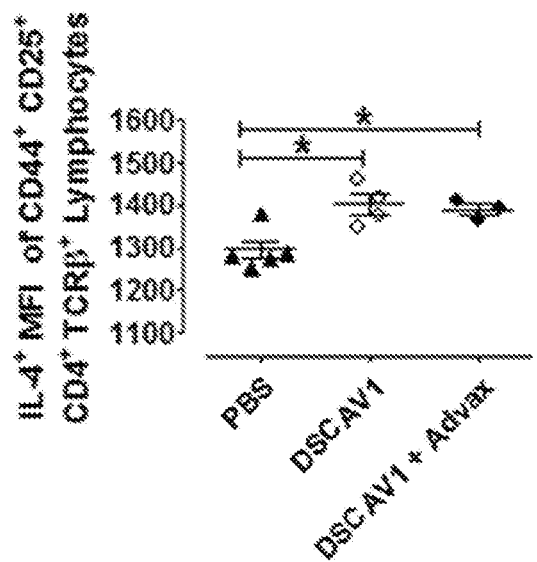
Figure 8D:
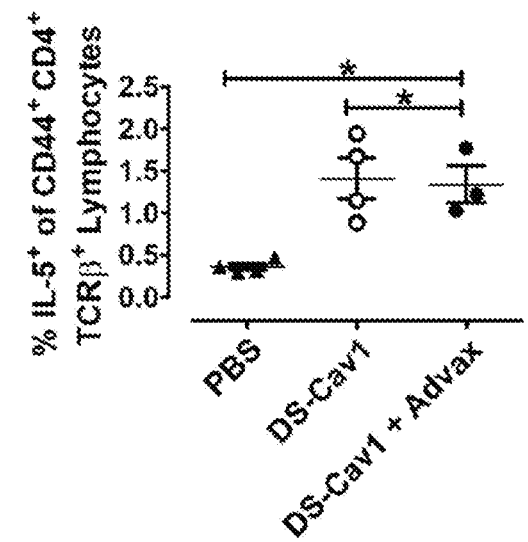
Figure 8E:
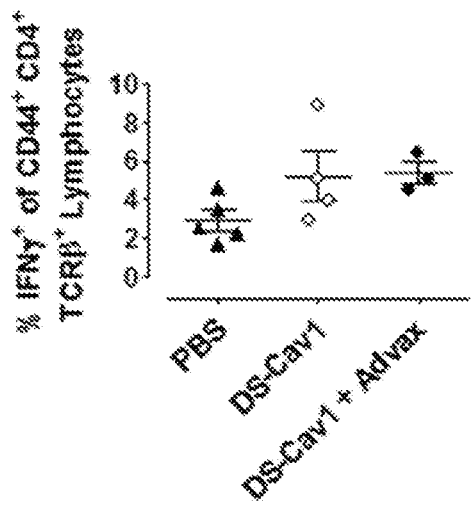
Figure 8F:
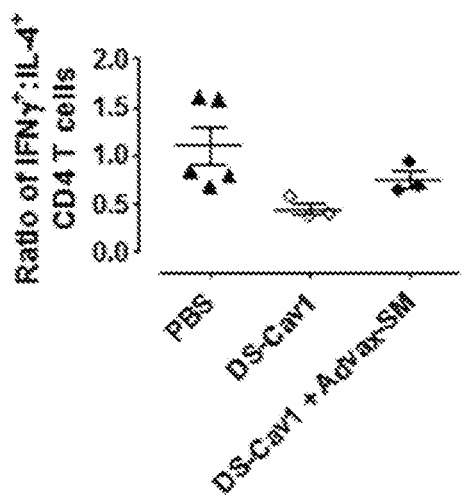
Figure 8G:
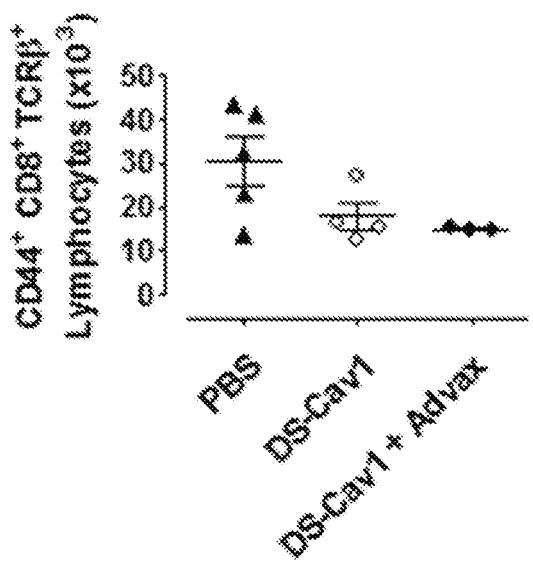
Figure 8H:
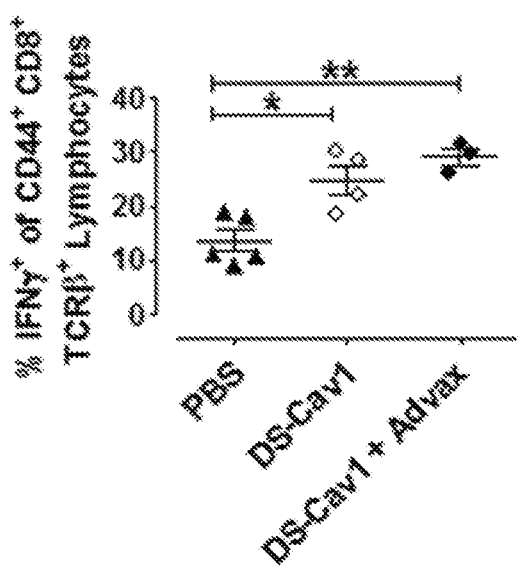
Figure 10A:
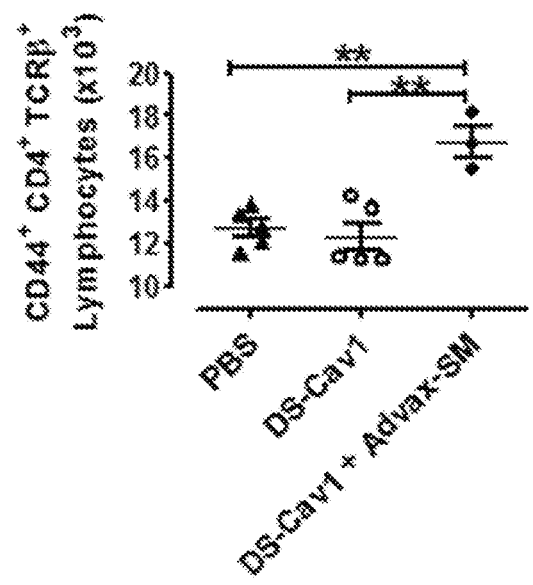
FIG. 10(A-F) is a set of graphs showing T cells from the lungs of weanlings are influenced by maternal vaccination. Lung samples were collected at 8 dpi from weanling groups, digested, and analyzed for total events of activated (CD44+) CD4+ T cells (FIG. 10A), and the percentage of these cells expressing IFNγ (FIG. 10B), IL-4 (FIG. 10C), and IL-5 (FIG. 10D). Activated CD44+ CD8+ T cells (FIG. 10E) and the ICCS of IFNγ in these CD8+ T cells were reported (FIG. 10F). Individual symbols within each group represent individual mice, lines represent the mean of ≥3 samples per group±SEM. Comparisons between groups were made using ANOVA with a Tukey post-test; *$p<0.05$, ***$p<0.001$. Data represents 2 independent experiments.
Figure 10B:
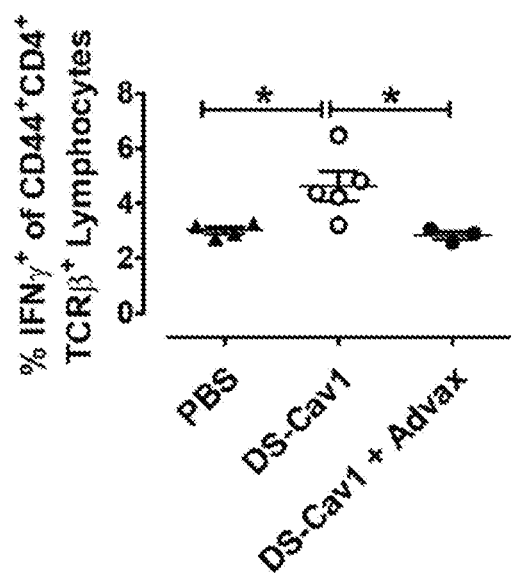
Figure 10C:
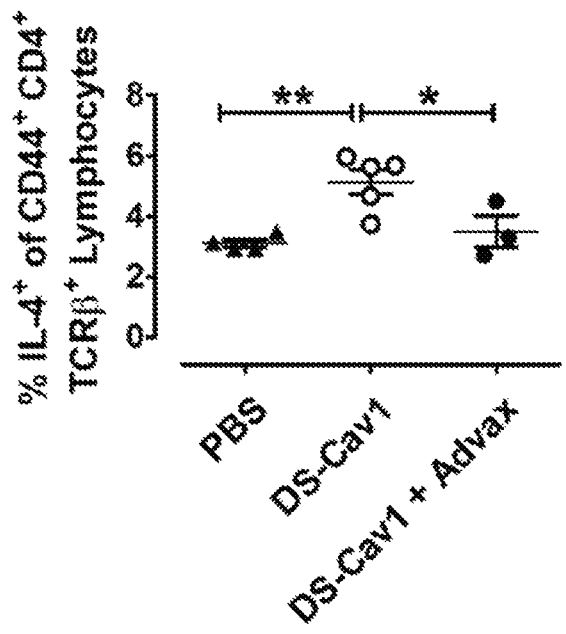
Figure 10D:
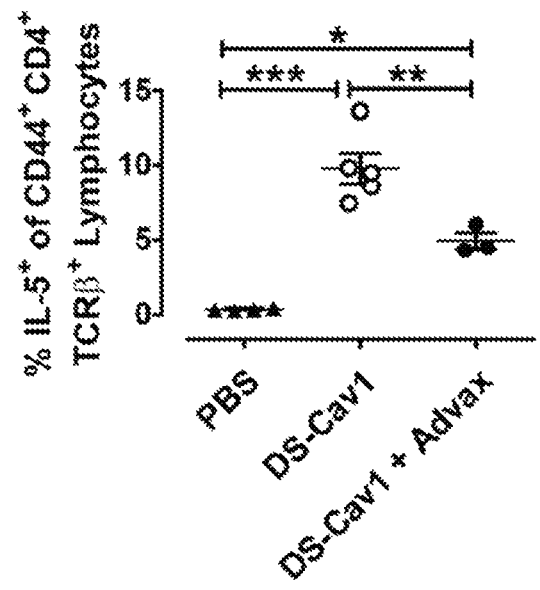
Figure 10E:
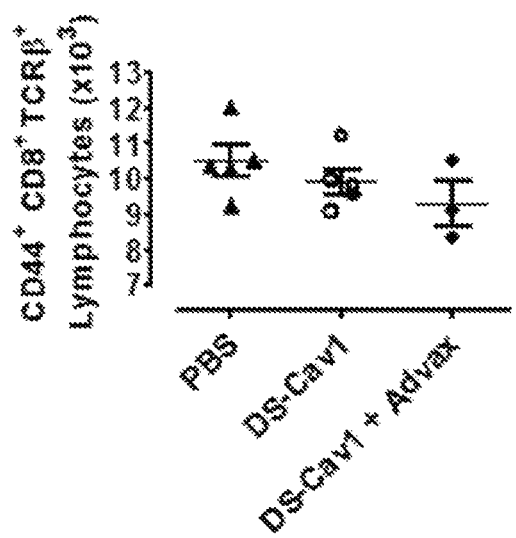
Figure 10F:
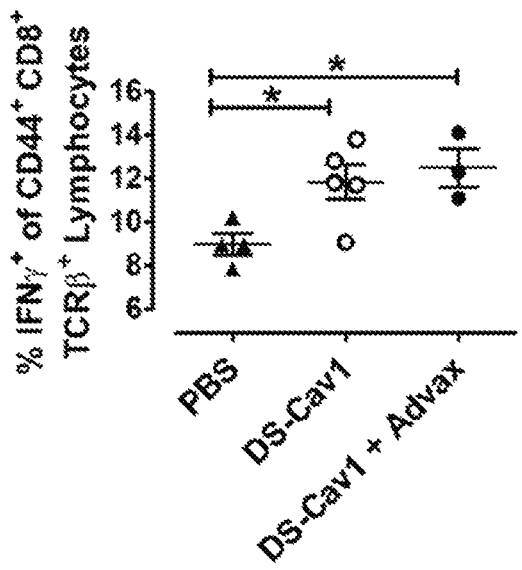

Differential dendritic cell activation of weanlings born to immunized claims influences T cell activation and cytokine production. To assess the influence of differential DC activation in weanlings born to immunized dams, lymphocytes and their capacity to make Th1 (IFNγ) and Th2 (IL-4 and IL-5) cytokines were measured in the BAL at 8 dpi. Activated CD4 and CD8 T cells were reduced in DS-Cav1 and DS-Cav1+Advax-SM weanlings compared to PBS weanlings (FIGS. 8A and 8G). However, the frequency of CD4 T cells making IL-4 and IL-5 was increased in DS-Cav1 weanlings as compared to PBS and DS-Cav1+Advax-SM weanlings (FIGS. 8B through 8D) whereas no significant differences in the frequency of IFNγ were detected between groups (FIG. 8E). No significant differences were observed in the CD4 T cell IFNγ:IL-4 ratio between groups; however, DS-Cav1 weanlings had a trend toward a more dominant Th2-type cytokine profile on re-infection than those from PBS or DS-Cav1+Advax-weanlings (FIG. 8F). Both DS-Cav1 and DS-Cav1+Advax-SM weanlings had a higher frequency of CD4-derived IL-5 and CD8-derived IFNγ production compared to PBS weanlings (FIGS. 8D and 8H). Discrete differences were noted in the T cell response in the digested lung tissue compared to the those in the BAL. Specifically, there was a greater number of CD4 T cells in the lung tissue of DS-Cav1+Advax-SM weanlings compared to the BAL. (FIG. 10A). Moreover, the frequency of ICCS for IFNγ, IL-4, and IL-5 were all greater in DS-Cav1 compared to DS-Cav1+Advax-SM weanlings (FIG. 10B through 10D), whereas CD8 T cell responses and IFNγ cytokine production were similar to those in the BAL between groups (FIGS. 10E and 10F). Taken together, these data show that the increased DC activation/maturation, as measured by CD86 and CD11b expression on DS-Cav1 and DS-Cav1+Advax-SM weanlings in the BAL, coincide with an overall increase in both Th1 and Th2 CD4 ICCS production. Similarly, ICCS of IFNγ in CD8 T cells were also enhanced in weanlings born to immunized dams, regardless of Advax-SM, in concert with DC activation.

Figure 9:
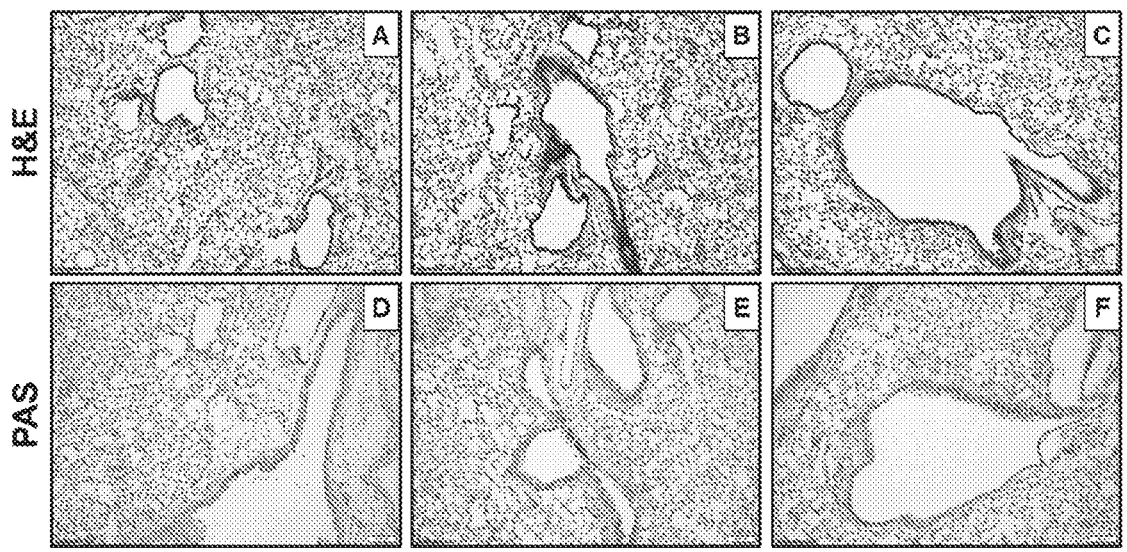
FIG. 9(A-F) are micrographs showing that lung pathology in weanling mice is influenced by maternal vaccination. Weanlings (PND 37) born to immunized dams were challenged with RSV and right lung harvested for histology at 8 dpi. Lungs were stained with H&E (top panels) and PAS (bottom panels) and imaged at 10× magnification; bar indicates 100 µm. From left to right the samples are: PBS (FIGS. 9A and 9D), DS-Cav1 (FIGS. 9B and 9E), and DS-Cav1+ Advax-SM (FIGS. 9C and 9F). Lung sections stained with PAS were scored 0 to 4 for PAS positivity, with 0 having no PAS and 4 being 75-100% PAS+.

Lung pathology in weanling mice is influenced by maternal vaccination. Based on the lymphocyte changes observed in weanlings born to immunized dams, it was determined whether lung pathology in these offspring would be enhanced following viral challenge. At 8 dpi, lung sections from each weanling group showed mild perivascular and peribronchial lymphocytic inflammation with no major differences observed between groups (FIG. 9, top panels), which likely reflects analysis at 8 dpi rather than 4 dpi, which more closely represents peak time of infection. However, quantification of PAS staining showed greater amounts of mucus within the airways of DS-Cav1 and DS-Cav1+Advax-SM weanlings, as compared to PBS weanlings (FIG. 9, lower panels). Mucus was reduced in all groups by 12 dpi, though the differences remained consistent between each of the PBS group (0=90.19%; 1=5.69%; 2=2.17%; 3=1.95%; 4=0%), the DS-Cav1 group (0=82.65%; 1=12.47%; 2=3.01%; 3=1.87%; 4=0%), and the DS-Cav1+Advax-SM group (0=72.92%; 1=12.50%; 2=4.17%; 3=4.17%; 4=6.25%). These results show that maternal immunization influences the host immune response to primary RSV infection resulting in enhanced mucus production in weanlings born to maternally immunized dams.

Discussion

It is shown herein that dams immunized with DS-Cav1+Advax-SM had high pre-challenge RSV neutralizing antibody, comprised of both IgG1 and IgG2a, which translated into sterilizing immunity in 100% of dam lungs when challenged with RSV 5-weeks after the final booster. By contrast, dams immunized with DS-Cav1 alone had lower levels of neutralizing antibody that was of the IgG1 subclass and only partially protective against RSV infection with more than half of the dams having detectable virus at 4 dpi. This is consistent with previously published data showing that DS-Cav1 alone provides only partial protection in adult cotton rats and mice (Sastry et al., *PLoS One*, 2017; 12(10): e0186854; Schneider-Ohrum et al., *J. Virol.*, 2017; 91(8)), but that when combined with an adjuvant, is capable of eliciting sterilizing immunity against RSV challenge (Sastry et al., *PLoS One*, 2017; 12(10):e0186854). Results further showed that poor neutralizing antibody responses associated with unadjuvanted DS-Cav1, as compared to Advax-SM-adjuvanted DS-Cav1, was associated with a strong Th2-biased response to RSV with significant airway inflammation and mucus production in seronegative dams. These results show that a non-Th2-polarizing adjuvant, such as Advax-SM, can be used to improve the safety and efficacy of DS-Cav1 immunization, which is currently being tested alone or in combination with alum adjuvant in Phase I clinical trials (NCT03049488).

Despite having reduced RSV lung titers compared to PBS control dams, results disclosed herein show that DS-Cav1 dams developed VERD with increased airway inflammation and mucus production in association with markedly increased Th2 cytokines in the BAL. Among these cytokines were IL-13 and IL-5, which are heavily involved in the recruitment and survival of eosinophils in the RSV-infected lung in association with VERD (Stier et al., *Ann. Am. Thorac. Soc.*, 2018; 15(Supplement_3):S205-59; Castilow et al., J. Immunology., 2008; 180(4):2376). IL-5, is further associated with airway remodeling processes, such as fibrotic changes and enhanced collagen deposition in the lungs of asthmatics (Tanaka et al., *Am. J. Respir. Cell Molec. Biol.*, 2004; 31(1):62-8; Humbles et al., *Science*, 2004; 305(5691):1776; Lopez et al., *J. Exp. Med.*, 1988; 167(1): 219-24; Bagnasco et al., *Front. Med.*, 2017; 4(135)). In clinical trials, neutralization of IL-5 or blockade of the IL-5 receptor-α with the use of the monoclonal antibodies, mepolizumab and benralizumab, respectively, proved effective in reducing blood and airway eosinophilia, but this reduction did not always improved functional measures of lung physiology in asthmatics (Bagnasco et al., *Frontiers in Medicine*, 2017; 4(135); Flood-Page et al., *Am. J. Respir. Crit. Care Med.*, 2007; 176(11):1062-71). It has been posited that the closely related cytokines, IL-3 and GM-CSF may overcome IL-5 neutralization by mepolizumab, possibly limiting its ability to improve asthma symptoms (Flood-Page et al., *Am. J. Respir. Crit. Care Med.*, 2007; 176(11): 1062-71).

In addition to IL-5, IL-3 and GM-CST share a common β chain (βc) with IL-5 drive eosinophil differentiation in the bone marrow and are central to eosinophil survival, migration, and activation (Lopez et al., *J. Exp. Med.*, 1988; 167(1):219-24; Lopez et al., *J. Clin. Invest.*, 1986; 78(5): 1220-8; Rothenberg et al., *J. Clin. Invest.*, 1988; 81(6):1986-92). In the βc−/− model of acute asthma, knockdown of the common beta receptor subunit for IL-3, IL-5, and GM-CSF significantly reduced airway eosinophilia, AHR, and recruitment of activated T cells to the lungs after allergen challenge, highlighting the close interplay between AHR, eosinophilia, and Th2 immunity (Asquith et al., *J. Immunol.*, 2008; 180(2):1199-206). As disclosed herein, RSV-challenged DS-Cav1 dams had elevated levels of IL-3, IL-5, and GM-CSF in the BAL, in conjunction with airway and pulmonary eosinophilia. These factors, together with elevated concentrations of IL-13 and IL-4, increased IL-4+ CD4 T cells, and increased inflammation and mucus production in DS-Cav1 dams following RSV challenge, show that an AHR-promoting phenotype and are consistent with a Th2-polarized immune response. Importantly, Th2 polarization and VERD were not seen in dams immunized with DS-Cav1 formulated with the non-Th2-polarizing adjuvant, Advax-SM.

Cellular responses associated with VERD continue to focus on eosinophils due to their presence in autopsy samples from the FI-RSV vaccinated children who died as a result of VERD after RSV infection (Kim et al., *Am. J. Epidemiol.*, 1969; 89(4):422-34). The exact contribution of eosinophils to excess inflammation and general pathology of VERD remains uncertain since neutrophils and monocytes comprised a larger proportion of the cellular infiltrate in these post-mortem specimens (Acosta et al., *Clin. Vacc. Immunol.*, 2015; 23(3):189-95; Kim et al., *Am. J. Epidemiol.*, 1969; 89(4):422-34; Prince et al., *J. Gen. Virol.*, 2001; 82(12):2881-8). In the herein disclosed results, both DS-Cav1 and DS-Cav1+Advax-SM dams had higher frequencies of neutrophils and monocytes in the BAL compared to PBS controls, whereas only dams immunized with unadjuvanted DS-Cav1 demonstrated increased lung pathology post-RSV challenge. These data show that the frequency of eosinophils as well as Sig F− inflammatory macrophages producing IL-5 and TNFα in the lung and BAL, rather than the presence of neutrophils or monocytes, contribute more to VERD inflammation. These data are consistent with studies in both cotton rats and mice demonstrating the important role of eosinophils in VERD (Castilow et al., *J. Immunol.*, 2008; 180(4):2376: Green et al., *Comp. Med.*, 2018; 68(1): 31-40).

It was previously shown that chlodronate liposome-mediated depletion of alveolar macrophages impairs viral clearance and significantly influences lung homeostasis during RSV infection of BALB/c mice (Benoit et al., *Clin. Exp. Immunol.*, 2006; 145(1):147-54; Eichinger et al., *Respir. Res.*, 2015; 16:122). However, siglec F− macrophages are a less well characterized cell type that can be identified in the alveolar space and promote inflammation during infection (Janssen et al., *Eur. Respir. J.*, 2016; 48(4):1201-14). Like eosinophils, siglec F− macrophages were significantly elevated in the BAL of DS-Cav1 dams (FIG. 4D) and produced higher levels of IL-5 and TNFα (FIG. 4), compared to dams immunized with DS-Cav1+Advax-SM or PBS, showing they also contribute to the recruitment of eosinophils and VERD in DS-Cav1-immunized dams.

Multiple models of RSV vaccination have investigated the importance of CD4+ T cells in the development of VERD (Connors et al., *J. Virology*, 1992; 66(12):7444-51; Johnson et al., *J. Leukocyte Biol.*, 2008; 84(3):748-59; Knudson et al., *PLOS Pathogens*, 2015; 11(3):e1004757). Results shown herein are consistent with a study by Knudson et al., which demonstrated the critical role of Th2 CD4+ T cells in mediating VED, including weight loss, mucus hypersecretion, and AHR in FI-RSV-immunized mice (Knudson et al., *PLOS Pathogens*, 2015; 11(3):e1004757). Similarly, CD4+ T cells and their production of IL-4 and IL-13 were shown to be important drivers of VERD in a model of immunization with vaccinia virus expressing RSV G glycoprotein. In fact, IL-13, a potent Th2 cytokine, was shown to be sufficient to induce mucus hypersecretion and AHR in naïve mice (Wills-Karp et al., *Science*, 1998; 282(5397):2258-61), while also promoting the recruitment of eosinophils to the lung parenchyma and airway in VERD (Castilow et al., *J. Immunol.*, 2008; 180(4):2376).

CD8+ T cells are important in the clearance of RSV during primary infection (Graham et al., *J. Clin. Invest.*, 1991; 88(3):1026-33.) and play a role in preventing VERD in models of RSV vaccination (Hussell et al., *Eur. J. Immunol.*, 1997; 27(12):3341-9; Olson et al., *J. Immunol.*, 2008; 181(11):7958; Olson et al., *J. Immunol.*, 2007; 179 (8):5415; Stevens et al., *Viral Immunol.*, 2009; 22(4):243-51). Stevens et al. suggested that memory CD8+ T cells reduce pulmonary eosinophilia without modulating the CD4+ T cell response (Stevens et al., *Viral Immunol.*, 2009; 22(4):243-51), while others have suggested that CD8+ T cells are important modulators of CD4+ T cells and eosinophil recruitment (Hussell et al., *Eur. J. Immunol.*, 1997; 27(12)3341-9; Olson et al., *J. Immunol.*, 2008; 181(11): 7958). Ultimately, the number of RSV-specific CD8+ T cells producing IFNγ is important in controlling Th2-driven pathology (Olson et al., *J. Immunol.*, 2008; 181(11):7958). Results disclosed herein show that DS-Cav1+Advax-SM immunization increased the number of CD8+ T cell in the BAL with a higher ratio of IFNγ+/IL-4+ TCRβ+ lymphocytes and increased RSV F85-93-specific CD8+ T cells.

Despite enhanced RSV viral clearance, memory CD8+ T cells directed toward single RSV epitopes can induce severe pathology upon RSV exposure. Morbidity and immunopathology in this model were attributed to rapid production of IFNγ by these memory CD8+ T cells, which were primed in the absence of RSV-specific CD4+ T cells and antibodies (Schmidt et al., *PLoS Pathog.*, 2018; 14(1):e1006810). While potential for pathogenic memory CD8+ T cell responses should be considered when evaluating RSV vaccine candidates, results disclosed herein show enhanced RSV-specific CD8+ T cell responses do not cause excess pathology when accompanied by high titers of RSV-specific neutralizing antibody and increased proliferating CD4+ T cells (FIG. 5F), both of which provide regulatory signals that likely temper memory CD8+ T cell responses. Thus, it is shown herein that maternal DS-Cav1+Advax-SM immunization primes for enhanced CD8+ T cell RSV F-specificity and IFNγ production that in combination with a reduced Th2 bias, can control the virus, prevent mucus production, and mitigate recruitment of inflammatory eosinophils and macrophages following RSV challenge.

The precise mechanism of VERD remains unknown; however, FI-RSV studies suggest that poorly neutralizing antibody contributes to immune complex deposition in the small airways leading to exacerbated Th2-mediated inflammation with RSV infection (Polack et al., *J. Exp. Med.*, 2002; 196(6):859-65). To date, there have been no reports of VERD in RSV seropositive individuals, suggesting that previous RSV exposure may mitigate the risk (Higgins et al., *Vaccine*, 2016; 34(26);2870-5; Blanco et al., *Vaccine*, 2017; 35(32):3951-8; Waris et al., *J. Virol.*, 1997; 71(9):6935-9). Regarding safety to offspring, maternal immunization models suggest that the transfer of maternally-derived antibody establishes a temporary seropositive-like environment in offspring. Seroprevalence studies further show that the decay of RSV-specific-maternal antibodies is rapid over the first six months of life with a mean duration of about 4.7 months (Nyiro et al., *PLoS One.*, 2017; 12(5):e0177803). However, seroprevalence remains low between 5-11 months of age, a discrepancy which likely contributes to the development of severe RSV disease at an early when maternally-derived antibody should provide protection (Meissner et al., *Pediatr. Infect. Dis. J.*, 2004; 23(3):284-5; Hall et al., N. E. J. M., 2009; 360(6):588-98; Stevens et al., *Viral Immunol.*, 2008; 21(2):133-40); Maternal immunization strategies to boost the passive transfer of neutralizing antibody to the offspring should help expand the window of protection, but it remains unclear how primary RSV infection will influence immune priming in infants when it occurs as vaccine-mediated maternal antibody is waning.

Figure 11A:
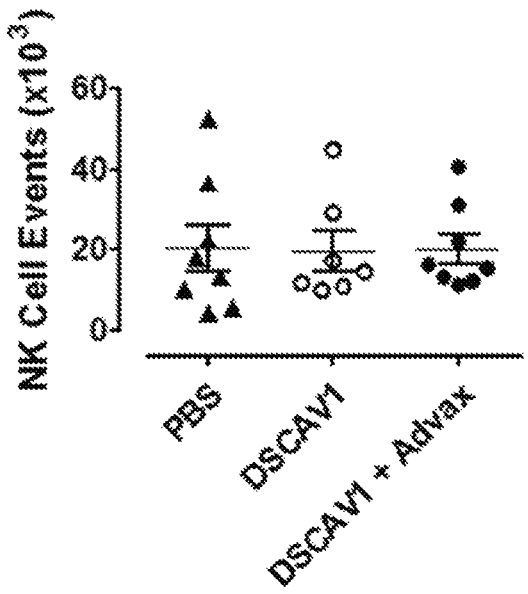
FIG. 11(A-D) is a set of graphs showing Innate cellular responses of dams and their offspring are influenced by maternal immunization. Dams (post-partum day; PPD28) and weanlings (PND35) born to immunized dams were challenged with RSV and BAL cells harvested at 4 dpi. The total number of NK cells events (CD3− or TCRβ−/DX5+) in the SSClo gate (FIGS. 11A and 11B) and percentages of cytolytic NK cells (CD11b+ CD27−) expressing CD16 (FIGS. 11C and 11D) were compared between dam (FIGS. 11A and 11C) and weanling (FIGS. 11B and 11D) immunization groups. Individual symbols within each group represent individual animals, lines represent the mean of ≥4 samples per group±SEM. Comparisons between groups were made using ANOVA with a Tukey post-test; *p<0.05, p<0.01, *p<0.001.
Figure 11B:
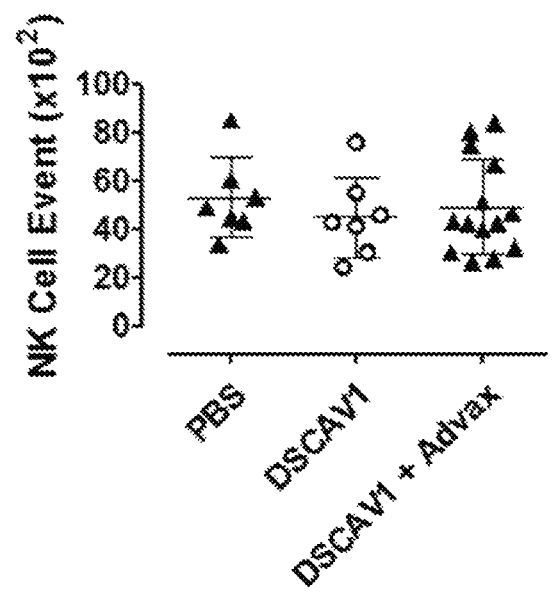
Figure 11C:
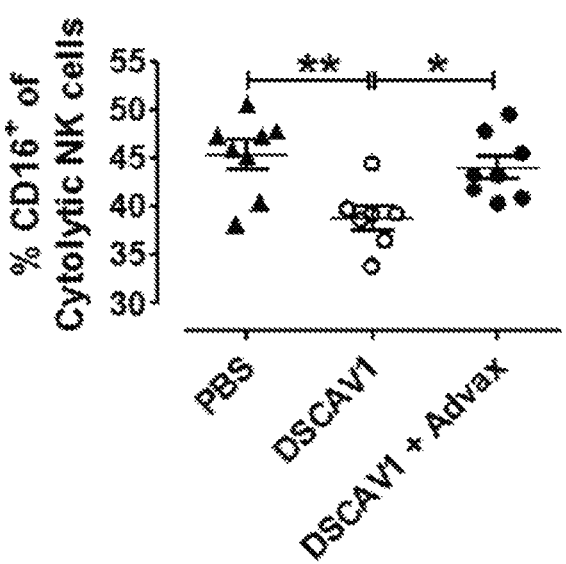
Figure 11D:
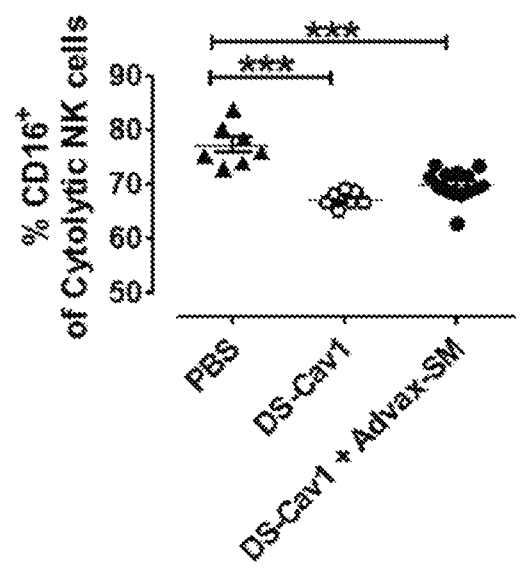

Results disclosed herein show that a majority of offspring from DS-Cav1+Advax-SM dams were completely protected from RSV, both immediately after birth, as well as 2 weeks after offspring were weaned and the transfer of maternal antibodies via breast milk had ceased. However, the frequency of DS-Cav1+Advax-SM infants and weanlings with neutralizing antibody levels≥40 was lower than the frequency of infants and weanlings with undetectable virus in their lungs. This discrepancy may indicate a lack of sensitivity in the neutralizing antibody assay or may suggest a role for non-neutralizing antibodies in controlling infection through processes such as ADCC. In support, the expression of FcγRIII (CD16+) on cytolytic NK cells was significantly reduced in DS-Cav1+Advax-SM and DS-Cav1 weanlings (FIGS. 11A and 11B), as well as in unadjuvanted DS-Cav1 dams that was not seen in the PBS group following RSV infection (FIGS. 11C and 11D). Loss of PcγRIII on NK cells has been shown to occur following ADCC as a result of membrane-type 6 matrix metalloproteinase (MMP6) [67] and/or metalloproteinase-17 (ADAM-17) (Goodier et al., Front. Immunol., 2016; 7:384; Romee et al., Blood, 2013; 121(18):3599) activity, inducing receptor shedding to minimize inflammation.

Greater levels of IgG1 in DS-Cav1 weanlings, as compared to increased IgG2a in DS-Cav1-Advax-SM weanlings, reflect the Th2 bias observed in DS-Cav1− versus DS-Cav1+Advax-SM-immunized dams, respectively. Kwon et al, previously reported that maternal Th2 biased responses in FI-RSV-immunized dam, including Th2-cytokine production, lung inflammation and mucus production, were not conferred to 5- or 7-week-old offspring after viral challenge and that minimal cytokine production was detected in the lungs of the offspring (Kwon et al. Antiviral Res., 2014; 104:1-6). In the herein disclosed results, it is also shown that airway inflammation was minimal in 5-week-old offspring, though the 8-day time point did not capture peak inflammation. However, unlike the previous study, mucus production was markedly enhanced in both DS-Cav1 and DS-Cav1+Advax-SM weanlings compared to PBS weanlings at 8 dpi (FIG. 9), showing that offspring born to immunized dams may have an increased risk of pulmonary pathology following primary RSV infection. The role of DC activation and T cell responses following viral challenge in the offspring of immunized dams was evaluated, raising interesting questions regarding the role of IgG subtypes in the protection mediated by maternal immunization. The pre-challenge serum of DS-Cav1+Advax-SM weanlings was dominated by IgG2a antibodies, which correlated with higher neutralization titers, sterilizing immunity, and enhanced DC maturation. Studies investigating the link between pathogen-pattern recognition receptors, like Toll-like receptors (TLRs), and pathogen clearance through IgG immune complex (IgGIC) formation, along with engagement of Fc receptors showed the critical role TLR4 plays in the activation of phagocytic cells via its interaction with IgGIC bound to FcγRIII (Rittirsch et al., PLOS Pathogens, 2009; 5(6):e1000464). RSV F protein is a known TLR4 agonist (Collins et al., J. Virol. 2008; 82(5):2040-55); therefore, the improved RSV neutralization by IgG2a following RSV challenge of DS-Cav1+Advax-SM weanlings may lead to immune complex formation that is detected by FcγRIII and TLR4 on dendritic cells resulting in their activation.

Results disclosed herein further show that DS-Cav1 and DS-Cav1+Advax-SM weanlings had a greater frequency of CD11b+CD103− DCs in the BAL compared to PBS weanlings, regardless of their maternally-derived IgG subtype. When expressed in the draining lymph nodes, CD11b+ CD103−DCs have been shown to favor antigen presentation to CD4+ T cells over CD8+ T cells and promote Th2 CD4 T cell responses (Sastry et al., PLoS One., 2017; 12(10): e0186854; Hussell et al., Eur. J. Immunol., 1997; 27(12): 3341-9; Ruckwardt et al., Mucosal Immunol., 2018; 11(1): 186-98; Malloy et al., J. Immunol., 2017; 198(1):394-403; Plantinga et al., Immunity, 2013; 38(2):322-35; Ruckwardt et al., PLoS Pathog., 2014; 10(2):e1003934), however, it is unclear if DC phenotypes in the BAL parallel those in the lung or lymph nodes. To this point, CD4 and CD8 T cell numbers in the BAL were reduced in DS-Cav1 and DS-Cav1+Advax-SM weanlings in parallel with the increase in neutralizing antibody titers, reduced viral lung titers, and greater frequency of mature DCs in the BAL. Similarly, intracellular Th2 cytokines, IL-4, IL-5, and IFNγ stained at a higher frequency in CD4 T cells in the BAL of DS-Cab1 and DS-Cav1+Advax-SM weanlings compared to PBS weanlings, indicating greater activation and engagement of CD4 T cells (FIG. 8). Moreover, the ratio of IFNγ to IL-4 ICCS in CD4 T cells suggests that DS-Cav1 trended toward a more prominent Th2 response, though statistical significance was not achieved, likely due to the low number of animals in these groups (FIG. 8F). Lastly, both DS-Cav1 and DS-Cab1 Advax-SM weanlings had an increased percentage of intracellular IFNγ in CD4 (non-significant) and CD8 T cells compared to PBS weanlings. Taken together, these data show that enhanced DC activation paralleled the observed increases in T cell response following viral infection in weanlings born to immunized dams that exceeded the response in PBS weanlings, which may reflect the accumulation of IgGIC and activation of local DCs. Interestingly, a greater number of CD4 T cells were retained in the lung as opposed to the BAL in the DS-Cav1+Advax-SM weanlings as compared to PBS and DS-Cav1 weanlings (FIG. 10), which may suggest a differential expression of the integrin, VLA-4 induced on CD4 T cells in DS-Cav1+Advax-SM weanlings (Siegelman et al., J. Clin. Invest., 2000; 105(5): 683-91).

Increased PAS staining at 8 dpi in the airways of both DS-Cav1 and DS-Cav1+Advax-SM weanlings likely reflect enhanced T cell activity compared to PBS weanlings. A recent study by Stier and Peebles suggest that thymic stromal lymphopoietin (TSLP) derived from respiratory epithelial cells upon viral infection stimulates IL-33 and IL-25 that than induce innate lymphocyte 2 (ILC)-mediated IL-13 to drive excess mucin production (Stier et al., Ann. Am. Thorac. Soc., 2018; 15(Supplement_3):S205-S9).

Taken together, these results demonstrate that maternal immunization has important consequences on the offspring's immune response to primary RSV infection, regardless of maternal antibody potency and Th1 vs Th2 polarizing effects of associated adjuvants. The pathology of VERD mirrors many facets of severe RSV disease that often occurs in, otherwise healthy, infants following primary RSV, including reduced T cell numbers with increased cytokine production and mucus overproduction. However, such responses in the face of waning antibody calls into question how T cell priming, and subsequent immune responses, such as airway hyperresponsiveness (AHR), may be influenced. A recent study by Schneider-Ohrum et al. used a cotton rat model to show that deescalating doses of pre and post conformational forms of RSV F subunit immunogens induced greater alveolitis than higher doses. Consistent with their findings, the mouse model used herein, which recapitulated waning antibody in weanlings born immunized dams, showed enhanced disease in the form of increased mucus production, when weanlings were infected for the first time as antibody was waning. The lack of extensive lung inflammation in these offspring can be attributed to the later time point (8 dpi) in which lungs were harvested. Though the mechanism of enhance disease during waning or low antibody remains unclear, the increase in DC activation and subsequent T cell responses, and enhanced mucus production shown in these studies are likely heavily influenced by maternal Ab-Ag ICs binding to FcγRs expressed on DCs. The lack of a similar response in antibody-nave weanlings support this. Thus, despite ongoing clinical trials designed to evaluate the safety and efficacy of maternal immunization (NCT02247726; NCT02624947), it remains unclear how infants may respond immunologically to natural RSV infection as maternal antibody begins to wane and emphasizes the importance of understanding how Ab-Ag ICs may affect the immune imprint and subsequent RSV immune responses. Functional studies will be important in future studies to reveal the impact of maternal immunization on lung physiology and risk of long-term AHR.

Materials and Methods

Mice, vaccination, and virus. Balb/c male and female breeders were purchased from The Jackson Laboratory (Bar Harbor, Me.) at 7 weeks of age. At time of co-housing, females were immunized (prime) via intramuscular (i.m.) injection with 50 μL of vehicle (PBS), DS-Cav1 alone (10 μg/mouse) (McLellan et al., *Science,* 2013; 342(6158):592), or in combination with Advax-SM (DS-Cav1+Advax-SM; Advax-SM™, 1 mg/mouse) (Honda-Okubo et al., *Vaccine,* 2014; 32(36):4651-9.). A week later, mice were bred in-house (Empey et al., *PLoS One,* 2012; 7(7)). In the second week of gestation (21 days post-prime), female mice were boosted i.m. with their respective vaccine. Mice were challenged intranasally (i. n.) with $5 \times 10^5$ plaque forming units (PFU) of RSV Line 19 (RSV L19) per gram of body weight under isoflurane anesthesia (Empey et al., *PLoS One,* 2012; 7(7)). Danis were challenged at 15 weeks of age (53 days post-prime/32 days post-boost), infants challenged at 5-6 post-natal days (PND), and weanlings were weaned at 3 weeks of age and challenged 2 weeks later. At 4 days post-RSV challenge, mice were sacrificed using 100% isoflurane and cervical dislocation per approved IACUC protocols. Propagation of RSV L19 and viral titer quantification was performed (Graham et al., *J. Med. Virol.,* 1988; 26(2): 153-62).

Cell preparation, cytokine analysis, and flow cytometry. First wash (FW) and bronchoalveolar lavage (BAL) were collected by instilling HBSS+30 μM EDTA into the alveolar space. The right lung (RL) was harvested and enzyme-digested into a single cell suspension (Empey et al., *Inject. Immun.,* 2007; 75(7):3382-93). FW samples were centrifuged, and the soluble fraction was separated and stored at −80° C. for cytokine analysis. Cytokine concentration was determined using the Bio-Plex Pro™ Mouse Cytokine 23-plex Assay (BioRad, Calif.), per manufacturer's protocol. The cellular components of the BAL, and RL were processed for surface and intracellular flow cytometric analysis. Each BAL and RL sample represents a single weanling and dam mouse. 2-3 infant BAL samples were pooled to generate a single flow cytometry sample. Cells were surface stained with the following antibodies: CD11c-N418, Ly6G-1A8, I-A/I-E-M5/114.15.2, TCRβ-H57-597, CD19-6D5 (Biolegend, Calif.), CD11b-M1/70, Siglec F E50-2440, F4/80-T45-2342, I-A[d]-AMS-32.1, CD49b-DX5, CD27-La3A10, CD16/32-2.4G2, CD3-17A2, CD25-PC61, CD8α-53-6.7, CD4-GK1.5, CD44-IM7 (BD Biosciences, Calif.), CD204-REA148 (Miltenyi Biotec, Bergisch Gladbach, Germany). Cells were fixed and permeabilized for intracellular staining with True-Nuclear™ Transcription Factor Buffer Set (Biolegend, Calif.), BD CytoFix/CytoPerm™ Solution Kit (BD Biosciences, Calif.), or Foxp3 Transcription Factor Staining Buffer Kit (ThermoFisher Scientific, MA), according to manufacturers' protocol, for the following antibodies: CD206-C068C2, Tbet-4B10, GATA3-16E10A23, TNFα-MP6-XT22, IL-5-TRFK5, IL-4-11B11, IL-2-JES6-5H4 (Biolegend, CA), RORγt-Q31-378, Foxp3-MF23, Ki67-B56, IL-12 (p40/p70)-C15.6 (BD Biosciences, CA), IL-6-MP5-20F30 (Thermo-Fisher Scientific, MA). Where indicated, BAL samples were incubated with RSV A Strain F-protein 85-93 MHC I pentamer (H-2kd KYKNAVTEL; Proimmune, FL). Samples were run on a BD LSRFortessa. Data were analyzed using FlowJo V10 software (FLOWJO, LLC, OR).

Histopathology and viral titer determination. At 4 days post-challenge, RLs were gravity filled with 10% formalin (Eichinger et al., *Respir. Research,* 2015; 16:122). Preserved lungs were stained and processed by a histology core. Hematoxylin and Eosin (H&E) and Periodic Acid-Schiff (PAS) stains were used to identify inflammation and mucus accumulation, respectively. PAS staining was scored by two individuals blinded to treatment groups (Empey et al., *PLoS One,* 2012; 7(7)), All airways (average 48) were scored in each tissue section according to the following scale: 0=no PAS+ cells; 1=1-25% PAS+ cells; 2=26-50% PAS+ cells; 3=51-75% PAS+ cells; 4=76-100% PAS+cells. Left lungs (LL) were snap-frozen and stored at −80° C. until lung titers could be determined (Graham et al., *J. Med. Virol.,* 1988; 26(2):153-62).

Plaque reduction neutralization test (PRNT). Pre-challenge blood was collected from dams at 50 days post-prime (3 days prior to RSV challenge) via submandibular bleeding (Golde et al., *Lab. Animal,* 2005; 34:39). Pre-challenge serum was collected from weanling groups (PND 37) immediately prior to RSV challenge. Post-challenge blood was collected at 4 days-post RSV challenge via severing of abdominal aorta (infants) or cardiac puncture (weanling and dams) at time of sacrifice. Serum was separated using Gel-Z Serum Separator Tubes (Sarstedt, Rommelsdorf, Germany), heat-inactivated at 56° C. for 30 minutes, and stored at −80° C. until neutralizing titers were determined. The following protocol was adapted from a previously described RSV PRNT assay (Fuentes et al., *Vaccine,* 2013; 31(37):3987-94). Heat-inactivated antisera was initially diluted in 10% FBS-DMEM at 1:40 (pre-challenge serum) or 1:20 (post-challenge serum) dilutions, then 2-fold serially diluted in a 96-well plate. RSV L19 (1500 PFU/well) was added and the antisera/virus mixture was incubated at 37° C. for 1 hour. Virus-antisera mixture (100 μL) was added to $1.5 \times 10^4$ HEp2 cells in each well of a 96-well plate and incubated at 37° C. for 3 days at 5% $CO_2$. Plates were washed with PBS and fixed with acetone at 4° C. for 20 minutes. Goat anti-RSV polyclonal antibody (AB1128; Fisher Scientific, NH) was added at a 1:4000 dilution and incubated at room temperature (RT) for 1 hour. HRP-conjugated donkey anti-goat IgG (STAR88P; BioRad, CA) was then added at a 1:4000 dilution and incubated at RT for 1 hour. TMB substrate (ThermoFisher Scientific, MA) was added and color was allowed to develop for 5 to 7 minutes, at which time 1M sulfuric acid was added to stop the reaction. Optical density was measured at 450 nm using the ELx800™ Plate Reader (BioTek, VT). Reciprocal serum dilutions at which 50% of RSV L19 was neutralized in relation to control wells was graphed.

RSV-specific IgG isotype assay. RSV-specific IgG subtypes were measured as previously described (Quail F-S, et al., *J. Infectious Diseases,* 2011; 204(7):987-95). Immulon high-binding 96-well microtiter plates were coated with 100 μL of purified RSV L19 virus ($3 \times 10^5$ pfu) in binding buffer at 4° C. overnight. After washing steps and blocking for 2 hours at 37° C. with blocking buffer (3% BSA in PBS), antisera was diluted (dams, 1:100; weanlings, 1:20) in blocking buffer and incubated in triplicate overnight at 4° C.

The plates were then incubated with HRP-conjugated IgG1 (1:5000) or IgG2a (1:2500) goat anti-mouse secondary antibodies at 37° C. for 90 minutes. TMB substrate (ThermoFisher Scientific, MA) was added and color was allowed to develop for 30 minutes at 37° C. The optical density was read at 450 nm using the ELx800™ Plate Reader (BioTek, VT). Optical densities were graphed after subtracting background OD from triplicate wells incubated with blocking buffer.

Statistical Analysis. Results in the figures are displayed as the mean±SEM for individual samples. ANOVA with a Tukey post-test was used to test for statistically significant differences between vaccination groups using GraphPad Prism software (La Jolla, CA).

Example 2

Cotton Rat Model for the Evaluation of RSV Vaccines and Therapeutics

The effect of adding an adjuvant, 2% Alhydrogel (ALH) or Advax (4 mg/CR), to the formulation was evaluated. A prime-boost strategy was used and vaccine was administered by intramuscular injections. On day+39 following RSV/A/Tracy challenge (day+35), lung lavage fluids from the two larger lobes of the right lung and nasal wash fluids was obtained and RSV titers determined by plaque assay. One lobe of the right lung will be flash-frozen in liquid $N_2$ and stored at −80° C. The entire left lung was fixed in 10% formalin and sent to Baylor College of Medicine's Center for Comparative Medicine (CCM) for histopathology. Serum samples were obtained throughout the experiment and used to measure neutralizing antibody activities against RSV/A/Tracy and RSV/B/18537.

Results: Whether the vaccine candidate contained the ALH or Advax adjuvant, both the 2 and 10 μg of a DT-preF protein/cotton rat (DT-Cav1 having K226Y/V185Y/N428Y/S190F/V207L mutations) were very effective in reducing RSV/A/Tracy in the lungs by approximately 4 $\log_{10}$ PFU/g lung and nose by approximately 1.5 $\log_{10}$ total PFU compared to the saline control. All of the vaccines generated RSV/A/Tracy-specific neutralizing antibody following a second (boost) vaccination in these naïve cotton rats and were greater than when generated by live RSV/A/Tracy infection on day 0. At the time of virus challenge (day 35) the neutralizing antibody titers were statistically greater when the preF vaccines were adjuvanted with Alhydrogel (ALH) compared to those adjuvanted with Advax. This difference between the adjuvant was reflected in a greater cellular infiltrate into the lungs with ALH than with Advax.

Conclusion: The DT-preF adjuvanted vaccines at either the 2 μg or 10 μg of PreF protein with either Alhydrogel or Advax provided a robust immune response in RSV naïve cotton rats upon a second dose. All DT-preF adjuvanted vaccines provided excellent protection against RSV/A/Tracy replication in the lungs and significant but moderate reduction in the nose and generated RSV/A/Tracy-specific serum neutralizing antibody. The increase in pulmonary histopathology associated with these vaccines suggests caution in RSV naïve populations, however, the elderly adult population would likely be a suitable target group for DT-preF adjuvanted vaccines.

Vaccination Schedule: Vaccination (IM) was performed (Day 0) with a boost at 21 days (Day 21) and virus challenge 14 days later (Day 35). Mice were sacrificed 4 days later (Day 39).

Cotton Rats: All animals were challenged with live RSV/A/Tracy on Day+35 Group 1, 5 Cotton rats (CR) injected IM with Saline (positive virus infection control) Group 2, 5 CR infected with live RSV/A/Tracy on Day 0 ("gold standard") Group 3, 5 CR injected IM with 2 μg DT-preF and adjuvanted with 100 μg of 2% ALH/CR Group 4, 5 CR injected IM with 10 μg DT-preF and adjuvanted with 100 μg of 2% ALH/CR Group 5, 5 CR injected IM with 2 μg DT-preF and adjuvanted with 4 mg of Advax/CR Group 6, 5 CR injected IM with 10 μg DT-preF and adjuvanted with 4 mg of Advax/CR Cotton Rats (30 CR): CR were ~75-150 g body weight (as determined by age at start). Body weight was determined at end of experiment, See Table 3. Animal body weight, age and sex distribution were as similar as possible across all groups at the start. Experiments were performed utilizing NIH and United States Department of Agriculture guidelines. The Public Health Service Policy on Humane Care and Use of Laboratory Animals, and experimental protocols approved by the Baylor College of Medicine's investigational Animal Care and Use Committee (IACUC).

Virus: RSV/A/Tracy (RSV/A/Tracy) (P3 w. p. Mar. 13, 2015), $1.21\times10^5$ PFU intranasally (100 μL) to cotton rats lightly anesthetized with isoflurane. After inoculation on days 0 (group 2) and day 35 (all groups) virus inoculum was back-titered to confirm initial concentration ($\log_{10}$ $TCID_{50}$/mL).

Avatar Biotechnologies Formulation instructions for mixing DT-preF and each of the adjuvants: ALH (stored at RT [21° C.]; Advax (stored at 4° C.). DT-PreF stock protein concentration was: 160 μg/mL in PBS (stored at −80° C.). All steps were performed under a sterile hood.

The following instructions were used for Alhydrogel 2% (Aluminium hydroxide gel; ALH) formulation (DOSE=100 μL per animal, Instructions for 7 doses-700 μL total):

1) Thaw protein samples on wet ice.
2) For the 10 μg dose, dilute protein to a concentration of 105.26 μg/mL in PBS (665 μL total, 437 μL DT-PreF, 228 μL PBS).
3) For the 2 μg dose, dilute protein to a concentration of 21.05 μg/mL in PBS (665 total, 87.4 μL DT-PreF, 577.6 μL PBS).
4) invert protein sample to mix.
5) Thoroughly mix Alhydrogel (Alhydrogel, 2%, Brenntag) by inversion.
6) Open Alhydrogel bottle and pipette 35 μL into each dose, mixing thoroughly by hand to make a homogeneous suspension.
7) Before vaccination, mix formulated solution several times and repeat before every injection to ensure a homogeneous solution.

The following instructions were used for Advax (lot# 5340) formulation (DOSE=1.15 μL per animal, Instructions for 7 doses-805 μL total):

1) Thaw protein samples on wet ice.
For the 10 μg dose, dilute protein to a concentration of 133 μg/mL in PBS (525 total, 436.4 μL DT-PreF, 88.6 μL PBS).
3) For the 2 μg dose, dilute protein to a concentration of 26.6 μg/mL in PBS (525 total, 87.3 μL DT-PreF, 437.7 μL PBS).
4) Resuspend Advax (Vaxine, 100 mg/mL) thoroughly by vortexing for 1 min.
5) If using a needle through the rubber stopper, sterilize with 70% EtOH prior to inserting the needle, otherwise, remove rubber stopper manually under sterile conditions.

6) Pipette 280 μL of the Advax solution (injected amount, 4 mg/CR) into each dose, mixing thoroughly by hand to make a homogeneous suspension.

7) Before vaccination, mix formulated solution several times and repeat before every injection to ensure a homogeneous solution.

IM Injections: DT-preF plus adjuvant: 100 μL DT-preF plus ALH (groups 3, 4) or approx. 115 μL of DT-preF plus Advax (groups 5, 6) were injected (tuberculin syringe) into the area of the left tibialis anterior (TA) muscle (TM). The alternate leg was used for the second vaccination (day+21 boost).

Serum Samples for Antibody Determinations: On day 0, blood was obtained from the orbital plexus of one cotton rat in each group. On all other indicated days, blood was obtained from all of the cotton rats (5 CR/group; 6 groups).

Procedures and Assays:

Collection of organs and samples for virus titra tons and histopathology. Following euthanasia with $CO_2$, the right lung was tied off and the left lung used for histopathology. Two lobes from the right lung were removed and rinsed in sterile water to remove external blood contamination and weighed. The same two right lobes were transpleurally lavaged using 3 mL of Iscove's media with 15% glycerin mixed with 2% FBS-MEM (1:1, v:v) in a 3 mL syringe with a 26G⅜ needle and injecting at multiple sites to totally inflate the lobe. Lavage fluid was recovered by gently pressing one inflated lobe flat and used to transpleurally lavage the other lobe following the same technique. The lavage fluid was collected and stored on ice until titered. One lobe of the right lung was flash-frozen in liquid $N_2$ and stored at −80° C. For nasal washes of the upper respiratory tract, the jaws were disarticulated. The head was then be removed and 1 mL of Iscove's media with 15% glycerin mixed with 2% FBS-MEM (1:1, v:v) was pushed through each naris (total of 2 mL). The effluent was collected from the posterior opening of the pallet and stored on ice until titered. Samples were frozen before titration at the end of sample collecting.

RSV Tracy lung lavage titers (PFU/g lung) and nasal wash titers (total PFU). Plaque assays were performed using 24-well tissue cultures plates containing nearly confluent monolayers (~$2\times10^5$ cells; well) of HEp-2 cells prepared in 10% FBS 24 h prior to assay start. Dilutions (serial $\log_{10}$) were made of the test samples. A 0.2 mL sample of each was then added to wells in duplicate and allowed to adsorb for 90 min with occasional gentle agitation. After inoculum was removed, the monolayers will be overlayed with 0.75% methylcellulose in MEM containing antibiotics, vitamins and other nutrients. Tissue culture and positive virus controls will be included in each assay. The plates were placed in a 36° C., 5% $CO_2$ incubator. Day 6+1 day, plates were stained with 0.01% crystal violet/10% formalin solution (approximately 1.5 mL/well) and allowed to sit for 24-48 h at room temperature. Wells were rinsed with water. Plaques when present were easily visible (clear circles on a very dark blue background). All plaques in wells containing between approximately 20 and 100 plaques were enumerated, averaged, and virus titers calculated as total $\log_{10}$ PFU for nasal wash fluid or $\log_{10}$ PFU/g of tissue for lungs or other organs. Lower limit of detection by this method is 0.70 $\log_{10}$ total PFU or approx. 1.4 $\log_{10}$ PFU/g lung tissue, respectively.

Collection of lungs for histopathology. Following euthanasia with $CO_2$, the left lung was isolated intact, rinsed and perfused with 10% neutral buffered formalin (27 cm pressure for approximately 2 hours). Tissues were stored in formalin. The left lung was used for histopathology.

Evaluation of histopathology. Histopathology was evaluated based on total area of involvement and severity for the following parameters: 1) Peribronchial mononuclear inflammatory cell infiltrates, 2) Bronchiolitis, 3) Bronchiolar eosinophilia, 4) Alveolitis and 5) Perivascular mononuclear inflammatory cell infiltrates. A scale of 0 to 4+ was used for each score. Results were presented for individual parameters and as a cumulative (summary) effect of the histopathology for each cotton rat lung.

Anti-RSV neutralizing antibody on days 0, 21, 35, and 39. Tests for RSV antibodies were performed at Baylor College of Medicine (BCM). Tests for serum neutralizing antibodies to RSV/A/Tracy and RSV/B/18537 were performed in 96-well microtiter plates with HEp-2 cells. Plaque purified RSV's were used in the microneutralization (Nt) assay. Samples were heat inactivated at 56° C. for 30 min Serial two-fold dilutions in duplicates starting at 3 $\log_2$ were performed to determine the neutralizing antibody (Ab) titer for each sample. Neutralizing antibody titer was defined as the serum dilution at which>50% reduction in viral cytopathic effect (CPE) was observed. CPE is defined as tissue destruction and was determined visually after the wells are fixed with 10% neutral buffered formalin and stained with crystal violet. Neutralizing antibody (NtAb) titers were categorical log numbers and not continuous values. The lowest detectable NtAb titer is 2.5 $\log_2$. Samples with non-detectable Nt. Ab titers were assigned a value of 2 $\log_2$. Nt Ab titers are reported in multiples of 0.5 $\log_2$ (e.g., 2.5, 3.0, 3.5, 4.0, etc.). If a sample had an NtAb titer that is equal to or exceeds the upper limit of the test (>14 $\log_2$), that sample was retested so that the NtAb titer can be determined by extending the dilutions to 26 $\log_2$. As an internal standard, palivizumab was included at 40 μg/mL.

Statistical analyses. Initially, viral load or RSV-specific neutralizing antibody levels between controls and vaccine groups were analyzed with loge-transformed viral titers or with loge-transformed antibody titers using Excel's Student t test, two-tailed. Additional comparisons were analyzed by ANOVA using InStat3 (GraphPad) with post-hoc Tukey comparisons. See Table 2.

Histopathology Results:

1) Summary of Group Histopathology % Area (A) of Involved (FIG. 16): Area for both concentrations of preF with ALH (groups 3 and 4), involvement was greater than observed with saline (group 1) ($P<0.05$; ANOVA).

2) Summary of Group Histopathology of Severity (5) Involved (FIG. 16): Severity at a concentration of 10 μg preF with ALE (group 4), involvement was greater than observed saline (group 1) ($P<0.05$; ANOVA).

3) Estimate of Overall Histopathology Involved (A score×S score) (FIG. 17): Overall A×S score at a concentration of 2 μg preF with ALH, total involvement was greater than observed in the saline group ($P<0.05$; ANOVA).

4) An assessment of the number of animals that did not have any lesions (i.e., score of 0) indicates that compared to saline treated (control group 1; 4/5 CR) group 2 ($P=0.524$; 2/4 CR) and groups 5 and 6 ($P=0.206$; 1/5 CR) were not statistically different, but that groups 3 and 4 ($P=0.048$; 0/5 CR) were significantly different (Fisher's Exact Test, two-sided).

Deviation from protocol. Cotton rat 2B was found dead in its cage on day 9. Cause of death was unknown.

Effect of DT-preF adjuvanted with Alhydrogel 2% or Advax on RSV/A/Tracy titers in nasal wash fluids. Compared to saline controls (group 1) infection with live RSV/A/Tracy on day 0 (group 2) reduced titers by 4.42 $\log_{10}$ total PFU ($P<0.00001$; Student t test, two-tailed) (FIG. 12, Table 4). All of the vaccine combinations reduced virus titers by 1.37 to 1.77 $\log_{10}$ total PFU (P<0.00024; Student t test, two-tailed). There were no statistical differences between the vaccine combinations.

Effect of DT-preF adjuvanted with Alhydrogel 2% or Advax on RSV/A/Tracy titers in lung lavage fluids. Compared to saline controls (group 1) infection with live RSV/A/Tracy on day 0 (group 2) reduced titers to below the limit of detection (4.03 $\log_{10}$ PFU/g lung; P<0.00001; Student t test, two-tailed) (FIG. 13, Table 5). Vaccine combinations for groups 3, 4 and 5 RSV titers were reduced to below the limit of detection (4.04-4.13 $\log_{10}$ PFU/g lung; P<0.00001; Student t test, two-tailed). For vaccine group 5, one of 5 cotton rats had detectable virus titer and reduction of 3.72 $\log_{10}$/g lung. There were no statistical differences between the vaccine combinations.

Effect of DT-preF adjuvanted with Alhydrogel 2% or Advax on generation of RSV/A/Tracy- or RSV/B/18537-specific neutralizing antibody. For RSV/A/Tracy-specific neutralizing antibody (NtAb) natural infection with live RSV/A/Tracy (group 2) generated NtAb by day 21 (ca. 5.5 $\log_2$/0.05 mL) and remained at that level through day 39 (FIG. 14; Tables 6-9). This was statistically different than any of the DT-preF vaccines at day 21 (P<0.0036; Student t test, two-tailed). However, following the second vaccination on day 21, there was a robust NtAb response with all of the vaccines which was greater than the live RSV/A/Tracy infection. On days 35 and 39 the NtAb response was greater with the ALH adjuvanted DT-preF at either the 2 or 10 μg/cotton rat dose than with either of the Advax adjuvanted vaccines (P<0.021; Student t test, two-tailed). On day 35 with the Advax-adjuvanted vaccines, the 2 μg/CR dose was statistically better than the 10 μg/CR dose (P=0.046; Student t test, two-tailed).

RSV/B/1853 cross-reacting NtAb were generated by live RSV/A/Tracy infection and by the 4 vaccines FIG. 15; Tables 10-13). The pattern of the NtAb response for the 4 vaccines was similar to that for RSV/A/Tracy but 1-2 $\log_2$ levels lower.

Effect of DT-preF adjuvanted with Alhydrogel 2% or Advax on pulmonary histopathology. Results were analyzed as the sum of area involved (A), sum of severity of the involvement (S) and as a sum of both area and severity together (i.e., A×S). In general, all 3 parameters indicated that compared to the saline control (group 1) the pulmonary cellular infiltrate was not different in the live RSV/A/Tracy infection on day 0 (group 2) while all 4 vaccines produced increased pulmonary cellular infiltrates (groups 3-6) (FIG. 16 and FIG. 17). However, only DT-preF at 2 or 10 μg/cotton rat (groups 3, 4) and containing the ALH adjuvant were statistically different from the saline control (P<0.05, ANOVA). This pattern of protection was reflected in the RSV/A/Tracy neutralization antibody titers, in reduction of viral load in the lungs and to a smaller degree in the nose and in the number of animals within a group with no lesions.

Publications cited herein are hereby specifically incorporated by reference in their entireties and at least for the material for which they are cited.

It should be understood that, while the present disclosure has been provided in detail with respect to certain illustrative and specific aspects thereof, it should not be considered limited to such, as numerous modifications are possible without departing from the broad spirit and scope of the present disclosure as defined in the appended claims. It is, therefore, intended that the appended claims cover all such equivalent variations as fall within the true spirit and scope of the invention.

Tables

TABLE 1

Pre-challenge plaque reducing neutralizing titers (1/PRNT50) of immunized Dams

| Immunization | Average Pre-Challenge 1/PRNT50 (±SD) | Range |
| --- | --- | --- |
| PBS | 0 (0) | 0 |
| DS-Cav1 | 80 (160) | 0-320 |
| DS-Cav1 + Advax-SM | 1360 (2507) | 0-5120 |

TABLE 2

| Group[1] | Vaccine[2] | Volume (mL) | F Protein (μg/CR) | Adjuvant Dose (mg/CR) | Schedule (days) | Challenge[3]/ Harvest | Endpoints |
| --- | --- | --- | --- | --- | --- | --- | --- |
| 1 | Saline | 0.100 | 0 | 0 | 0, +21 | Day +35/+39 | Virus titer in lung lavage and nasal wash fluids by PFU; Histopathology; Serum Nt antibody levels; Frozen right lung lobe |
| 2 | Live RSV/A/Tracy Day 0 | — | — | — | | | |
| 3 | DT-preF + ALH | 0.100 | 2 | 0.1 | | | |
| 4 | DT-preF + ALH | 0.100 | 10 | 0.1 | | | |
| 5 | DT-preF + Advax | 0.115 | 2 | 4 | | | |
| 6 | DT-preF + Advax | 0.115 | 10 | 4 | | | |

Abbreviations: ALH, 2% Brenntag Alhydrogel; PFU, plaque forming units; Nt, neutralizing.
[1]N = 5 animals/group; 30 animals total.
[2]IM route of administration.
[3]All animals to be challenged i.n. (100 μL) with RSV/A/Tracy.

TABLE 3

Group Lung and Body Weights on Day +39

| Group | Vaccine | Lung Lobe Weight Used (g)[1] Mean ± SD | Body Weight (g)[2] Mean ± SD |
| --- | --- | --- | --- |
| 1 | Saline | 0.24 ± 0.03 | 179.0 ± 14.9 |
| 2 | Live RSV/A/Tracy Day 0 | 0.24 ± 0.04 | 186.7 ± 13.6 |
| 3 | DT-preF (2 μg) + ALH | 0.25 ± 0.05 | 171.4 ± 53.3 |
| 4 | DT-preF (10 μg) + ALH | 0.21 ± 0.07 | 185.7 ± 15.4 |

TABLE 3-continued

Group Lung and Body Weights on Day +39

| Group | Vaccine | Lung Lobe Weight Used (g)[1] Mean ± SD | Body Weight (g)[2] Mean ± SD |
|---|---|---|---|
| 5 | DT-preF (2 μg) + Advax | 0.23 ± 0.04 | 173.0 ± 29.2 |
| 6 | DT-preF (10 μg) + Advax | 0.24 ± 0.04 | 180.9 ± 23.3 |

[1]There was no statistically significant difference between the groups (Student t test, two-tailed).
[2]There was no statistically significant difference between the groups (Student t test, two-tailed)

TABLE 4

RSV/A/Tracy Titers in Nasal Wash Fluids on Day +39

| Group | Vaccine | RSV/A/Tracy Titer ($\log_{10}$ total PFU) in Cotton Rat | | | | | | | Change ($\log_{10}$) | T test/2 v. Gp 1* |
|---|---|---|---|---|---|---|---|---|---|---|
| | | A | B | C | D | E | Mean | SD | | |
| 1 | Saline | 4.93 | 4.87 | 5.20 | 5.30 | 4.91 | 5.04 | 0.20 | — | — |
| 2 | Live RSV/A/Tracy Day 0 | 1.30 | d | 0.40 | 0.40 | 0.40 | 0.62 | 0.45 | −4.42 | <0.00001 |
| 3 | DT-preF (2 μg) + ALH | 3.79 | 3.15 | 3.99 | 3.24 | 2.93 | 3.42 | 0.45 | −1.62 | 0.000078 |
| 4 | DT-preF (10 μg) + ALH | 2.41 | 2.73 | 3.60 | 3.89 | 3.73 | 3.27 | 0.66 | −1.77 | 0.00024 |
| 5 | DT-preF (2 μg) + Advax | 3.74 | 2.93 | 3.41 | 3.34 | 4.39 | 3.56 | 0.54 | −1.48 | 0.000055 |
| 6 | DT-preF (10 μg) + Advax | 3.79 | 3.42 | 3.87 | 3.80 | 3.51 | 3.68 | 0.20 | −1.37 | <0.00001 |

*Minimum detection = 0.70 $\log_{10}$ total PFU. d, died. For statistical analysis (Student t test, two-tailed), 0 plaques in an undiluted sample would have been counted as 0.40 $\log_{10}$ total PFU. There were additional significant P values: Group 2 v 3, 4, 5, 6; P = 0.00004, 0.00024, 0.00005, <0.00001, respectively (Student t test, two-tailed).

TABLE 5

RSV/A/Tracy Titers in Lung Lavage Fluids on Day +39

| Group | Vaccine | RSV/A/Tracy Titer ($\log_{10}$ PFU/g lung) in Cotton Rat | | | | | | | Change ($\log_{10}$) | T test/2 v. Gp 1* |
|---|---|---|---|---|---|---|---|---|---|---|
| | | A | B | C | D | E | Mean | SD | | |
| 1 | Saline | 5.25 | 5.25 | 5.39 | 5.38 | 5.26 | 5.31 | 0.07 | — | — |
| 2 | Live RSV/A/Tracy Day 0 | 1.23 | d | 1.27 | 1.41 | 1.19 | 1.28 | 0.10 | −4.03 | <0.00001 |
| 3 | DT-preF (2 μg) + ALH | 1.23 | 1.11 | 1.08 | 1.27 | 1.18 | 1.18 | 0.08 | −4.13 | <0.00001 |
| 4 | DT-preF (10 μg) + ALH | 1.34 | 1.10 | 1.27 | 1.16 | 1.46 | 1.27 | 0.14 | −4.04 | <0.00001 |
| 5 | DT-preF (2 μg) + Advax | 1.21 | 1.19 | 1.32 | 1.27 | 2.94 | 1.59 | 0.76 | −3.72 | <0.00001 |
| 6 | DT-preF (10 μg) + Advax | 1.27 | 1.18 | 1.10 | 1.19 | 1.23 | 1.19 | 0.07 | −4.11 | <0.00001 |

*Minimum detection ~1.4 $\log_{10}$ PFU/g lung. d, died. For statistical analysis (Student t test, two-tailed), 0 plaques in an undiluted sample would have been in the range of 0.90-1.04 $\log_{10}$ PFU/g lung. There were no additional significant P values (Student t test, two-tailed).

TABLE 6

RSV/A/Tracy Serum Neutralizing Titer on Day 0

| Group | Vaccine | RSV/A Neutralizing Titer (log₂) in Cotton Rat | | | | | | | T test/2 v. Gp 1* |
|---|---|---|---|---|---|---|---|---|---|
| | | A | B | C | D | E | Mean | SD | |
| 1 | Saline | 2 | | | | | 2 | | |
| 2 | Live RSV/A/Tracy Day 0 | 2 | | | | | 2 | | |
| 3 | DT-preF (2 µg) + ALH | 2 | | | | | 2 | | |
| 4 | DT-preF (10 µg) + ALH | 2 | | | | | 2 | | |
| 5 | DT-preF (2 µg) + Advax | 2 | | | | | 2 | | |
| 6 | DT-preF (10 µg) + Advax | 2 | | | | | 2 | | |

*Student t test, two-tailed. Minimal detection = 2.5; for statistical analysis a value of <2.5 was counted as 2.

TABLE 7

RSV/A/Tracy Serum Neutralizing Titer on Day +21

| Group | Vaccine | RSV/A Neutralizing Titer (log₂) in Cotton Rat | | | | | | | T test/2 v. Gp 1* |
|---|---|---|---|---|---|---|---|---|---|
| | | A | B | C | D | E | Mean | SD | |
| 1 | Saline | 2 | 2 | 2 | 2 | 2 | 2 | 0 | — |
| 2 | Live RSV/A/Tracy Day 0 | 6.5 | d | 5.0 | 5.0 | 5.5 | 5.5 | 0.7 | 0.0000097 |
| 3 | DT-preF (2 µg) + ALH | 2 | 2.5 | 2 | 4.0 | 4.0 | 2.9 | 1.0 | 0.085 |
| 4 | DT-preF (10 µg) + ALH | 3.0 | 2.5 | 4.0 | 2 | 2 | 2.7 | 0.8 | 0.098 |
| 5 | DT-preF (2 µg) + Advax | 2 | 2 | 2 | 4.0 | 2 | 2.4 | 0.9 | 0.347 |
| 6 | DT-preF (10 µg) + Advax | 2 | 2 | 2 | 2 | 2 | 2 | 0 | — |

*Student t test, two-tailed. Minimal detection = 2.5; for statistical analysis a value of <2.5 was counted as 2. Additional significant P values (Student t test, two-tailed): Group 2 v 3, 4, 5, 6, P ≤ 0.0036. d, died.

TABLE 8

RSV/A/Tracy Serum Neutralizing Titer on Day +35

| Group | Vaccine | RSV/A Neutralizing Titer (log₂) in Cotton Rat | | | | | | | T test/2 v. Gp 1* |
|---|---|---|---|---|---|---|---|---|---|
| | | A | B | C | D | E | Mean | SD | |
| 1 | Saline | 2 | 2 | 2 | 2 | 2 | 2 | 0 | — |
| 2 | Live RSV/A/Tracy Day 0 | 6.0 | d | 6.0 | 4.5 | 6.0 | 5.6 | 0.8 | 0.000011 |
| 3 | DT-preF (2 µg) + ALH | 8.5 | 8.5 | 8.0 | 9.0 | 9.5 | 8.7 | 0.6 | <0.00001 |
| 4 | DT-preF (10 µg) + ALH | 9.0 | 9.0 | 9.0 | 8.5 | 9.5 | 9.0 | 0.4 | <0.00001 |
| 5 | DT-preF (2 µg) + Advax | 8.0 | 7.5 | 8.0 | 7.0 | 7.0 | 7.5 | 0.5 | <0.00001 |
| 6 | DT-preF (10 µg) + Advax | 6.0 | 7.5 | 6.5 | 6.5 | 7.0 | 6.7 | 0.6 | <0.00001 |

*Student t test, two-tailed. Minimal detection = 2.5; for statistical analysis a value of <2.5 was counted as 2. Additional significant P values (Student t test, two-tailed): Group 2 v 3, 4, 5, 6, P < 0.044; Group 3 or 4 v 5, 6, P = 0.0076; Group 5 v 6, P = 0.046. d, died.

TABLE 9

RSV/A/Tracy Serum Neutralizing Titer on Day +39

| Group | Vaccine | RSV/A Neutralizing Titer (log₂) in Cotton Rat | | | | | | | T test/2 v. Gp 1* |
|---|---|---|---|---|---|---|---|---|---|
| | | A | B | C | D | E | Mean | SD | |
| 1 | Saline | 2 | 2 | 2 | 2 | 2 | 2 | 0 | — |
| 2 | Live RSV/A/Tracy Day 0 | 5.0 | d | 6.5 | 5.5 | 6.0 | 5.8 | 0.6 | <0.00001 |
| 3 | DT-preF (2 µg) + ALH | 8.0 | 8.0 | 7.0 | 9.0 | 10.0 | 8.4 | 1.1 | <0.00001 |
| 4 | DT-preF (10 µg) + ALH | 9.0 | 9.0 | 8.5 | 9.0 | 7.5 | 8.6 | 0.7 | <0.00001 |
| 5 | DT-preF (2 µg) + Advax | 7.0 | 7.5 | 8.0 | 8.0 | 4.0 | 6.9 | 1.7 | 0.00018 |
| 6 | DT-preF (10 µg) + Advax | 5.5 | 7.0 | 7.0 | 7.0 | 7.0 | 6.7 | 0.7 | <0.00001 |

*Student t test, two-tailed. Minimal detection = 2.5; for statistical analysis a value of <2.5 was counted as 2. Additional significant P values (Student t test, two-tailed): Group 2 v 3, 4, P < 0.0045; Group 6 v 3, 4, P ≤ 0.021. d, died.

TABLE 10

RSV/B/18537 Serum Neutralizing Titer on Day 0

| Group | Vaccine | RSV/B Neutralizing Titer (log₂) in Cotton Rat | | | | | | | T test/2 v. Gp 1* |
|---|---|---|---|---|---|---|---|---|---|
| | | A | B | C | D | E | Mean | SD | |
| 1 | Saline | 2 | | | | | 2 | | |
| 2 | Live RSV/A/Tracy Day 0 | 2 | | | | | 2 | | |
| 3 | DT-preF (2 µg) + ALH | 2 | | | | | 2 | | |
| 4 | DT-preF (10 µg) + ALH | 2 | | | | | 2 | | |
| 5 | DT-preF (2 µg) + Advax | 2 | | | | | 2 | | |
| 6 | DT-preF (10 µg) + Advax | 2 | | | | | 2 | | |

*Student t test, two-tailed. Minimal detection = 2.5; for statistical analysis a value of <2.5 was counted as 2.

TABLE 11

RSV/B/18537 Serum Neutralizing Titer on Day +21

| Group | Vaccine | RSV/B Neutralizing Titer (log₂) in Cotton Rat | | | | | | | T test/2 v. Gp 1* |
|---|---|---|---|---|---|---|---|---|---|
| | | A | B | C | D | E | Mean | SD | |
| 1 | Saline | 2 | 2 | 2 | 2 | 2 | 2 | 0 | — |
| 2 | Live RSV/A/Tracy Day 0 | 5.0 | d | 3.0 | 3.0 | 2 | 3.3 | 1.3 | 0.058 |
| 3 | DT-preF (2 µg) + ALH | 2 | 2 | 2 | 4.0 | 3.5 | 2.7 | 1.0 | 0.147 |
| 4 | DT-preF (10 µg) + ALH | 2 | 2 | 2 | 2 | 2 | 2 | 0 | — |
| 5 | DT-preF (2 µg) + Advax | 2 | 2 | 2 | 2 | 2 | 2 | 0 | — |
| 6 | DT-preF (10 µg) + Advax | 2 | 2 | 2 | 2 | 2 | 2 | 0 | — |

*Student t test, two-tailed. Minimal detection = 2.5; for statistical analysis a value of <2.5 was counted as 2. There were no additional significant P values (Student t test, two-tailed).

TABLE 12

RSV/B/18537 Serum Neutralizing Titer on Day +35

| Group | Vaccine | RSV/B Neutralizing Titer ($\log_2$) in Cotton Rat | | | | | | | T test/2 v. Gp 1* |
|---|---|---|---|---|---|---|---|---|---|
| | | A | B | C | D | E | Mean | SD | |
| 1 | Saline | 2 | 2 | 2 | 2 | 2 | 2 | 0 | — |
| 2 | Live RSV/A/Tracy Day 0 | 5.0 | d | 3.0 | 2.5 | 2 | 3.1 | 1.3 | 0.092 |
| 3 | DT-preF (2 µg) + ALH | 8.0 | 7.0 | 7.0 | 9.0 | 8.0 | 7.8 | 0.8 | <0.00001 |
| 4 | DT-preF (10 µg) + ALH | 8.0 | 8.5 | 7.5 | 7.5 | 4.0 | 7.1 | 1.8 | 0.00021 |
| 5 | DT-preF (2 µg) + Advax | 4.0 | 6.5 | 7.0 | 5.5 | 7.0 | 6.0 | 1.3 | 0.00011 |
| 6 | DT-preF (10 µg) + Advax | 5.0 | 5.0 | 4.5 | 6.0 | 6.5 | 5.4 | 0.8 | 0.000015 |

*Student t test, two-tailed. Minimal detection = 2.5; for statistical analysis a value of <2.5 was counted as 2. Additional significant P values (Student t test, two-tailed): Group 2 v 3, 4, 5, 6, P ≤ 0.015; Group 3 v 5, 6, P ≤ 0.030.

TABLE 13

RSV/B/18537 Serum Neutralizing Titer on Day +39

| Group | Vaccine | RSV/B Neutralizing Titer ($\log_2$) in Cotton Rat | | | | | | | T test/2 v. Gp 1* |
|---|---|---|---|---|---|---|---|---|---|
| | | A | B | C | D | E | Mean | SD | |
| 1 | Saline | 2 | 2 | 2 | 2 | 2 | 2 | 0 | — |
| 2 | Live RSV/A/Tracy Day 0 | 5.0 | d | 3.0 | 3.5 | 3.0 | 3.6 | 0.9 | 0.0058 |
| 3 | DT-preF (2 µg) + ALH | 8.0 | 7.0 | 7.0 | 8.5 | 8.0 | 7.7 | 0.7 | <0.00001 |
| 4 | DT-preF (10 µg) + ALH | 8.0 | 8.0 | 7.0 | 5.0 | 7.0 | 7.0 | 1.2 | 0.000017 |
| 5 | DT-preF (2 µg) + Advax | 5.0 | 6.5 | 7.0 | 7.0 | 2.0 | 5.5 | 2.1 | 0.0061 |
| 6 | DT-preF (10 µg) + Advax | 5.0 | 5.0 | 5.0 | 5.0 | 6.0 | 5.2 | 0.4 | <0.00001 |

*Student t test, two-tailed. Minimal detection = 2.5; for statistical analysis a value of <2.5 was counted as 2. Additional significant P values (Student t test, two-tailed): Group 2 v 3, 4, 6, P < 0.013; Group 3, 4 v 6, P ≤ 0.015

---

We claim:

1. A method of vaccinating a subject against a respiratory syncytial virus (RSV) infection comprising administering to the subject an RSV F polypeptide stabilized in a prefusion conformation and an inulin adjuvant, wherein the RSV F polypeptide comprises SEQ ID NO: 6 or SEQ ID NO:7, and wherein the administration of the adjuvant increases a ratio of Th1:Th2 cell responses in the subject as compared to a control.

2. The method of claim 1, wherein the inulin comprises a delta inulin.

3. The method of claim 1, wherein the RSV F polypeptide and the inulin adjuvant are administered together in a vaccine formulation comprising a pharmaceutically acceptable carrier.

4. The method of claim 1, wherein the subject is a female.

5. The method of claim 1, wherein the RSV infection is reduced in the subject or an offspring of the subject after vaccination as compared to a control.

6. The method of claim 1, wherein the method decreases a vaccine-enhanced respiratory disease (VERD) in the offspring as compared to a control.

7. The method of claim 1, wherein the method decreases eosinophilia in the subject or offspring as compared to a control.

8. A method of vaccinating a subject against a respiratory syncytial virus (RSV) infection comprising administering to the subject an RSV F polypeptide stabilized in a prefusion conformation and an inulin adjuvant, wherein the inulin adjuvant is selected from the group of alpha-1 inulin, alpha-2 inulin, delta inulin, zeta inulin, epsilon inulin and omega inulin, wherein the RSV F polypeptide comprises SEQ ID NO: 6 or SEQ ID NO:7, and wherein the administration of the adjuvant increases a ratio of Th1:Th2 cell responses in the subject as compared to a control.

9. The method of claim 8, wherein the inulin comprises a delta inulin.

10. The method of claim 8, wherein the RSV F polypeptide and the inulin adjuvant are administered together in a vaccine formulation comprising a pharmaceutically acceptable carrier.

11. The method of claim 8, wherein the subject is a female.

12. The method of claim 8, wherein the RSV infection is reduced in the subject or an offspring of the subject after vaccination as compared to a control.

13. The method of claim 8, wherein the method decreases a vaccine-enhanced respiratory disease (VERD) in the offspring as compared to a control.

14. The method of claim 8, wherein the method decreases eosinophilia in the subject or offspring as compared to a control.

* * * * *